US010435452B2

United States Patent
Rothenberg et al.

(10) Patent No.: US 10,435,452 B2
(45) Date of Patent: Oct. 8, 2019

(54) CADHERIN 26 (CDH26)-FC FUSION PROTEINS AND METHODS OF USE THEREOF TO TREAT INFLAMMATORY CONDITIONS

(71) Applicant: Children's Hospital Medical Center, Cincinnati, OH (US)

(72) Inventors: Marc E. Rothenberg, Cincinnati, OH (US); Julie Caldwell, Cincinnati, OH (US)

(73) Assignee: CHILDREN'S HOSPITAL MEDICAL CENTER, Cincinnati, OH (US)

( * ) Notice: Subject to any disclaimer, the term of this patent is extended or adjusted under 35 U.S.C. 154(b) by 0 days.

(21) Appl. No.: 15/577,502

(22) PCT Filed: May 25, 2016

(86) PCT No.: PCT/US2016/034185
§ 371 (c)(1),
(2) Date: Nov. 28, 2017

(87) PCT Pub. No.: WO2016/196146
PCT Pub. Date: Dec. 8, 2016

(65) Prior Publication Data
US 2018/0148492 A1   May 31, 2018

Related U.S. Application Data

(60) Provisional application No. 62/168,087, filed on May 29, 2015.

(51) Int. Cl.
| | | |
|---|---|---|
| *C07K 14/705* | (2006.01) | |
| *C07K 14/47* | (2006.01) | |
| *A61P 29/00* | (2006.01) | |
| *A61K 38/17* | (2006.01) | |
| *A61K 45/06* | (2006.01) | |
| *A61K 38/00* | (2006.01) | |

(52) U.S. Cl.
CPC .......... *C07K 14/705* (2013.01); *A61K 38/177* (2013.01); *A61K 45/06* (2013.01); *A61P 29/00* (2018.01); *C07K 14/4728* (2013.01); *A61K 38/00* (2013.01); *C07K 2319/02* (2013.01); *C07K 2319/30* (2013.01)

(58) Field of Classification Search
CPC .............. C07K 14/4728; C07K 14/705; C07K 2319/02; C07K 2319/30; A61K 45/06; A61K 38/177; A61K 38/00; A61P 29/00
See application file for complete search history.

(56) References Cited

U.S. PATENT DOCUMENTS

2014/0113372 A1   4/2014   Haque et al.
2014/0286896 A1   9/2014   Rothenberg et al.

FOREIGN PATENT DOCUMENTS

| WO | WO-2005-007175 A2 | 1/2005 |
|---|---|---|
| WO | WO-2005-033134 A2 | 4/2005 |
| WO | WO-2009/089062 A2 | 7/2009 |
| WO | WO-2009/089062 A3 | 7/2009 |
| WO | WO-2009/089062 A8 | 7/2009 |
| WO | WO-2012-178188 A2 | 12/2012 |

OTHER PUBLICATIONS

Recombinant Mouse N-Cadherin Fc Chimera Protein, CF 6626-NC . . . https://www.rndsystems.com > N-Cadherin Jan 14, 2011—Mouse N-Cadherin protein (6626-NC) is manufactured by R&D Systems. Retrieved from the internet Aug. 15, 2018.*
Recombinant Human VE-Cadherin Fc Chimera His-tag Protein, CF . . . https://www.rndsystems.com > VE-Cadherin Jul 4, 2015—Human VE-Cadherin protein (938-VC) is manufactured by R&D Systems. Retrieved from the internet Aug. 15, 2018.*
International Search Report dated Sep. 9, 2016 for International Application No. PCT/US2016/034185, filed May 25, 2016, 4 pages.
Extended European Search Report dated Oct. 4, 2018 for International Application No. PCT/US2016/034185, filed May 25, 2016, 8 pages.
Czajkowsky, D. et al., (2012). "Fc-fusion proteins: new developments and future prospectives." *EMBO Mol. Med.* vol. 4:1015-1028. Includes Supplementary Tables (5 total pages).

* cited by examiner

*Primary Examiner* — Robert S Landsman
(74) *Attorney, Agent, or Firm* — Muriel M. Liberto; Mintz Levin Cohn Ferris Glovsky and Popeo, P.C.

(57) ABSTRACT

The invention provides (CDH26)-based therapeutic agent, compositions comprising same, and methods of treating inflammatory conditions using same.

33 Claims, 26 Drawing Sheets
Specification includes a Sequence Listing.

Fig. 7A
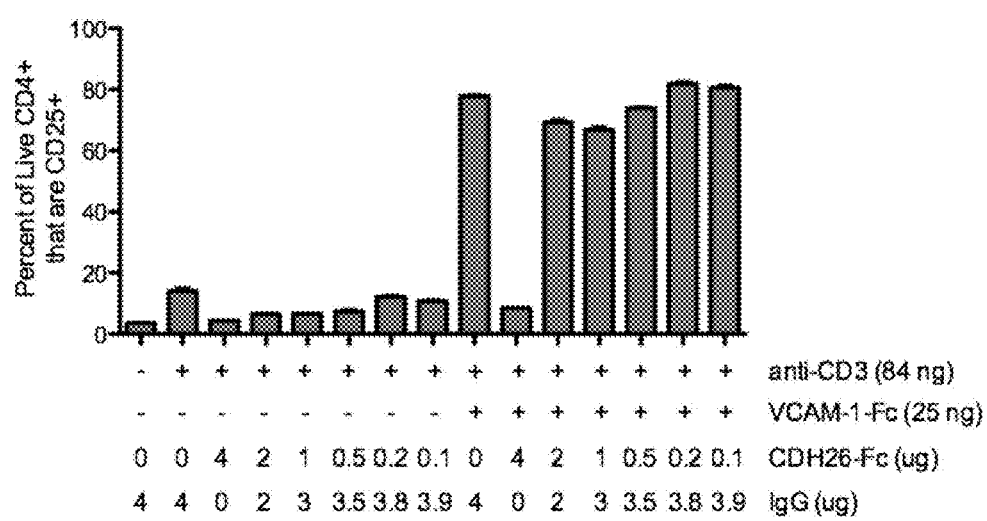
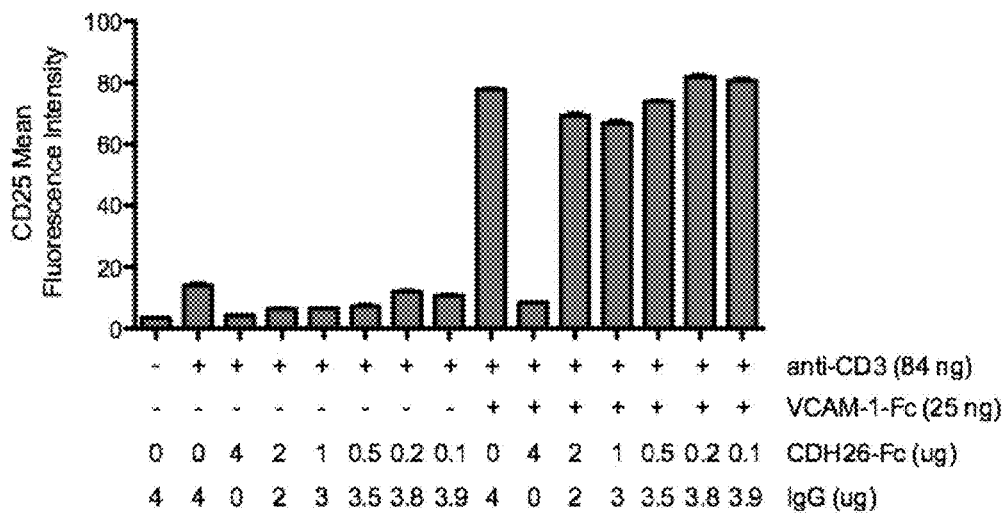

Fig. 7B
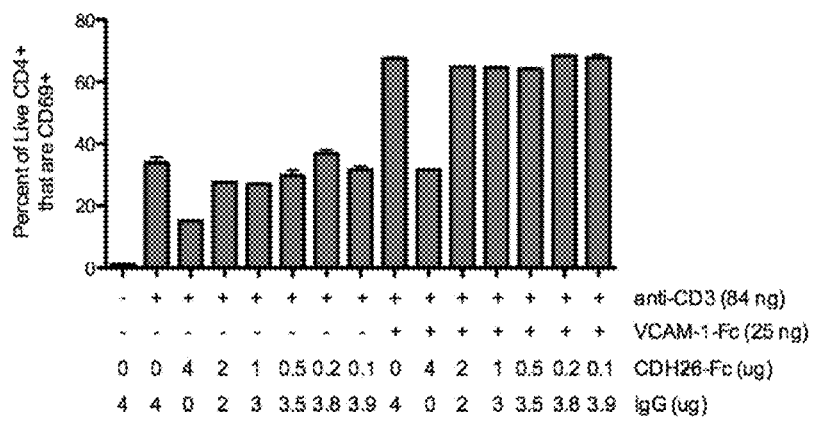
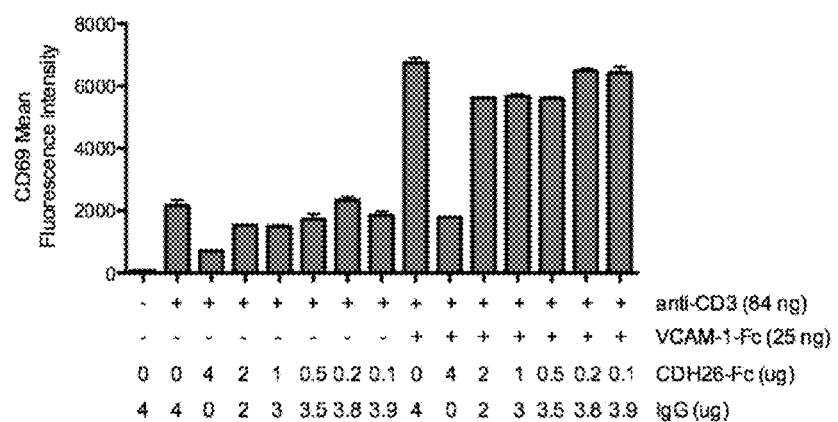

Fig. 7C
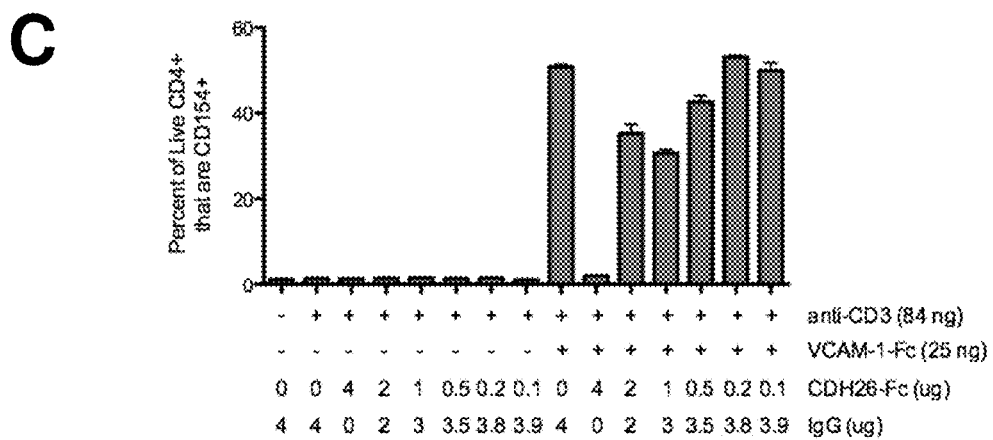
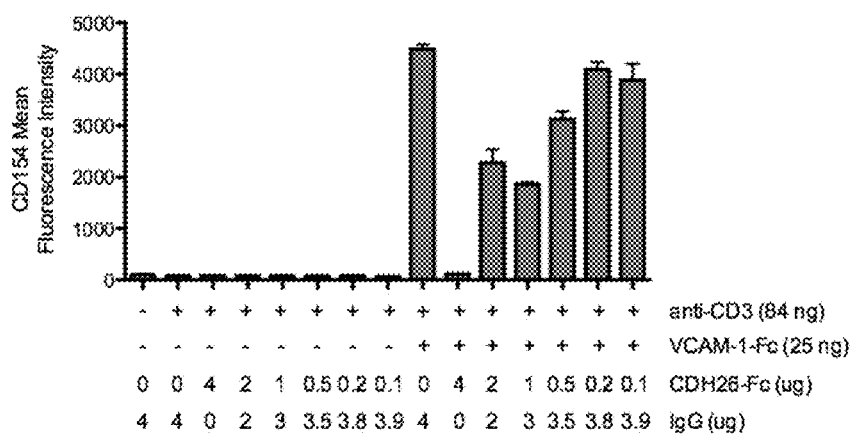

Fig. 7D
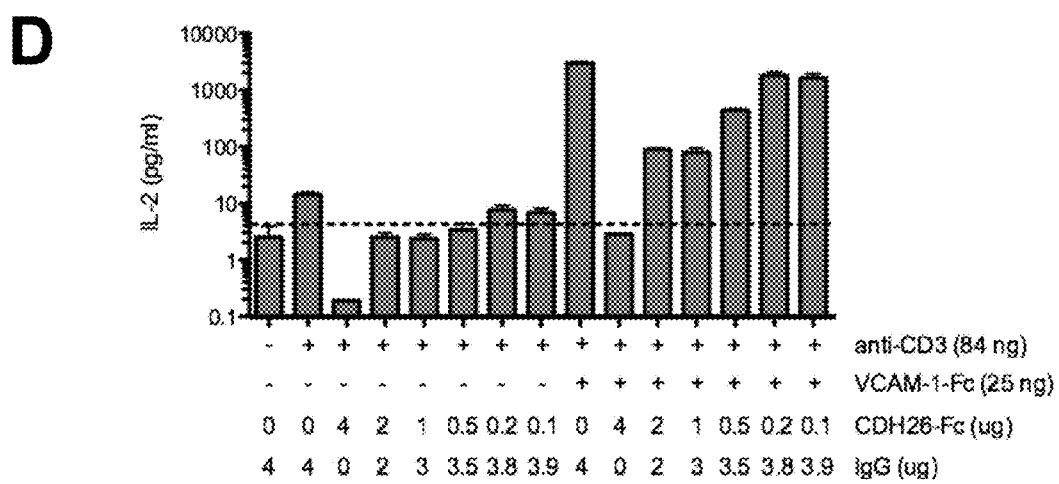
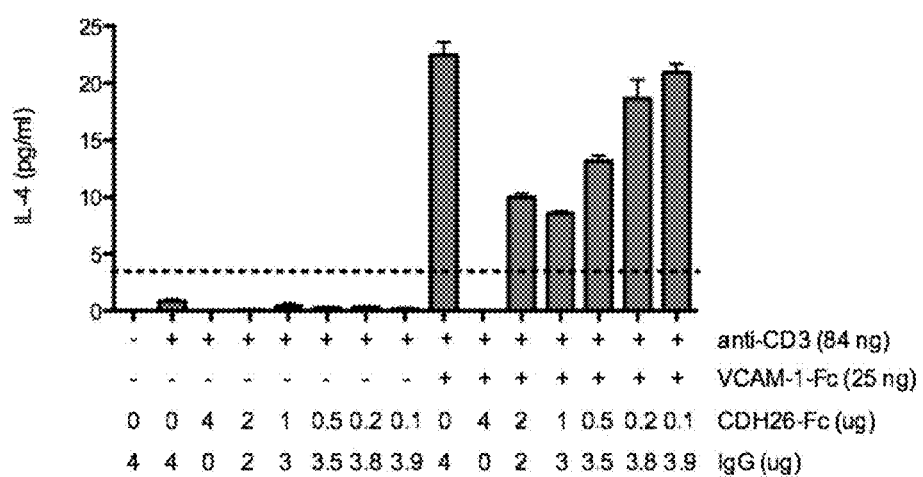

Fig. 8
SEQ ID NO: 9

```
ATGGCCATGAGATCCGGGAGGCACCCCTCGCTGCTGCTGCTTCTAGTGCTGCTGCTGTGG
CTGCTGCAGGTCAGTATCATT¹GACAGTGTTCAACAGGAAACAGATGATCTTACTAAGCAA
ACAAAGGAAAAGATCTACCAGCCTCTACGGCGATCCAAGAGAAGATGGGTTATCACCACC
TTGGAGCTGGAGGAGGAAGACCCGGGACCCTTTCCCAAACTCATTGGTGAGCTGTTCAAT
AATATGTCTTATAACATGTCACTAATGTATCTAATCAGTGGACCTGGTGTGGATGAATAT
CCAGAGATTGGTTTGTTTTCTCTAGAAGATCATGAGAACGGAAGGATATATGTTCACCGC
CCTGTCGATCGAGAAATGACACCATCTTTCACGGTTTATTTTGATGTTGTGGAGCGCTCA
ACAGGAAAAATTGTGGATACATCCTTGATTTTCAACATTAGGATCAGTGATGTGAATGAT
CATGCACCC²CAGTTTCCAGAGAAGGAATTTAACATCACTGTGCAAGAAAACCAATCTGCA
GGGCAACCTATTTTTCAGATGTTAGCAGTCGATTTGGATGAAGAAAACACTCCAAATTCT
CAAGTCCTTTACTTCCTCATTTCTCAAACACCATTACTGAAAGAAAGTGGTTTCCGGGTT
GATCGCCTTAGTGGAGAAATACGACTCTCTGGCTGCTTAGATTATGAGACCGCTCCTCAG
TTTACACTGCTAATCAGAGCCAGGGACTGTGGAGAACCGTCACTGTCATCCACGACCACC
GTTCACGTGGATGTGCAAGAAGGCAACAACCACAGGCCT³GCATTTACCCAGGAGAACTAT
AAGGTTCAGATTCCTGAAGGCCGAGCCAGCCAGGGCGTGTTGCGTCTCCTGGTTCAAGAT
CGAGATTCTCCATTTACATCAGCTTGGAGAGCAAAATTCAACATATTGCATGGCAATGAA
GAGGGGCATTTTGACATTTCGACTGACCCTGAGACCAACGAAGGGATATTAAATGTTATC
AAGCCTTTGGATTATGAGACTCGCCCAGCGCAAAGCCTCATCATTGTCGTGGAGAATGAG
GAGAGGCTCGTCTTCTGTGAGAGAGGAAAGCTTCAGCCGCCAAGGAAGGCAGCAGCCAGC
GCCACTGTGAGTGTGCAGGTGACAGACGCCAACGACCCACCAGCC⁴TTTCACCCCCAGAGC
TTCATTGTCAATAAAGAGGAGGGCGCCAGGCCTGGGACCCTGTTGGGAACTTTTAATGCC
ATGGATCCAGACAGCCAGATAAGATATGAACTGGTTCATGACCCAGCAAATTGGGTCAGC
GTCGACAAAAACTCCGGAGTGGTCATCACCGTGGAGCCAATTGACCGAGAATCCCCTCAT
GTAAATAACAGTTTTTATGTAATCATCATTCACGCTGTTGATGATGGCTTCCCACCGCAG
ACTGCTACAGGGACCCTAATGCTCTTCCTGTCTGACATCAATGACAACGTCCCG⁵ACTCTC
CGGCCACGTTCCCGCTACATGGAGGTCTGTGAGTCTGCTGTGCATGAGCCCCTCCACATC
GAGGCAGAGGATCCGGACCTGGAGCCGTTCTCTGACCCATTTACATTTGAATTGGACAAT
ACCTGGGGAAATGCGGAGGACACATGGAAGTTGGGGAGAAATTGGGGTCAATCAGTTGAA
CTTTTAACCTTGAGAAGCCTGCCACGTGGTAATTACTTGGTGCCACTCTTCATTGGAGAC
AAACAGGGACTTTCCCAGAAGCAAACTGTCCATGTAAGGATCTGC⁶CCCTGTGCCAGTGGG
CTCACATGTGTGGAGCTTGCAGATGACAAAACTCACACATGCCCACCGTGCCCAGCACCT
GAACTCCTGGGGGGACCGTCAGTCTTCCTCTTCCCCCAAAACCCAAGGACACCCTCATG
ATCTCCCGGACCCCTGAGGTCACATGCGTGGTGGTGGACGTGAGCCACGAAGACCCTGAG
GTCAAGTTCAACTGGTACGTGGACGGCGTGGAGGTGCATAATGCCAAGACAAAGCCGCGG
GAGGAGCAGTACAACAGCACGTACCGTGTGGTCAGCGTCCTCACCGTCCTGCACCAGGAC
TGGCTGAATGGCAAGGAGTACAAGTGCAAGGTCTCCAACAAAGCCCTCCCAGCCCCCATC
GAGAAAACCATCTCCAAAGCCAAAGGGCAGCCCCGAGAACCACAGGTGTACACCCTGCCC
CCATCCCGGGAGGAGATGACCAAGAACCAGGTCAGCCTGACCTGCCTGGTCAAAGGCTTC
TATCCCAGCGACATCGCCGTGGAGTGGGAGAGCAATGGGCAGCCGGAGAACAACTACAAG
ACCACGCCTCCCGTGCTGGACTCCGACGGCTCCTTCTTCCTCTACAGCAAGCTCACCGTG
GACAAGAGCAGGTGGCAGCAGGGGAACGTCTTCTCATGCTCCGTGATGCACGAGGCTCTG
CACAACCACTACACGCAGAAGAGCCTCTCCCTGTCTCCGGGTAAATGA⁷
```

Fig. 9

SEQ ID NO: 8

MAMRSGRHPSLLLLVLLLMLLQVSII$^1$DSVQQETDDLTKQTKEKIYQPLRRSKRRWVITT
LELEEDPGPFPKLIGELFNNMSYNMSIMYLISGPGVDEYPEIGLFSLEDHENGRIYVHR
PVDREMTPSFTVYFDVVERSTGKIVDTSLIFNIRISDVNDHAP$^2$QFPEKEFNITVQENQSA
GQPIFQMLAVDLDEENTPNSQVLYFLISQTPLLKESGFRVDRLSGEIRLSGCLDYETAPQ
FTLLIRARDCGEPSLSSTTTVHVDVQEGNNHRP$^3$AFTQENYKVQIPEGRASQVLRLLVQD
RDSPFTSAWRAKFNILHGNEEGHFDISTDPETNEGILNVIKPLDYETRPAQSLIIVVENE
ERLVFCERGKLQPPRKAAASATVSVQVTDANDPPAF$^4$HPQSFIVNKEEGARPGTLLGTFNA
MDPDSQIRYELVHDPANWVSVDKNSGVVITVEPIDRESPHVNNSFYVIIHAVDDGFPPQ
TATGTLMLFLSDINDNVP$^5$TLRPRSRYMEVCESAVHEPLHIEAEDPDLEPFSDPFTFELDN
TWGNAEDTWKLGRNWGQSVELLTLRSLPRGNYLVPLFIGDKQGLSQKQTVHVRIC$^6$PCASG
LTCVELADDKTHTCPPCPAPELLGGPSVFLFPPKPKDTLMISRTPEVTCVVVDVSHEDPE
VKFNWYVDGVEVHNAKTKPREEQYNSTYRVVSVLTVLHQDWLNGKEYKCKVSNKALPAPI
EKTISKAKGQPREPQVYTLPPSREEMTKNQVSLTCLVKGFYPSDIAVEWESNGQPENNYK
TTPPVLDSDGSFFLYSKLTVDKSRWQQGNVFSCSVMHEALHNHYTQKSLSLSPGK$^7$*

EC1

EC2

EC3

EC4

EC5

SEQUENCE LISTING

<160> NUMBER OF SEQ ID NOS: 11

<210> SEQ ID NO 1
<211> LENGTH: 27
<212> TYPE: PRT
<213> ORGANISM: Artificial Sequence
<220> FEATURE:
<223> OTHER INFORMATION: MAMRSGRHPSLLLLLVLLLWLLQVSII

<400> SEQUENCE: 1

Met Ala Met Arg Ser Gly Arg His Pro Ser Leu Leu Leu Leu Val
1               5                   10                  15

Leu Leu Leu Trp Leu Leu Gln Val Ser Ile Ile
            20                  25

<210> SEQ ID NO 2
<211> LENGTH: 92
<212> TYPE: PRT
<213> ORGANISM: Artificial Sequence
<220> FEATURE:
<223> OTHER INFORMATION: EC1

<400> SEQUENCE: 2

Pro Lys Leu Ile Gly Glu Leu Phe Asn Asn Met Ser Tyr Asn Met Ser
1               5                   10                  15

Leu Met Tyr Leu Ile Ser Gly Pro Gly Val Asp Glu Tyr Pro Glu Ile
            20                  25                  30

Gly Leu Phe Ser Leu Glu Asp His Glu Asn Gly Arg Ile Tyr Val His
        35                  40                  45

Arg Pro Val Asp Arg Glu Met Thr Pro Ser Phe Thr Val Tyr Phe Asp
    50                  55                  60

Val Val Glu Arg Ser Thr Gly Lys Ile Val Asp Thr Ser Leu Ile Phe
65                  70                  75                  80

Asn Ile Arg Ile Ser Asp Val Asn Asp His Ala Pro
                85                  90

<210> SEQ ID NO 3
<211> LENGTH: 88
<212> TYPE: PRT
<213> ORGANISM: Artificial Sequence
<220> FEATURE:
<223> OTHER INFORMATION: EC2

<400> SEQUENCE: 3

Gln Met Leu Ala Val Asp Leu Asp Glu Glu Asn Thr Pro Asn Ser Gln
1               5                   10                  15

Val Leu Tyr Phe Leu Ile Ser Gln Thr Pro Leu Leu Lys Glu Ser Gly
            20                  25                  30

Phe Arg Val Asp Arg Leu Ser Gly Glu Ile Arg Leu Ser Gly Cys Leu
        35                  40                  45

Asp Tyr Glu Thr Ala Pro Gln Phe Thr Leu Leu Ile Arg Ala Arg Asp
    50                  55                  60

Cys Gly Glu Pro Ser Leu Ser Ser Thr Thr Thr Val His Val Asp Val
65                  70                  75                  80

Gln Glu Gly Asn Asn His Arg Pro
                85

<210> SEQ ID NO 4
<211> LENGTH: 101
<212> TYPE: PRT
<213> ORGANISM: Artificial Sequence

```
<220> FEATURE:
<223> OTHER INFORMATION: EC3

<400> SEQUENCE: 4

Leu Leu Val Gln Asp Arg Asp Ser Pro Phe Thr Ser Ala Trp Arg Ala
1               5                   10                  15

Lys Phe Asn Ile Leu His Gly Asn Glu Gly His Phe Asp Ile Ser
            20                  25                  30

Thr Asp Pro Glu Thr Asn Glu Gly Ile Leu Asn Val Ile Lys Pro Leu
        35                  40                  45

Asp Tyr Glu Thr Arg Pro Ala Gln Ser Leu Ile Ile Val Val Glu Asn
50                  55                  60

Glu Glu Arg Leu Val Phe Cys Glu Arg Gly Lys Leu Gln Pro Pro Arg
65                  70                  75                  80

Lys Ala Ala Ala Ser Ala Thr Val Ser Val Gln Val Thr Asp Ala Asn
                85                  90                  95

Asp Pro Pro Ala Phe
            100

<210> SEQ ID NO 5
<211> LENGTH: 81
<212> TYPE: PRT
<213> ORGANISM: Artificial Sequence
<220> FEATURE:
<223> OTHER INFORMATION: EC4

<400> SEQUENCE: 5

Phe Asn Ala Met Asp Pro Asp Ser Gln Ile Arg Tyr Glu Leu Val His
1               5                   10                  15

Asp Pro Ala Asn Trp Val Ser Val Asp Lys Asn Ser Gly Val Val Ile
            20                  25                  30

Thr Val Glu Pro Ile Asp Arg Glu Ser Pro His Val Asn Asn Ser Phe
        35                  40                  45

Tyr Val Ile Ile Ile His Ala Val Asp Asp Gly Phe Pro Pro Gln Thr
50                  55                  60

Ala Thr Gly Thr Leu Met Leu Phe Leu Ser Asp Ile Asn Asp Asn Val
65                  70                  75                  80

Pro

<210> SEQ ID NO 6
<211> LENGTH: 90
<212> TYPE: PRT
<213> ORGANISM: Artificial Sequence
<220> FEATURE:
<223> OTHER INFORMATION: EC5

<400> SEQUENCE: 6

Arg Tyr Met Glu Val Cys Glu Ser Ala Val His Glu Pro Leu His Ile
1               5                   10                  15

Glu Ala Glu Asp Pro Asp Leu Gly Pro Phe Ser Asp Pro Phe Thr Phe
            20                  25                  30

Glu Leu Asp Asn Thr Trp Gly Asn Ala Glu Asp Thr Trp Lys Leu Gly
        35                  40                  45

Arg Asn Trp Gly Gln Ser Val Glu Leu Leu Thr Leu Arg Ser Leu Pro
50                  55                  60

Arg Gly Asn Tyr Leu Val Pro Leu Phe Ile Gly Asp Lys Gln Gly Leu
65                  70                  75                  80

Ser Gln Lys Gln Val His Val Arg Ile Cys
```

```
                    85                  90

<210> SEQ ID NO 7
<211> LENGTH: 227
<212> TYPE: PRT
<213> ORGANISM: Artificial Sequence
<220> FEATURE:
<223> OTHER INFORMATION: Fc

<400> SEQUENCE: 7

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 8
<211> LENGTH: 835
<212> TYPE: PRT
<213> ORGANISM: Homo sapiens

<400> SEQUENCE: 8

Met Ala Met Arg Ser Gly Arg His Pro Ser Leu Leu Leu Leu Leu Val
1               5                   10                  15

Leu Leu Leu Trp Leu Leu Gln Val Ser Ile Ile Asp Ser Val Gln Gln
            20                  25                  30

Glu Thr Asp Asp Leu Thr Lys Gln Thr Lys Glu Lys Ile Tyr Gln Pro
        35                  40                  45

Leu Arg Arg Ser Lys Arg Arg Trp Val Ile Thr Thr Leu Glu Leu Glu
    50                  55                  60

Glu Glu Asp Pro Gly Pro Phe Pro Lys Leu Ile Gly Glu Leu Phe Asn
65                  70                  75                  80
```

```
Asn Met Ser Tyr Asn Met Ser Leu Met Tyr Leu Ile Ser Gly Pro Gly
                85                  90                  95

Val Asp Glu Tyr Pro Glu Ile Gly Leu Phe Ser Leu Glu Asp His Glu
            100                 105                 110

Asn Gly Arg Ile Tyr Val His Arg Pro Val Asp Arg Glu Met Thr Pro
        115                 120                 125

Ser Phe Thr Val Tyr Phe Asp Val Val Glu Arg Ser Thr Gly Lys Ile
    130                 135                 140

Val Asp Thr Ser Leu Ile Phe Asn Ile Arg Ile Ser Asp Val Asn Asp
145                 150                 155                 160

His Ala Pro Gln Phe Pro Glu Lys Glu Phe Asn Ile Thr Val Gln Glu
                165                 170                 175

Asn Gln Ser Ala Gly Gln Pro Ile Phe Gln Met Leu Ala Val Asp Leu
            180                 185                 190

Asp Glu Glu Asn Thr Pro Asn Ser Gln Val Leu Tyr Phe Leu Ile Ser
        195                 200                 205

Gln Thr Pro Leu Leu Lys Glu Ser Gly Phe Arg Val Asp Arg Leu Ser
    210                 215                 220

Gly Glu Ile Arg Leu Ser Gly Cys Leu Asp Tyr Glu Thr Ala Pro Gln
225                 230                 235                 240

Phe Thr Leu Leu Ile Arg Ala Arg Asp Cys Gly Glu Pro Ser Leu Ser
                245                 250                 255

Ser Thr Thr Thr Val His Val Asp Val Gln Glu Gly Asn Asn His Arg
            260                 265                 270

Pro Ala Phe Thr Gln Glu Asn Tyr Lys Val Gln Ile Pro Glu Gly Arg
        275                 280                 285

Ala Ser Gln Gly Val Leu Arg Leu Leu Val Gln Asp Arg Asp Ser Pro
    290                 295                 300

Phe Thr Ser Ala Trp Arg Ala Lys Phe Asn Ile Leu His Gly Asn Glu
305                 310                 315                 320

Glu Gly His Phe Asp Ile Ser Thr Asp Pro Glu Thr Asn Glu Gly Ile
                325                 330                 335

Leu Asn Val Ile Lys Pro Leu Asp Tyr Glu Thr Arg Pro Ala Gln Ser
            340                 345                 350

Leu Ile Ile Val Val Glu Asn Glu Glu Arg Leu Val Phe Cys Glu Arg
        355                 360                 365

Gly Lys Leu Gln Pro Pro Arg Lys Ala Ala Ser Ala Thr Val Ser
    370                 375                 380

Val Gln Val Thr Asp Ala Asn Asp Pro Pro Ala Phe His Pro Gln Ser
385                 390                 395                 400

Phe Ile Val Asn Lys Glu Glu Gly Ala Arg Pro Gly Thr Leu Leu Gly
                405                 410                 415

Thr Phe Asn Ala Met Asp Pro Asp Ser Gln Ile Arg Tyr Glu Leu Val
            420                 425                 430

His Asp Pro Ala Asn Trp Val Ser Val Asp Lys Asn Ser Gly Val Val
        435                 440                 445

Ile Thr Val Glu Pro Ile Asp Arg Glu Ser Pro His Val Asn Asn Ser
    450                 455                 460

Phe Tyr Val Ile Ile His Ala Val Asp Asp Gly Phe Pro Pro Gln
465                 470                 475                 480

Thr Ala Thr Gly Thr Leu Met Leu Phe Leu Ser Asp Ile Asn Asp Asn
                485                 490                 495
```

```
Val Pro Thr Leu Arg Pro Arg Ser Arg Tyr Met Glu Val Cys Glu Ser
            500                 505                 510

Ala Val His Glu Pro Leu His Ile Glu Ala Glu Asp Pro Asp Leu Glu
            515                 520                 525

Pro Phe Ser Asp Pro Phe Thr Phe Glu Leu Asp Asn Thr Trp Gly Asn
            530                 535             540

Ala Glu Asp Thr Trp Lys Leu Gly Arg Asn Trp Gly Gln Ser Val Glu
545                 550                 555                 560

Leu Leu Thr Leu Arg Ser Leu Pro Arg Gly Asn Tyr Leu Val Pro Leu
                565                 570                 575

Phe Ile Gly Asp Lys Gln Gly Leu Ser Gln Lys Gln Thr Val His Val
            580                 585                 590

Arg Ile Cys Pro Cys Ala Ser Gly Leu Thr Cys Val Glu Leu Ala Asp
            595                 600                 605

Asp Lys Thr His Thr Cys Pro Pro Cys Pro Ala Pro Glu Leu Leu Gly
            610                 615                 620

Gly Pro Ser Val Phe Leu Phe Pro Pro Lys Pro Lys Asp Thr Leu Met
625                 630                 635                 640

Ile Ser Arg Thr Pro Glu Val Thr Cys Val Val Val Asp Val Ser His
                645                 650                 655

Glu Asp Pro Glu Val Lys Phe Asn Trp Tyr Val Asp Gly Val Glu Val
            660                 665                 670

His Asn Ala Lys Thr Lys Pro Arg Glu Glu Gln Tyr Asn Ser Thr Tyr
            675                 680                 685

Arg Val Val Ser Val Leu Thr Val Leu His Gln Asp Trp Leu Asn Gly
            690                 695                 700

Lys Glu Tyr Lys Cys Lys Val Ser Asn Lys Ala Leu Pro Ala Pro Ile
705                 710                 715                 720

Glu Lys Thr Ile Ser Lys Ala Lys Gly Gln Pro Arg Glu Pro Gln Val
                725                 730                 735

Tyr Thr Leu Pro Pro Ser Arg Glu Glu Met Thr Lys Asn Gln Val Ser
            740                 745                 750

Leu Thr Cys Leu Val Lys Gly Phe Tyr Pro Ser Asp Ile Ala Val Glu
            755                 760                 765

Trp Glu Ser Asn Gly Gln Pro Glu Asn Asn Tyr Lys Thr Thr Pro Pro
            770                 775                 780

Val Leu Asp Ser Asp Gly Ser Phe Phe Leu Tyr Ser Lys Leu Thr Val
785                 790                 795                 800

Asp Lys Ser Arg Trp Gln Gln Gly Asn Val Phe Ser Cys Ser Val Met
                805                 810                 815

His Glu Ala Leu His Asn His Tyr Thr Gln Lys Ser Leu Ser Leu Ser
            820                 825                 830

Pro Gly Lys
        835

<210> SEQ ID NO 9
<211> LENGTH: 2508
<212> TYPE: DNA
<213> ORGANISM: Homo sapiens

<400> SEQUENCE: 9
atggccatga gatccgggag gcacccctcg ctgctgctgc ttctagtgct gctgctgtgg      60
ctgctgcagg tcagtatcat tgacagtgtt caacaggaaa cagatgatct tactaagcaa     120
acaaaggaaa agatctacca gcctctacgg cgatccaaga agatgggt tatcaccacc      180
```

```
ttggagctgg aggaggaaga cccgggaccc tttcccaaac tcattggtga gctgttcaat      240
aatatgtctt ataacatgtc actaatgtat ctaatcagtg gacctggtgt ggatgaatat      300
ccagagattg gtttgttttc tctagaagat catgagaacg gaaggatata tgttcaccgc      360
cctgtcgatc gagaaatgac accatctttc acggtttatt ttgatgttgt ggagcgctca      420
acaggaaaaa ttgtggatac atccttgatt ttcaacatta ggatcagtga tgtgaatgat      480
catgcacccc agtttccaga gaaggaattt aacatcactg tgcaagaaaa ccaatctgca      540
gggcaaccta ttttcagat gttagcagtc gatttggatg aagaaaacac tccaaattct       600
caagtccttt acttcctcat ttctcaaaca ccattactga agaaagtgg tttccggggtt       660 gatcgcctta gtggagaaat acgactctct ggctgcttag attatgagac cgctcctcag      720
tttacactgc taatcagagc cagggactgt ggagaaccgt cactgtcatc cacgaccacc      780
gttcacgtgg atgtgcaaga aggcaacaac cacaggcctg catttaccca ggagaactat      840
aaggttcaga ttcctgaagg ccgagccagc cagggcgtgt tgcgtctcct ggttcaagat      900
cgagattctc catttacatc agcttggaga gcaaaattca acatattgca tggcaatgaa      960
gaggggcatt ttgacatttc gactgaccct gagaccaacg aagggatatt aaatgttatc     1020
aagcctttgg attatgagac tcgcccagcg caaagcctca tcattgtcgt ggagaatgag     1080
gagaggctcg tcttctgtga gagggaaag cttcagccgc caaggaaggc agcagccagc      1140
gccactgtga gtgtgcaggt gacagacgcc aacgacccac cagcctttca cccccagagc     1200
ttcattgtca ataaagagga gggcgccagg cctgggaccc tgttgggaac ttttaatgcc     1260
atggatccag acagccagat aagatatgaa ctggttcatg acccagcaaa ttgggtcagc     1320
gtcgacaaaa actccggagt ggtcatcacc gtggagccaa ttgaccgaga atcccctcat     1380
gtaaataaca gttttatgt aatcatcatt cacgctgttg atgatggctt cccaccgcag      1440
actgctacag ggaccctaat gctcttcctg tctgacatca atgacaacgt cccgactctc     1500
cggccacgtt cccgctacat ggaggtctgt gagtctgctg tgcatgagcc cctccacatc     1560
gaggcagagg atccggacct ggagccgttc tctgacccat ttacatttga attggacaat     1620
acctggggaa atgcggagga cacatggaag ttgggggagaa attggggtca atcagttgaa     1680 cttttaaccct tgagaagcct gccacgtggt aattacttgg tgccactctt cattggagac     1740 aaacaggggac tttcccagaa gcaaactgtc catgtaagga tctgccctg tgccagtggg      1800 ctcacatgtg tggagcttgc agatgacaaa actcacacat gcccaccgtg cccagcacct     1860
gaactcctgg ggggaccgtc agtcttcctc ttccccccaa aacccaagga caccctcatg     1920
atctcccgga cccctgaggt cacatgcgtg gtggtggacg tgagccacga agaccctgag     1980
gtcaagttca actggtacgt ggacggcgtg gaggtgcata atgccaagac aaagccgcgg     2040
gaggagcagt acaacagcac gtaccgtgtg gtcagcgtcc tcaccgtcct gcaccaggac     2100
tggctgaatg gcaaggagta caagtgcaag gtctccaaca aagcccctcc cagccccatc     2160
gagaaaacca tctccaaagc caaagggcag ccccgagaac cacaggtgta caccctgccc     2220
ccatcccggg aggagatgac caagaaccag gtcagcctga cctgcctggt caaaggcttc     2280
tatcccagcg acatcgccgt ggagtgggag agcaatgggc agccggagaa caactacaag     2340
accacgcctc ccgtgctgga ctccgacggc tccttcttcc tctacagcaa gctcaccgtg     2400
gacaagagca ggtggcagca ggggaacgtc ttctcatgct ccgtgatgca cgaggctctg     2460
cacaaccact acacgcagaa gagcctctcc ctgtctccgg gtaaatga                  2508
```

-continued

```
<210> SEQ ID NO 10
<211> LENGTH: 545
<212> TYPE: PRT
<213> ORGANISM: Artificial Sequence
<220> FEATURE:
<223> OTHER INFORMATION: segment 1 comprises or consists of the CDH26
      extracellular region defined by amino acids asparagine 55 (Asp55)
      to serine 599 (Ser599)

<400> SEQUENCE: 10

Arg Trp Val Ile Thr Thr Leu Glu Leu Glu Glu Glu Asp Pro Gly Pro
1               5                   10                  15

Phe Pro Lys Leu Ile Gly Glu Leu Phe Asn Asn Met Ser Tyr Asn Met
            20                  25                  30

Ser Leu Met Tyr Leu Ile Ser Gly Pro Gly Val Asp Glu Tyr Pro Glu
        35                  40                  45

Ile Gly Leu Phe Ser Leu Glu Asp His Glu Asn Gly Arg Ile Tyr Val
    50                  55                  60

His Arg Pro Val Asp Arg Glu Met Thr Pro Ser Phe Thr Val Tyr Phe
65                  70                  75                  80

Asp Val Val Glu Arg Ser Thr Gly Lys Ile Val Asp Thr Ser Leu Ile
                85                  90                  95

Phe Asn Ile Arg Ile Ser Asp Val Asn Asp His Ala Pro Gln Phe Pro
            100                 105                 110

Glu Lys Glu Phe Asn Ile Thr Val Gln Glu Asn Gln Ser Ala Gly Gln
        115                 120                 125

Pro Ile Phe Gln Met Leu Ala Val Asp Leu Asp Glu Glu Asn Thr Pro
    130                 135                 140

Asn Ser Gln Val Leu Tyr Phe Leu Ile Ser Gln Thr Pro Leu Leu Lys
145                 150                 155                 160

Glu Ser Gly Phe Arg Val Asp Arg Leu Ser Gly Glu Ile Arg Leu Ser
                165                 170                 175

Gly Cys Leu Asp Tyr Glu Thr Ala Pro Gln Phe Thr Leu Leu Ile Arg
            180                 185                 190

Ala Arg Asp Cys Gly Glu Pro Ser Leu Ser Ser Thr Thr Thr Val His
        195                 200                 205

Val Asp Val Gln Glu Gly Asn Asn His Arg Pro Ala Phe Thr Gln Glu
    210                 215                 220

Asn Tyr Lys Val Gln Ile Pro Glu Gly Arg Ala Ser Gln Gly Val Leu
225                 230                 235                 240

Arg Leu Leu Val Gln Asp Arg Asp Ser Pro Phe Thr Ser Ala Trp Arg
                245                 250                 255

Ala Lys Phe Asn Ile Leu His Gly Asn Glu Glu Gly His Phe Asp Ile
            260                 265                 270

Ser Thr Asp Pro Glu Thr Asn Glu Gly Ile Leu Asn Val Ile Lys Pro
        275                 280                 285

Leu Asp Tyr Glu Thr Arg Pro Ala Gln Ser Leu Ile Ile Val Val Glu
    290                 295                 300

Asn Glu Glu Arg Leu Val Phe Cys Glu Arg Gly Lys Leu Gln Pro Pro
305                 310                 315                 320

Arg Lys Ala Ala Ala Ser Ala Thr Val Ser Val Gln Val Thr Asp Ala
                325                 330                 335

Asn Asp Pro Pro Ala Phe His Pro Gln Ser Phe Ile Val Asn Lys Glu
            340                 345                 350

Glu Gly Ala Arg Pro Gly Thr Leu Leu Gly Thr Phe Asn Ala Met Asp
```

-continued

```
                355                 360                 365
Pro Asp Ser Gln Ile Arg Tyr Glu Leu Val His Asp Pro Ala Asn Trp
370                 375                 380
Val Ser Val Asp Lys Asn Ser Gly Val Val Ile Thr Val Glu Pro Ile
385                 390                 395                 400
Asp Arg Glu Ser Pro His Val Asn Asn Ser Phe Tyr Val Ile Ile
            405                 410                 415
His Ala Val Asp Asp Gly Phe Pro Pro Gln Thr Ala Thr Gly Thr Leu
            420                 425                 430
Met Leu Phe Leu Ser Asp Ile Asn Asp Asn Val Pro Thr Leu Arg Pro
            435                 440                 445
Arg Ser Arg Tyr Met Glu Val Cys Glu Ser Ala Val His Glu Pro Leu
        450                 455                 460
His Ile Glu Ala Glu Asp Pro Asp Leu Gly Pro Phe Ser Asp Pro Phe
465                 470                 475                 480
Thr Phe Glu Leu Asp Asn Thr Trp Gly Asn Ala Glu Asp Thr Trp Lys
                485                 490                 495
Leu Gly Arg Asn Trp Gly Gln Ser Val Glu Leu Thr Leu Arg Ser
            500                 505                 510
Leu Pro Arg Gly Asn Tyr Leu Val Pro Leu Phe Ile Gly Asp Lys Gln
            515                 520                 525
Gly Leu Ser Gln Lys Gln Thr Val His Val Arg Ile Cys Pro Cys Ala
            530                 535                 540
Ser
545

<210> SEQ ID NO 11
<211> LENGTH: 832
<212> TYPE: PRT
<213> ORGANISM: Homo sapiens

<400> SEQUENCE: 11

Met Ala Met Arg Ser Gly Arg His Pro Ser Leu Leu Leu Leu Leu Val
1               5                   10                  15
Leu Leu Leu Trp Leu Leu Gln Val Ser Ile Ile Asp Ser Val Gln Gln
            20                  25                  30
Glu Thr Asp Asp Leu Thr Lys Gln Thr Lys Glu Lys Ile Tyr Gln Pro
        35                  40                  45
Leu Arg Arg Ser Lys Arg Arg Trp Val Ile Thr Thr Leu Glu Leu Glu
    50                  55                  60
Glu Glu Asp Pro Gly Pro Phe Pro Lys Leu Ile Gly Glu Leu Phe Asn
65                  70                  75                  80
Asn Met Ser Tyr Asn Met Ser Leu Met Tyr Leu Ile Ser Gly Pro Gly
                85                  90                  95
Val Asp Glu Tyr Pro Glu Ile Gly Leu Phe Ser Leu Glu Asp His Glu
            100                 105                 110
Asn Gly Arg Ile Tyr Val His Arg Pro Val Asp Arg Glu Met Thr Pro
        115                 120                 125
Ser Phe Thr Val Tyr Phe Asp Val Val Glu Arg Ser Thr Gly Lys Ile
    130                 135                 140
Val Asp Thr Ser Leu Ile Phe Asn Ile Arg Ile Ser Asp Val Asn Asp
145                 150                 155                 160
His Ala Pro Gln Phe Pro Glu Lys Glu Phe Asn Ile Thr Val Gln Glu
                165                 170                 175
```

```
Asn Gln Ser Ala Gly Gln Pro Ile Phe Gln Met Leu Ala Val Asp Leu
            180                 185                 190

Asp Glu Glu Asn Thr Pro Asn Ser Gln Val Leu Tyr Phe Leu Ile Ser
        195                 200                 205

Gln Thr Pro Leu Leu Lys Glu Ser Gly Phe Arg Val Asp Arg Leu Ser
    210                 215                 220

Gly Glu Ile Arg Leu Ser Gly Cys Leu Asp Tyr Glu Thr Ala Pro Gln
225                 230                 235                 240

Phe Thr Leu Leu Ile Arg Ala Arg Asp Cys Gly Glu Pro Ser Leu Ser
                245                 250                 255

Ser Thr Thr Thr Val His Val Asp Val Gln Glu Gly Asn Asn His Arg
        260                 265                 270

Pro Ala Phe Thr Gln Glu Asn Tyr Lys Val Gln Ile Pro Glu Gly Arg
    275                 280                 285

Ala Ser Gln Gly Val Leu Arg Leu Leu Val Gln Asp Arg Asp Ser Pro
290                 295                 300

Phe Thr Ser Ala Trp Arg Ala Lys Phe Asn Ile Leu His Gly Asn Glu
305                 310                 315                 320

Glu Gly His Phe Asp Ile Ser Thr Asp Pro Glu Thr Asn Glu Gly Ile
                325                 330                 335

Leu Asn Val Ile Lys Pro Leu Asp Tyr Glu Thr Arg Pro Ala Gln Ser
                340                 345                 350

Leu Ile Ile Val Val Glu Asn Glu Glu Arg Leu Val Phe Cys Glu Arg
            355                 360                 365

Gly Lys Leu Gln Pro Pro Arg Lys Ala Ala Ser Ala Thr Val Ser
370                 375                 380

Val Gln Val Thr Asp Ala Asn Asp Pro Pro Ala Phe His Pro Gln Ser
385                 390                 395                 400

Phe Ile Val Asn Lys Glu Gly Ala Arg Pro Gly Thr Leu Leu Gly
                405                 410                 415

Thr Phe Asn Ala Met Asp Pro Asp Ser Gln Ile Arg Tyr Glu Leu Val
                420                 425                 430

His Asp Pro Ala Asn Trp Val Ser Val Asp Lys Asn Ser Gly Val Val
                435                 440                 445

Ile Thr Val Glu Pro Ile Asp Arg Glu Ser Pro His Val Asn Asn Ser
    450                 455                 460

Phe Tyr Val Ile Ile His Ala Val Asp Asp Gly Phe Pro Pro Gln
465                 470                 475                 480

Thr Ala Thr Gly Thr Leu Met Leu Phe Leu Ser Asp Ile Asn Asp Asn
                485                 490                 495

Val Pro Thr Leu Arg Pro Arg Ser Arg Tyr Met Glu Val Cys Glu Ser
        500                 505                 510

Ala Val His Glu Pro Leu His Ile Glu Ala Glu Asp Pro Asp Leu Glu
        515                 520                 525

Pro Phe Ser Asp Pro Phe Thr Phe Glu Leu Asp Asn Thr Trp Gly Asn
    530                 535                 540

Ala Glu Asp Thr Trp Lys Leu Gly Arg Asn Trp Gly Gln Ser Val Glu
545                 550                 555                 560

Leu Leu Thr Leu Arg Ser Leu Pro Arg Gly Asn Tyr Leu Val Pro Leu
                565                 570                 575

Phe Ile Gly Asp Lys Gln Gly Leu Ser Gln Lys Gln Thr Val His Val
                580                 585                 590

Arg Ile Cys Pro Cys Ala Ser Gly Leu Thr Cys Val Glu Leu Ala Asp
```

```
                    595                 600                 605
Ala Glu Val Gly Leu His Val Gly Ala Leu Phe Pro Val Cys Ala Ala
            610                 615                 620

Phe Val Ala Leu Ala Val Ala Leu Leu Phe Leu Leu Arg Cys Tyr Phe
625                 630                 635                 640

Val Leu Glu Pro Lys Arg His Gly Cys Ser Val Ser Asn Asp Glu Gly
                645                 650                 655

His Gln Thr Leu Val Met Tyr Asn Ala Glu Ser Lys Gly Thr Ser Ala
            660                 665                 670

Gln Thr Trp Ser Asp Val Glu Gly Gln Arg Pro Ala Leu Leu Ile Cys
                675                 680                 685

Thr Ala Ala Gly Pro Thr Gln Gly Val Lys Asp Leu Glu Glu Val
            690                 695                 700

Pro Pro Ser Ala Ala Ser Gln Ser Ala Gln Ala Arg Cys Ala Leu Gly
705                 710                 715                 720

Ser Trp Gly Tyr Gly Lys Pro Phe Glu Pro Arg Ser Val Lys Asn Ile
                725                 730                 735

His Ser Thr Pro Ala Tyr Pro Asp Ala Thr Met His Arg Gln Leu Leu
            740                 745                 750

Ala Pro Val Glu Gly Arg Met Ala Glu Thr Leu Asn Gln Lys Leu His
            755                 760                 765

Val Ala Asn Val Leu Glu Asp Asp Pro Gly Tyr Leu Pro His Val Tyr
    770                 775                 780

Ser Glu Glu Gly Glu Cys Gly Gly Ala Pro Ser Leu Ser Ser Leu Ala
785                 790                 795                 800

Ser Leu Glu Gln Glu Leu Gln Pro Asp Leu Leu Asp Ser Leu Gly Ser
                805                 810                 815

Lys Ala Thr Pro Phe Glu Glu Ile Tyr Ser Glu Ser Gly Val Pro Ser
            820                 825                 830
```

CADHERIN 26 (CDH26)-FC FUSION PROTEINS AND METHODS OF USE THEREOF TO TREAT INFLAMMATORY CONDITIONS

CROSS-REFERENCE TO RELATED APPLICATION

This application is a national stage entry, filed under 35 U.S.C. § 371, of International Application No. PCT/US2016/034185, filed on May 25, 2016, which claims the benefit of U.S. Provisional Patent Application No. 62/168,087, filed May 29, 2015, the content of which is incorporated herein by reference in its entirety.

STATEMENT REGARDING FEDERALLY-SPONSORED RESEARCH

This invention was made with government support under U19 AI070235 and R01 DK076893, awarded by the National Institutes of Health. The government has certain rights in the invention.

FIELD OF THE INVENTION

The invention relates to cadherin based compounds and related compositions, and their use for treating inflammatory conditions.

BACKGROUND

Cadherin-mediated interactions between epithelial cells contribute to the maintenance of mucosal barriers that prevent access of environmental agents such as pathogens and allergens to underlying tissue and immunocytes. Several observations suggest a link between epithelial cadherin dysregulation, barrier disruption, and allergic disease. For example, reduced E-cadherin (CDH1) protein in asthmatic patients is associated with decreased airway epithelial barrier function (Trautmann et al., Apoptosis and loss of adhesion of bronchial epithelial cells in asthma. Int Arch Allergy Immunol. 2005; 138(2):142-50; de Boer W et al., Altered expression of epithelial junctional proteins in atopic asthma: possible role in inflammation. Can J Physiol Pharmacol. 2008; 86(3):105-12), and levels of membrane-localized CDH1 are decreased in the lesional skin of atopic dermatitis patients (Trautmann et al. The differential fate of cadherins during T-cell-induced keratinocyte apoptosis leads to spongiosis in eczematous dermatitis. J Invest Dermatol. 2001; 117(4):927-34). In addition to affecting barrier function, inhibition of CDH1 expression in vitro results in increased expression of the chemoattractant cytokine CCL17 by human bronchial epithelial cells (Heij ink I H, et al. Down-regulation of E-cadherin in human bronchial epithelial cells leads to epidermal growth factor receptor-dependent Th2 cell-promoting activity. J Immunol. 2007; 178(12):7678-85). Whether other cadherins influence allergic disease through impacting epithelial barrier maintenance or gene expression is not known.

In addition to homotypic interaction of cadherin molecules expressed by adjacent epithelial cells, cadherin-mediated interactions occur between epithelial cells and leukocytes. For example, CDH1 expressed by epithelial cells can bind CDH1 expressed by leukocytes or heterotypic molecules expressed by leukocytes such as integrins, in both cases influencing biological outcomes. However, reports of such epithelial cadherin/leukocyte integrin interactions are rare and to our knowledge limited to the observation that CDH1 binds lymphocyte integrin $\alpha E\beta 7$ and regulates the activation and localization of epidermal and intestinal intraepithelial lymphocytes (Cepek K L et al., Integrin alpha E beta 7 mediates adhesion of T lymphocytes to epithelial cells. J Immunol. 1993; 150(8 Pt 1):3459-70; Cepek K L et al., Adhesion between epithelial cells and T lymphocytes mediated by E-cadherin and the alpha E beta 7 integrin. Nature. 1994; 372(6502):190-3; Schon et al. Mucosal T lymphocyte numbers are selectively reduced in integrin alpha E (CD103)-deficient mice. J Immunol. 1999; 162(11):6641-9; Uchida et al. Role for E-cadherin as an inhibitory receptor on epidermal gammadelta T cells. J Immunol. 2011; 186(12):6945-54). Despite these observations regarding CDH1, the involvement of other cadherins in the regulation of immunologic processes mediated by the mucosal epithelium such as their binding to integrins has not been described.

A central feature of chronic allergic inflammation is T helper cell type 2 (Th2)-driven eosinophil accumulation typically mediated by an IL-13-driven cascade that elicits eosinophil trafficking from the blood to the tissue. This process involves the coordinate expression and activation of eosinophil-expressed selectins and integrins and their counter-receptors on activated endothelium, as well as the induction of eosinophil-activating chemokines such as the eotaxins (Broide D, and Sriramarao P. Eosinophil trafficking to sites of allergic inflammation. Immunological reviews. 2001; 179 163-72; Tachimoto et al. Cross-talk between integrins and chemokines that influences eosinophil adhesion and migration. Int Arch Allergy Immunol. 2002; 128 Suppl 1 18-20; Rosenberg et al. Eosinophil trafficking in allergy and asthma. J Allergy Clin Immunol. 2007; 119(6): 1303-10; quiz 11-2; Bochner B S. Road signs guiding leukocytes along the inflammation superhighway. J Allergy Clin Immunol. 2000; 106(5):817-28). While the mechanism of eosinophil transendothelial migration is well described, the processes involved in eosinophil transepithelial migration are not understood as completely. Moreover, much remains to be learned regarding the integrin/counter-receptor interactions occurring between epithelial cells and leukocytes and their consequences in the context of allergic inflammation.

The present inventors identified a previously uncharacterized cadherin, CDH26, that was markedly overexpressed in human gastrointestinal tissue with active eosinophilic inflammation. No studies of this molecule have been reported, although its transcript appears to be upregulated in epithelial cells under Th2-associated conditions (Woodruff et al. Genome-wide profiling identifies epithelial cell genes associated with asthma and with treatment response to corticosteroids. Proc Natl Acad Sci USA. 2007; 104(40): 15858-63; Shum et al. The adipocyte fatty acid-binding protein aP2 is required in allergic airway inflammation. J Clin Invest. 2006; 116(8):2183-92; Zhen et al. IL-13 and epidermal growth factor receptor have critical but distinct roles in epithelial cell mucin production. Am J Respir Cell Mol Biol. 2007; 36(2):244-53; Li R W, and Gasbarre L C. A temporal shift in regulatory networks and pathways in the bovine small intestine during *Cooperia oncophora* infection. Int J Parasitol. 2009; 39(7):813-24).

SUMMARY OF THE INVENTION

The present inventors sought to elucidate the function of CDH26 in allergic inflammation. As described in detail in the examples section, eosinophilic gastroenteropathy was used as a model system for allergic inflammation. The data presented in the examples confirm that CDH26 is a functional cadherin upregulated specifically during allergic responses and demonstrate that CDH26 affects epithelial gene expression and modulates leukocyte responses. The immunomodulatory activity of CDH26 is shown to be mediated through its regulation of leukocyte migration, adhesion, and activation via binding α4 and αE integrins. Moreover, T cell activation is inhibited by a CDH26-Fc fusion protein, which is shown here to have potent immunosuppressive activity. Since the fusion protein inhibits T cell activation, it may be useful in treating various diseases and disorders characterized by an underlying aberrant T cell activation.

In embodiments, the disclosure provides a fusion protein comprising two polypeptide segments, 1 and 2, segment 1 comprising or consisting of an extracellular region of the human cadherin 26 (CDH26) protein defined by EC1 (SEQ ID NO: 2), or fragment thereof, said fragment consisting of at least 3 contiguous amino acids of SEQ ID NO:2, and segment 2 comprising or consisting of a heavy chain constant region (Fc) of a human immunoglobulin (Ig) molecule.

In embodiments, segment 1 comprises or consists of SEQ ID NO: 10.

In embodiments, segment 1 comprises one or more additional extracellular cadherin repeat domains (EC) of human CDH26 selected from the group consisting of EC2, EC3, EC4, and EC5. In embodiments, the fragment of EC1 consists of from 20 to 90 or from 20 to 50 contiguous amino acids of SEQ ID NO: 2. In embodiments, segment 1 further comprises EC2 (SEQ ID NO: 3), or a contiguous amino acid fragment thereof, said fragment consisting of from 20 to 90 or from 20 to 50 contiguous amino acids of SEQ ID NO: 3. In embodiments, segment 1 further comprises EC3 SEQ ID NO: 4), or a contiguous amino acid fragment thereof, said fragment consisting of from 20 to 90 or from 20 to 50 contiguous amino acids of SEQ ID NO: 4. In embodiments, segment 1 comprises or consists of EC4 (SEQ ID NO: 5), or a contiguous amino acid fragment thereof, said fragment consisting of from 20 to 90 or from 20 to 50 contiguous amino acids of SEQ ID NO: 5. In embodiments, segment 1 comprises or consists of EC5 (SEQ ID NO: 6), or a contiguous amino acid fragment thereof, said fragment consisting of from 20 to 90 or from 20 to 50 contiguous amino acids of SEQ ID NO: 6.

In accordance with any of the embodiments above, the Ig molecule may be selected from the group consisting of IgG, IgE, IgM, IgD, IgA and IgY.

In embodiments, segment 1 comprises or consists of SEQ ID NO: 10 and the Ig molecule is selected from the group consisting of IgG, IgE, IgM, IgD, IgA and IgY.

In accordance with any of the embodiments above, the Ig molecule may be an IgG or IgA molecule. In embodiments, the IgG or IgA molecule is selected from the group consisting of IgG1, IgG2, IgG3, IgG4, IgA1 and IgA2. In embodiments, the Ig molecule is selected from the group consisting of IgG1, IgG4, IgA1 and IgA2. In embodiments, the Ig molecule is IgG1. In embodiments, segment 2 comprises or consists of SEQ ID NO: 7.

In accordance with any of the embodiments above, the fusion protein may further comprise a signal sequence or a linker sequence, or both. In embodiments, the signal sequence is selected from a signal peptide of any one of interleukin-2, CD5, immunoglobulin kappa light chain, trypsinogen, serum albumin, and prolactin, and functional fragments thereof. In embodiments, the linker sequence is located between segments 1 and 2 of the fusion protein. In embodiments, the linker sequence comprises or consists of from 2 to 10, or from 10 to 20, or from 20 to 50 amino acids. In embodiments, the fusion protein comprises or consists of SEQ ID NO: 8.

The disclosure also provides a composition or pharmaceutical composition comprising a fusion protein as described above or infra. In embodiments, the composition or pharmaceutical composition further comprises a pharmaceutically acceptable carrier or excipient. In embodiments, the composition or pharmaceutical composition is formulated for topical administration. In embodiments, the composition or pharmaceutical composition further comprises at least one additional active agent selected from an IL-13 inhibitor, a non-steroidal anti-inflammatory drug (NSAID), a cytokine inhibitor, an asthma medicine such as a bronchodilator, omalizumab, mepolizumab, or reslizumab, an immunosuppressive agent such as 6-mercaptopurine, or a steroid. In embodiments, the composition or pharmaceutical composition is for treating an inflammatory disease, disorder, or condition in a subject in need thereof.

The disclosure also provides modified fusion proteins which are modified relative to any of the fusion proteins described above or infra. In embodiments, the amino acid sequence of a modified fusion protein is from 90 to 99% identical to the unmodified sequence. In embodiments, the sequence of segment 1 is modified to alter one or more of integrin binding, glycosylation, or homodimer formation. In embodiments, the sequence of segment 2 is modified to improve the aqueous solubility, stability, avidity, and/or pharmacokinetics of the fusion protein. In embodiments, the sequence of segment 2 is modified to reduce complement binding or antibody dependent cytotoxicity. In accordance with any of the foregoing embodiments, the sequence is modified by one or more amino acid insertions, substitutions or deletions.

In embodiments, the present disclosure provides a CDH26-Fc fusion protein for treating an inflammatory disease, disorder, or condition in a subject in need thereof.

In embodiments, the disclosure provides methods of treating an inflammatory disease, disorder, or condition in a subject in need thereof, the methods comprising administering to the subject an amount of a cadherin 26 (CDH26)-based therapeutic agent. In embodiments, the CDH26-based therapeutic agent is administered in an amount effective to suppress T cell activation in target cells of the subject, thereby treating the inflammatory condition in the subject. In embodiments, the target cells are epithelial cells. In embodiments, the target cells are cells of a target tissue in the subject. In embodiments, the target tissue is skin, nasal, tracheal, lung, or esophageal tissue.

In embodiments, the CDH26-based therapeutic agent is effective to suppress a CDH26 activity in the cells of the subject, relative to untreated cells. In embodiments, the CDH26-based therapeutic agent is effective to suppress CDH26 gene expression or protein expression, or both. In embodiments, the amount of the CDH26-based therapeutic agent is effective to ameliorate one or more symptoms of the inflammatory disease, disorder, or condition.

In embodiments, the CDH26-based therapeutic agent is a CDH26-Fc fusion protein, a CDH26 anti-sense polynucleotide, a CDH26-directed miRNA, a CDH26-directed shRNA, or a CDH26-directed antibody.

In embodiments, the inflammatory condition is characterized by an interleukin 13 (IL-13) mediated inflammation. In embodiments, the inflammatory condition is an allergic inflammatory condition. In embodiments, the allergic inflammatory condition is selected from asthma, atopic dermatitis, allergic rhinitis, eosinophilic duodenitis, eosinophilic colitis, eosinophilic gastritis (EG), and eosinophilic esophagitis (EoE). In embodiments, the inflammatory condition is associated with an autoimmune disease or disorder. In embodiments, the inflammatory condition is associated with an infection, for example a viral or bacterial infection. In embodiments, the inflammatory condition is associated with a cancer.

In embodiments, the methods of treating an inflammatory disease, disorder, or condition described herein further comprise administering to the subject at least one additional active agent. In embodiments, the at least one additional active agent is an anti-inflammatory agent. In embodiments, the at least one additional active agent is an IL-13 inhibitor, a non-steroidal anti-inflammatory drug (NSAID), an asthma medicine such as a bronchodilator, omalizumab, mepolizumab, or reslizumab, an immunosuppressive agent such as 6-mercaptopurine, a cytokine inhibitor, or a steroid.

The disclosure also provides methods of treating eosinophilic esophagitis (EoE) or eosinophilic gastritis (EG) in a subject in need thereof, comprising administering to the subject an amount of a (CDH26)-based therapeutic agent. In embodiments, the CDH26-based therapeutic agent is a CDH26-Fc fusion protein, a CDH26 anti-sense polynucleotide, a CDH26-directed miRNA, a CDH26-directed shRNA, or a CDH26-directed antibody.

The disclosure also provides methods of suppressing CDH26 activity in a cell, the method comprising contacting the cell with an anti-CDH26 agent in an amount effective to suppress CDH26 expression in the cell.

BRIEF DESCRIPTION OF THE DRAWINGS

FIGS. 7A-7D: Effect of CDH26-Fc on CD4+ T cell activation. Human peripheral blood CD4+ T cells were isolated and cultured for 48 h in wells coated with the indicated amounts of proteins (IgG, anti-CD3, VCAM-1-Fc, and/or CDH26-Fc). Cells were stained for flow cytometry analysis to detect CD4, CD25, CD69, and CD154, and supernatants were analyzed to detect IL-2 and IL-4 levels by ELISA. For (A-C, top), the percent of live CD4+ cells that are (A) CD25+, (B) CD69+, or (C) CD154+ are shown, and for (A-C, bottom), the mean fluorescence intensity of (A) CD25, (B) CD69, or (C) CD154 signal for CD4+ cells is shown. For (D), the amount of (top) hIL-2 and (bottom) hIL-4 detected in the supernatant is shown. The dotted lines represent the detection limit for each ELISA.

FIG. 8 Nucleotide sequence of human CDH26-hIgG1-Fc (SEQ ID NO: 9). Specific regions of the sequence are underlined and denoted by superscript numbers at the end of the denoted underlined sequence. The indicated nucleotides encode the amino acids that compose the following domains of the protein: (1) signal peptide, (2) extracellular cadherin repeat domain 1 (EC1), (3) extracellular cadherin repeat domain 2 (EC2), (4) extracellular cadherin repeat domain 3 (EC3), (5) extracellular cadherin repeat domain 4 (EC4), (6) extracellular cadherin repeat domain 5 (EC5), (7) human IgG1-Fc.

FIG. 9: Primary amino acid sequence of a human CDH26-hIgG1-Fc fusion protein (SEQ ID NO: 8). Specific regions of the sequence are underlined and denoted by superscript numbers at the end of the denoted underlined sequence. The indicated amino acids form the following domains of the protein: (1) signal peptide, (2) extracellular cadherin repeat domain 1 (EC1), (3) extracellular cadherin repeat domain 2 (EC2), (4) extracellular cadherin repeat domain 3 (EC3), (5) extracellular cadherin repeat domain 4 (EC4), (6) extracellular cadherin repeat domain 5 (EC5), (7) human IgG1-Fc.

DETAILED DESCRIPTION OF THE INVENTION

Figure 1A:
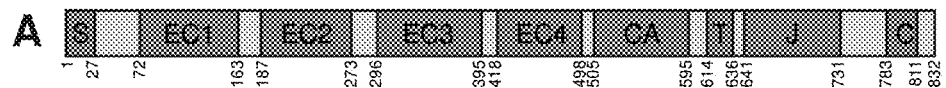
FIGS. 1A-1D: Biochemical analysis of CDH26. (A) Schematic representing human CDH26 domain structure. S: signal peptide, EC1-EC4: extracellular cadherin repeat 1-4, CA: cadherin domain, T: transmembrane domain, J: juxtamembrane domain, C: catenin binding domain. (B and C) Surface biotinylation of TE-7 (B) and NCI-N87 (C) cells. Cell surface proteins were labeled with biotin and pulled down with streptavidin beads. Total cell lysates (input) and proteins bound to the streptavidin beads were subjected to SDS-PAGE and western blot analysis. Predicted CDH26 molecular weight: 92.4 kDa. (D) Immunoprecipitates from transiently transfected HEK 293T cells were treated with either peptide: N-glycosidase F (PNGase F) (+) or heat-inactivated PNGase F (−). Inputs (1/10 of amount used for IP) and treated immunoprecipitates were subjected to SDS-PAGE and western blot analysis.
Figure 1B:
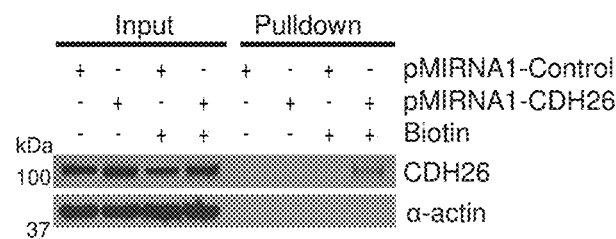
Figure 1C:
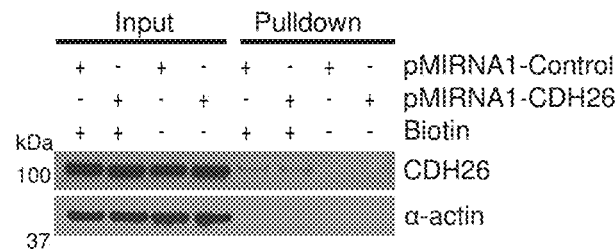
Figure 1D:
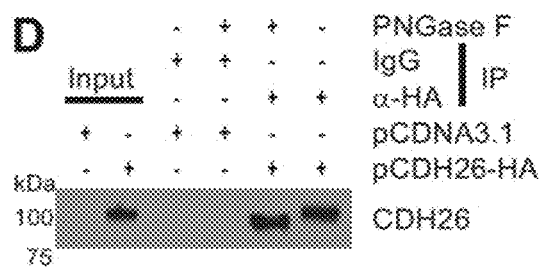

Previous work by the inventors established a biological connection between high levels of CDH26 expression and the behavior of the inflammatory cells that underlie the inflammatory condition eosinophilic gastritis (EG) (WO 2012/178188). As discussed in more detail infra, the inventors have extended this work to show that CDH26 affects epithelial gene expression, binds α4 and αE integrins, and regulates leukocyte migration and activation. Importantly, the present disclosure further demonstrates that a CDH26-Fc fusion protein acts as an immunosuppressive agent in a model system of T cell activation which is relevant to allergic inflammation.

The present disclosure provides CDH26-based therapeutic agents for the treatment of an inflammatory condition. In embodiments, the CDH26-based therapeutic agent is effective to suppress T cell activation, especially CD4+ T cell activation. In embodiments, the agent suppresses T cell activation in a target cell or tissue. In embodiments, the agent suppresses T cell activation in an in vitro assay, such as a T cell activation assay.

In embodiments, the CDH26-based therapeutic agent is a CDH26-Fc fusion protein, a CDH26 anti-sense polynucleotide, a CDH26-directed miRNA, a CDH26-directed shRNA, or a CDH26-directed antibody, including a humanized antibody. In embodiments, the CDH26-based therapeutic agent is a fusion protein, as discussed in more detail below.

The present disclosure also provides methods for treating an inflammatory condition in a subject by modulating CDH26 activity, and related methods. The methods comprise administering a CDH26-based therapeutic agent to a subject in need of treatment for an inflammatory condition.

CDH26 Fusion Proteins

The present disclosure provides CDH26 fusion proteins comprising two polypeptide segments, denoted 1 and 2. Segment 1 consists of a polypeptide comprising a CDH26 extracellular region. Segment 2 consists of a polypeptide comprising a heavy chain constant region (Fc) of a human immunoglobulin (Ig) molecule. The term "fusion protein" in this context refers to a polypeptide comprising the polypeptide segments 1 and 2, and one or more additional, optional polypeptides. For example, the fusion protein may contain an optional polypeptide that functions as a signal sequence, also referred to as a signal peptide (these terms are used interchangeably herein). Exemplary signal sequences include the signal peptides of interleukin-2, CD5, immunoglobulin kappa light chain, trypsinogen, serum albumin, and prolactin, which are known in the art. The fusion protein may also contain an optional polypeptide that functions as a linker sequence joining segments 1 and 2 together. In embodiments, the linker sequence comprises or consists of from 2 to 10, or from 5 to 10, or from 10 to 25 amino acids. In embodiments the linker is selected from a flexible linker and a rigid linker. In embodiments, the linker is a cleavable linker, e.g., one that can be cleaved in vivo by an endogenous enzyme. Exemplary linkers are known in the art and are reviewed, for example, in Chen et al., 2013, Adv Drug Deliv Rev.

In embodiments, segment 1 comprises or consists of the CDH26 extracellular region defined by amino acids 1-608 of the human CDH26 protein (SEQ ID NO: 11). In embodiments, segment 1 comprises or consists of the CDH26 extracellular region defined by amino acids asparagine 55 (Asp55) to serine 599 (Ser599) (SEQ ID NO: 10) of the human CDH26 protein. In embodiments, segment 1 comprises one or more of amino acids 609-613 of the human CDH26 protein.

In embodiments, segment 1 comprises or consists of one or more CDH26 extracellular domains selected from the group consisting of extracellular cadherin repeat domain (EC) 1, EC2, EC3, EC4, and EC5 of the human CDH26 protein (SEQ ID NO: 11). In embodiments, segment 1 comprises at least EC1 (SEQ ID NO: 2). In embodiments, segment 1 comprises or consists of (SEQ ID NO: 2). In embodiments, segment 1 comprises or consists of EC1 (SEQ ID NO: 2) and at least one of EC2 (SEQ ID NO: 3), EC3 (SEQ ID NO: 4), and EC4 (SEQ ID NO: 5). In embodiments, segment 1 comprises or consists of EC1 (SEQ ID NO: 2) and at least two of EC2 (SEQ ID NO: 3), EC3 (SEQ ID NO: 4), and EC4 (SEQ ID NO: 5). In embodiments, segment 1 comprises or consists of EC1 (SEQ ID NO: 2) and all three of EC2 (SEQ ID NO: 3), EC3 (SEQ ID NO: 4), and EC4 (SEQ ID NO: 5). In embodiments, segment 1 comprises or consists of each of the five EC domains of CDH26 (SEQ ID Nos 2-6).

In embodiments, segment 2 comprises or consists of the Fc region of an Ig molecule. The term "Fc" refers to "fragment crystallizable", the part of an antibody molecule that interacts with Fc receptors which are cell surface and intracellular molecules that bind to the Fc region of antibodies. The Fc region contains the carboxy-terminal heavy chains of the antibody molecule disulfide bonded to each other through the hinge region.

In embodiments, the Ig molecule is a human Ig molecule selected from the group consisting of IgG, IgE, IgM, IgD, IgA and IgY.

In embodiments, the human Ig molecule is an IgG or IgA molecule. In embodiments, the IgG or IgA molecule is selected from the group consisting of IgG1, IgG2, IgG3, IgG4, IgA1 and IgA2. In embodiments, the Ig molecule is selected from the group consisting of IgG1, IgG4, IgA1 and IgA2.

In embodiments, the Fc polypeptide of segment 2 is comprises or consists of SEQ ID NO: 7.

Modifications

In embodiments, the polypeptide of a fusion protein described herein may be modified by one or more amino acid insertions, substitutions or deletions, for example in order to alter the stability or biological activity of the fusion protein.

In embodiments, the polypeptide of segment 1 is modified by one or more amino acid insertions, substitutions or deletions for example, to alter integrin binding, glycosylation, or homodimer formation, as described in more detail below.

In embodiments, the Fc polypeptide of segment 2 is modified by one or more amino acid insertions, substitutions or deletions, for example, to improve the aqueous solubility, stability, avidity, and/or pharmacokinetics of the CDH26-Fc fusion protein. In embodiments, the Fc polypeptide of segment 2 is modified to reduce or eliminate complement binding or antibody dependent cellular cytotoxicity, or both. In some embodiments, the Fc polypeptide is modified to improve the aqueous solubility and stability of the fusion protein, or to promote its purification during manufacturing. In embodiments, the Fc polypeptide is modified to polymerize, e.g., through engineered disulfide bridges and carboxy-terminal extensions, thereby increasing the avidity of the fusion protein. In embodiments, the Fc polypeptide is modified to improve the pharmacokinetics of the fusion protein, e.g., to improve its in vivo half-life. Examples of such Fc modifications are known in the art and described, for example in Czajkowsky et al. (2012) Fc-fusion proteins: new developments and future perspectives in EMBO Molecular Medicine.

In embodiments, the amino acids inserted or substituted in the polypeptide of segment 1 and/or segment 2 of a fusion protein described herein are naturally occurring amino acids selected from the group consisting of: alanine (Ala, A); arginine (Arg, R); asparagine (Asn, N); aspartic acid (Asp, D); cysteine (Cys, C); glutamine (Gln, Q); glutamic acid (Glu, E); glycine (Gly, G); histidine (His, H); Isoleucine (Ile, I): leucine (Leu, L); lysine (Lys, K); methionine (Met, M); phenylalanine (Phe, F); proline (Pro, P): serine (Ser, S); threonine (Thr, T); tryptophan (Trp, W); tyrosine (Tyr, Y); and valine (Val, V). In embodiments, the amino acids inserted or substituted are naturally or non-naturally occurring amino acids. A non-naturally occurring amino acids refers to an amino acid other than those listed above, which is able to covalently bind adjacent amino acids to form a polypeptide chain. Examples of non-naturally occurring amino acid residues include norleucine, ornithine, norvaline, and homoserine.

In embodiments, the polypeptide of segment 1 or segment 2, or both, is modified by a conservative or non-conservative amino acid substitution. A conservative amino acid substitution refers to substituting an amino acid with another amino acid in the same chemical class. A non-conservative amino acid substitution refers to substituting an amino acid with another amino acid having different chemical and/or physical (e.g., in terms of size or bulkiness) properties. Amino acids are generally classified according to the chemical and physical properties of their side chains, for example by hydrophobicity, acidity, basicity, polarity, large or small. Generally included among the hydrophobic amino acids are norleucine, methionine, alanine, valine, leucine, and isoleucine. Generally classified as neutral and large nonpolar are isoleucine, leucine, valine, methionine, and phenylalanine; generally classified as neutral and small nonpolar are alanine and threonine; generally classified as neutral and small polar are glycine, serine, and asparagine; generally classified as neutral and intermediate or large polar are proline, tyrosine, glutamine, and tryptophan; generally classified as acidic are aspartic acid and glutamic acid; generally classified as basic are arginine and lysine, and generally classified as weakly basic are histidine and cysteine.

In embodiments, the one or more amino acid insertions, substitutions or deletions in segment 1 is relative to the amino acid sequence of one or more of SEQ ID NOs: 2-6. In embodiments, the one or more amino acid insertions, substitutions or deletions in segment 2 is relative to the amino acid sequence of SEQ ID NO: 7.

In embodiments, one or more amino acid residues in segment 1 is substituted with a non-conservative amino acid in order to change the activity of the fusion protein, for example, to alter the binding of the fusion protein to an integrin, reduce the formation of CDH26-Fc homodimers with other CDH26 molecules, or change the glycosylation of the fusion protein. In this context, a non-conservative amino acid substitution refers to one which would be expected to abolish the functionality of the amino acid residue it replaces. For example, an acidic residue is needed for integrin binding. Accordingly, a non-conservative amino acid substitution at a residue which functions in integrin binding would be the substitution of an acidic residue with a residue that is not acidic.

In embodiments, segment 1 comprises or consists of EC1 (SEQ ID NO: 2) and the one or more amino acid residues in segment 1 that is modified as discussed above is selected from the group consisting of the amino acids corresponding to W56, N81, N85, D98, E99, E102, E138, N171, N177 and N462 of CDH26 (SEQ ID NO:11). In this context, "corresponding to" means the amino acid residues in segment 1 of the fusion protein that map to the indicated residues in SEQ ID NO:11 when the amino acid sequences of segment 1 and the EC1 of CDH26 (SEQ ID NO:11) are aligned.

In embodiments, the one or more amino acid residues is selected from the group consisting of the amino acids corresponding to N85, D98, E99, E102 and E138 of CDH26 (SEQ ID NO:11) and the amino acid substitution is effective to enhance or reduce the binding of the fusion protein to an integrin molecule. For example, mutation of any one of these amino acid residues to alanine would be expected to reduce integrin binding. Mutation of N85 to aspartic acid or glutamic acid might be expected to enhance integrin binding. Mutation of any one of these residues to another negatively charged amino acid (i.e. aspartic acid or glutamic acid) might be expected to maintain similar integrin binding or to enhance integrin binding.

In embodiments, the amino acid residue is that corresponding to W56 of CDH26 (SEQ ID NO:11) and the amino acid substitution is effective to reduce the formation of CDH26-Fc homodimers in trans with other CDH26 molecules. For example, mutation of W56 to alanine would be expected to reduce homodimer formation.

In embodiments, the one or more of the amino acid residues is selected from the group consisting of the amino acids corresponding to N81, N85, N171, N177 and N462 of CDH26 (SEQ ID NO:11) and the amino acid substitution is effective to prevent glycosylation. For example, mutation of any one of these residues to alanine would be expected to prevent glycosylation.

In embodiments, the signal peptide of a fusion protein described herein comprises or consists of the endogenous signal peptide of CDH26, which is amino acids 1-27 of SEQ ID NO: 11. In embodiments, the signal peptide comprises or consists of the signal peptide of a molecule selected from the group consisting of interleukin-2, CD5, immunoglobulin kappa light chain, trypsinogen, serum albumin, and prolactin. These peptides are known in the art to enhance protein secretion and are described, for example, in Dalton and Barton 2014 Protein Science.

Table 1 below shows the key sequences of an exemplary CDH26-Fc fusion protein. Shown are (1) signal peptide, (2) extracellular cadherin repeat domain 1 (EC1), (3) EC2, (4) EC3, (5) EC4, (6) EC5, and (7) human IgG1-Fc. The complete annotated amino acid sequence of the exemplary fusion protein (SEQ ID NO: 8) is shown in FIG. 9 and the complete annotated nucleotide sequence (SEQ ID NO: 9) is shown in FIG. 8.

TABLE 1

Key sequences of an exemplary CDH26-Fc fusion protein

| SEQ ID NO | Designation | Amino acid sequence |
|---|---|---|
| 1 | signal | MAMRSGRHPSLLLLLVLLLWLLQVSII |
| 2 | EC1 | PKLIGELFNNMSYNMSLMYLISGPGVDEYPEIGLFSLEDHENG RIYVHRPVDREMTPSFTVYFDVVERSTGKIVDTSLIFNIRISDV NDHAP |
| 3 | EC2 | QMLAVDLDEENTPNSQVLYFLISQTPLLKESGFRVDRLSGEIR LSGCLDYETAPQFTLLIRARDCGEPSLSSTTTVHVDVQEGNN HRP |
| 4 | EC3 | LLVQDRDSPFTSAWRAKFNILHGNEEGHFDISTDPETNEGILN VIKPLDYETRPAQSLIIVVENEERLVFCERGKLQPPRKAAASAT VSVQVTDANDPPAF |
| 5 | EC4 | FNAMDPDSQIRYELVHDPANWVSVDKNSGVVITVEPIDRESP HVNNSFYVIIIHAVDDGFPPQTATGTLMLFLSDINDNVP |
| 6 | EC5 | RYMEVCESAVHEPLHIEAEDPDLEPFSDPFTFELDNTWGNAE DTWKLGRNWGQSVELLTLRSLPRGNYLVPLFIGDKQGLSQK QVHVRIC |
| 7 | Fc | DKTHTCPPCPAPELLGGPSVFLFPPKPKDTLMISRTPEVTCVV VDVSHEDPEVKFNWYVDGVEVHNAKTKPREEQYNSTYRVV SVLTVLHQDWLNGKEYKCKVSNKALPAPIEKTISKAKGQPRE PQVYTLPPSREEMTKNQVSLTCLVKGFYPSDIAVEWESNGQP ENNYKTTPPVLDSDGSFFLYSKLTVDKSRWQQGNVFSCSVM HEALHNHYTQKSLSLSPGK |

Methods of Use

The present disclosure provides methods for the treatment of an inflammatory condition in a subject in need thereof by administering to the subject an effective amount of a CDH26-based therapeutic agent. In embodiments, the effective amount is a therapeutically effective amount. In embodiments, the effective amount is the amount effective to ameliorate one or more symptoms of the inflammatory condition. In embodiments, the effective amount is the amount effective to reduce the inflammatory response underlying the allergic reaction of the inflammatory condition, thereby treating the inflammatory condition. In embodiments, the inflammatory response is reduced in cells of a target tissue affected by an inflammatory condition. In embodiments, the tissue is skin tissue, esophageal tissue, nasal tissue, tracheal tissue, or lung tissue, such as tissue of the bronchi or bronchioles.

In embodiments, the inflammatory condition is characterized by an interleukin 13 (IL-13) mediated allergic inflammation. In embodiments, the inflammatory condition is asthma, atopic dermatitis, allergic rhinitis, eosinophilic gastritis (EG), or eosinophilic esophagitis (EoE).

The present disclosure also provides methods comprising combination therapy for the treatment of inflammatory condition. As used herein, "combination therapy" or "cotherapy" includes the administration of an effective amount of a CDH26-based therapeutic agent as part of a specific treatment regimen intended to provide the beneficial effect from the co-action of the CDH26-based therapeutic agent and an additional active agent, e.g., an additional active pharmaceutical ingredient (API). The beneficial effect of the combination includes, but is not limited to, pharmacokinetic or pharmacodynamic co-action resulting from the combination of therapeutic compounds. The beneficial effect of the combination may also relate to the mitigation of a toxicity, side effect, or adverse event associated with another agent in the combination. "Combination therapy" is not intended to encompass the administration of two or more of these therapeutic compounds as part of separate monotherapy regimens that incidentally and arbitrarily result in a beneficial effect that was not intended or predicted.

In embodiments, at least one additional active agent is administered in combination therapy with a CDH26-based therapeutic agent described herein. In embodiments, the additional active agent may be a therapeutic agent, for example an anti-inflammatory agent, or a non-therapeutic agent, and combinations thereof. With respect to therapeutic agents, the beneficial effect of the combination includes, but is not limited to, pharmacokinetic or pharmacodynamic co-action resulting from the combination of therapeutically active compounds. With respect to nontherapeutic agents, the beneficial effect of the combination may relate to the mitigation of a toxicity, side effect, or adverse event associated with a therapeutically active agent in the combination.

In embodiments, the at least one additional active agent is an anti-inflammatory agent selected from an IL-13 inhibitor, a non-steroidal anti-inflammatory drug (NSAID), a steroid, and a cytokine inhibitor.

In one embodiment, the at least one additional agent is a non-therapeutic agent which mitigates one or more side effects of the CDH26-based therapeutic agent in the composition, or which mitigates one or more side effects of the at least one additional active agent in the composition.

In the context of combination therapy, the administration of the CDH26-based therapeutic agent may be simultaneous with or sequential to the administration of the one or more additional active agents. In another embodiment, administration of the different components of a combination therapy may be at different frequencies. The one or more additional agents may be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a compound of the present disclosure.

The one or more additional active agents can be formulated for co-administration with the CDH26-based therapeutic agent in a single dosage form. The one or more additional active agents can be administered separately from the dosage form that comprises the CDH26-based therapeutic agent. When the additional active agent is administered separately from the CDH26-based therapeutic agent, it can be by the same or a different route of administration as the CDH26-based therapeutic agent.

Preferably, the administration of a composition comprising the CDH26-based therapeutic agent in combination with one or more additional active agents provides a synergistic response in the subject being treated. In this context, the term "synergistic" refers to the efficacy of the combination being more effective than the additive effects of either single therapy alone. The synergistic effect of a combination therapy according to the disclosure can permit the use of lower dosages and/or less frequent administration of at least one agent in the combination compared to its dose and/or frequency outside of the combination. Additional beneficial effects of the combination can be manifested in the avoidance or reduction of adverse or unwanted side effects associated with the use of either therapy in the combination alone (also referred to as monotherapy).

"Combination therapy" also embraces the administration of the compounds of the present disclosure in further combination with non-drug therapies (e.g., surgery or radiation treatment). Where the combination therapy further comprises a non-drug treatment, the non-drug treatment may be conducted at any suitable time so long as a beneficial effect from the co-action of the combination of the therapeutic compounds and non-drug treatment is achieved. For example, in appropriate cases, the beneficial effect is still achieved when the non-drug treatment is temporally removed from the administration of the therapeutic compounds, perhaps by days or even weeks.

In embodiments, the amount of the CDH26-based therapeutic agent administered to the subject is a therapeutically effective amount. The term "therapeutically effective amount" refers to an amount sufficient to treat, ameliorate a symptom of, reduce the severity of, or reduce the duration of the disease or disorder being treated or enhance or improve the therapeutic effect of another therapy, or sufficient to exhibit a detectable therapeutic effect in the subject.

An effective amount of the CDH26-based therapeutic agent can be administered once or twice daily, from two to five times daily, up to two times or up to three times daily, or up to eight times daily.

In accordance with the methods described herein, a "subject in need thereof" is a subject having an inflammatory disease, disorder, or condition, or a subject having an increased risk of developing an inflammatory disease, disorder, or condition relative to the population at large. The subject in need thereof can be one that is "non-responsive" or "refractory" to a currently available therapy. In this context, the terms "non-responsive" and "refractory" refer to the subject's response to therapy as not clinically adequate to relieve one or more symptoms associated with the inflammatory disease, disorder, or condition. In one aspect of the methods described here, the subject in need thereof is a subject having an inflammatory disease, disorder, or condition that is refractory to standard therapy.

A "subject" includes a mammal. The mammal can be any mammal, for example, a human, primate, vertebrate, bird, mouse, rat, fowl, dog, cat, cow, horse, goat, camel, sheep or a pig. Preferably, the mammal is a human. The term "patient" refers to a human subject.

The present disclosure also provides a monotherapy for the treatment of inflammatory disease, disorder, or condition as described herein. As used herein, "monotherapy" refers to the administration of a single active or therapeutic compound, e.g., an CDH26-based therapeutic agent, to a subject in need thereof.

As used herein, "treatment", "treating" or "treat" describes the management and care of a patient for the purpose of combating a disease, condition, or disorder and includes the administration of an CDH26-based therapeutic agent to alleviate the symptoms or complications of the inflammatory disease, disorder, or condition.

As used herein, "prevention", "preventing" or "prevent" describes reducing or eliminating the onset of the symptoms or complications of the inflammatory disease, disorder, or condition and includes the administration of an CDH26-based therapeutic agent to reduce the onset, development or recurrence of symptoms of the disease, disorder, or condition.

In one embodiment, the administration of a CDH26-based therapeutic agent leads to the elimination of a symptom or complication of the inflammatory disease, disorder, or condition being treated, however elimination of the disease, disorder, or condition is not required. In one embodiment, the severity of the symptom is decreased.

Pharmaceutical Compositions and Formulations

The present disclosure provides pharmaceutical compositions comprising an amount of a CDH26-based therapeutic agent.

In one embodiment, the CDH26-based therapeutic agent is combined with at least one additional active agent in a single dosage form. In embodiments, the at least one additional active agent is selected from an anti-inflammatory agent selected from an IL-13 inhibitor, a non-steroidal anti-inflammatory drug (NSAID), a steroid, an asthma medicine such as a bronchodilator, omalizumab, mepolizumab, or reslizumab, an immunosuppressive agent such as 6-mercaptopurine, and a cytokine inhibitor, and combinations thereof.

A "pharmaceutical composition" is a formulation containing a CDH26-based therapeutic agent in a pharmaceutically acceptable form suitable for administration to a subject. The term subject is used in the same context as note above, namely to refer to a mammal, for example, a human, primate, vertebrate, bird, mouse, rat, fowl, dog, cat, cow, horse, goat, camel, sheep or a pig. Preferably, the subject is a human subject, and most preferably a human in need of treatment for an inflammatory condition. The term "patient" refers to a human subject who has been diagnosed or is otherwise under the care of a medical professional. The phrase "pharmaceutically acceptable" refers to those compounds, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. Examples of pharmaceutically acceptable excipients include, without limitation, sterile liquids, water, buffered saline, ethanol, polyol (for example, glycerol, propylene glycol, liquid polyethylene glycol and the like), oils, detergents, suspending agents, carbohydrates (e.g., glucose, lactose, sucrose or dextran), antioxidants (e.g., ascorbic acid or glutathione), chelating agents, low molecular weight proteins, or suitable mixtures thereof.

A pharmaceutical composition can be provided in bulk or in dosage unit form. It is especially advantageous to formulate pharmaceutical compositions in dosage unit form for ease of administration and uniformity of dosage. The term "dosage unit form" as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the disclosure are dictated by and directly dependent on the unique characteristics of the active compound and the particular therapeutic effect to be achieved. A dosage unit form can be an ampoule, a vial, a suppository, a dragee, a tablet, a capsule, an IV bag, or a single pump on an aerosol inhaler.

In therapeutic applications, the dosages vary depending on the agent, the age, weight, and clinical condition of the recipient subject or patient, and the experience and judgment of the clinician or practitioner administering the therapy, among other factors affecting the selected dosage. Generally, the dose should be a therapeutically effective amount. Dosages can be provided in mg/kg/day units of measurement (which dose may be adjusted for the patient's weight in kg, body surface area in m2, and age in years). An effective amount of a pharmaceutical composition is that which provides an objectively identifiable improvement as noted by the clinician or other qualified observer. For example, alleviating a symptom of a disorder, disease or condition. As used herein, the term "dosage effective manner" refers to amount of a pharmaceutical composition to produce the desired biological effect in a subject or cell.

For example, the dosage unit form can comprise 1 nanogram to 2 milligrams, or 0.1 milligrams to 2 grams; or from 10 milligrams to 1 gram, or from 50 milligrams to 500 milligrams or from 1 microgram to 20 milligrams; or from 1 microgram to 10 milligrams; or from 0.1 milligrams to 2 milligrams.

The pharmaceutical compositions can take any suitable form (e.g. liquids, aerosols, solutions, inhalants, mists, sprays; or solids, powders, ointments, pastes, creams, lotions, gels, patches and the like) for administration by any desired route (e.g. pulmonary, inhalation, intranasal, oral, buccal, sublingual, parenteral, subcutaneous, intravenous, intramuscular, intraperitoneal, intrapleural, intrathecal, transdermal, transmucosal, rectal, and the like). For example, a pharmaceutical composition of the disclosure may be in the form of an aqueous solution or powder for aerosol administration by inhalation or insufflation (either through the mouth or the nose), in the form of a tablet or capsule for oral administration; in the form of a sterile aqueous solution or dispersion suitable for administration by either direct injection or by addition to sterile infusion fluids for intravenous infusion; or in the form of a lotion, cream, foam, patch, suspension, solution, or suppository for transdermal or transmucosal administration.

In embodiments, the pharmaceutical composition is in a form suitable for topical administration. For example, the composition may be formulated as a gel or cream using suitable excipients. In embodiments, the composition may be formulated as an aqueous, aqueous/alcoholic or oily solution; a dispersion of the lotion or serum type; an anhydrous or lipophilic gel; an emulsion of liquid or semi-liquid consistency, for example of the type that are obtained by dispersion of a fatty phase in an aqueous phase; or a suspension or emulsion of smooth, semi-solid or solid consistency of the cream or gel type. In embodiments, the composition may comprise one or more of a thickener, a coloring agent, an emollient, a skin moisturizing agent, an emulsifier, a fragrance, an anti-microbial agent, a sunscreen, a pH modulator, and a preservative. A thickener may be present in amounts anywhere from about 0.1% or less to about 20% or more by weight, such as from about 0.5% to about 10% by weight of the composition. Exemplary thickeners may be cross-linked polyacrylate materials available under the trademark Carbopol. Gums may be employed such as xanthan, carrageenan, gelatin, karaya, pectin and locust beans gum. Under certain circumstances the thickening function may be accomplished by a material also serving as a silicone or emollient. For instance, silicone gums in excess of 10 centistokes and esters such as glycerol stearate have dual functionality.

A pharmaceutical composition can be in the form of an orally acceptable dosage form including, but not limited to, capsules, tablets, buccal forms, troches, lozenges, and oral liquids in the form of emulsions, aqueous suspensions, dispersions or solutions. Capsules may contain mixtures of a compound of the present disclosure with inert fillers and/or diluents such as the pharmaceutically acceptable starches (e.g., corn, potato or tapioca starch), sugars, artificial sweetening agents, powdered celluloses, such as crystalline and microcrystalline celluloses, flours, gelatins, gums, etc. In the case of tablets for oral use, carriers which are commonly used include lactose and corn starch. Lubricating agents, such as magnesium stearate, can also be added. For oral administration in a capsule form, useful diluents include lactose and dried corn starch. When aqueous suspensions and/or emulsions are administered orally, the compound of the present disclosure may be suspended or dissolved in an oily phase is combined with emulsifying and/or suspending agents. If desired, certain sweetening and/or flavoring and/or coloring agents may be added.

A pharmaceutical composition can be in the form of a tablet. The tablet can comprise a unit dosage of a compound of the present disclosure together with an inert diluent or carrier such as a sugar or sugar alcohol, for example lactose, sucrose, sorbitol or mannitol. The tablet can further comprise a non-sugar derived diluent such as sodium carbonate, calcium phosphate, calcium carbonate, or a cellulose or derivative thereof such as methyl cellulose, ethyl cellulose, hydroxypropyl methyl cellulose, and starches such as corn starch. The tablet can further comprise binding and granulating agents such as polyvinylpyrrolidone, disintegrants (e.g. swellable crosslinked polymers such as crosslinked carboxymethylcellulose), lubricating agents (e.g. stearates), preservatives (e.g. parabens), antioxidants (e.g. BHT), buffering agents (for example phosphate or citrate buffers), and effervescent agents such as citrate/bicarbonate mixtures.

The tablet can be a coated tablet. The coating can be a protective film coating (e.g. a wax or varnish) or a coating designed to control the release of the active agent, for example a delayed release (release of the active after a predetermined lag time following ingestion) or release at a particular location in the gastrointestinal tract. The latter can be achieved, for example, using enteric film coatings such as those sold under the brand name Eudragit®.

Tablet formulations may be made by conventional compression, wet granulation or dry granulation methods and utilize pharmaceutically acceptable diluents, binding agents, lubricants, disintegrants, surface modifying agents (including surfactants), suspending or stabilizing agents, including, but not limited to, magnesium stearate, stearic acid, talc, sodium lauryl sulfate, microcrystalline cellulose, carboxymethylcellulose calcium, polyvinylpyrrolidone, gelatin, alginic acid, acacia gum, xanthan gum, sodium citrate, complex silicates, calcium carbonate, glycine, dextrin, sucrose, sorbitol, dicalcium phosphate, calcium sulfate, lactose, kaolin, mannitol, sodium chloride, talc, dry starches and powdered sugar. Preferred surface modifying agents include nonionic and anionic surface modifying agents. Representative examples of surface modifying agents include, but are not limited to, poloxamer 188, benzalkonium chloride, calcium stearate, cetostearyl alcohol, cetomacrogol emulsifying wax, sorbitan esters, colloidal silicon dioxide, phosphates, sodium dodecylsulfate, magnesium aluminum silicate, and triethanolamine.

A pharmaceutical composition can be in the form of a hard or soft gelatin capsule. In accordance with this formulation, the compound of the present disclosure may be in a solid, semi-solid, or liquid form.

A pharmaceutical composition can be in the form of a sterile aqueous solution or dispersion suitable for parenteral administration. The term parenteral as used herein includes subcutaneous, intracutaneous, intravenous, intramuscular, intra-articular, intraarterial, intrasynovial, intrasternal, intrathecal, intralesional and intracranial injection or infusion techniques.

A pharmaceutical composition can be in the form of a sterile aqueous solution or dispersion suitable for administration by either direct injection or by addition to sterile infusion fluids for intravenous infusion, and comprises a solvent or dispersion medium containing, water, ethanol, a polyol (e.g., glycerol, propylene glycol and liquid polyethylene glycol), suitable mixtures thereof, or one or more vegetable oils. Solutions or suspensions of the compound of the present disclosure as a free base or pharmacologically acceptable salt can be prepared in water suitably mixed with a surfactant. Examples of suitable surfactants are given below. Dispersions can also be prepared, for example, in glycerol, liquid polyethylene glycols and mixtures of the same in oils.

The pharmaceutical compositions for use in the methods of the present disclosure can further comprise one or more additives in addition to any carrier or diluent (such as lactose or mannitol) that is present in the formulation. The one or more additives can comprise or consist of one or more surfactants. Surfactants typically have one or more long aliphatic chains such as fatty acids which enables them to insert directly into the lipid structures of cells to enhance drug penetration and absorption. An empirical parameter commonly used to characterize the relative hydrophilicity and hydrophobicity of surfactants is the hydrophilic-lipophilic balance ("HLB" value). Surfactants with lower HLB values are more hydrophobic, and have greater solubility in oils, while surfactants with higher HLB values are more hydrophilic, and have greater solubility in aqueous solutions. Thus, hydrophilic surfactants are generally considered to be those compounds having an HLB value greater than about 10, and hydrophobic surfactants are generally those having an HLB value less than about 10. However, these HLB values are merely a guide since for many surfactants, the HLB values can differ by as much as about 8 HLB units, depending upon the empirical method chosen to determine the HLB value.

Among the surfactants for use in the compositions of the disclosure are polyethylene glycol (PEG)-fatty acids and PEG-fatty acid mono and diesters, PEG glycerol esters, alcohol-oil transesterification products, polyglyceryl fatty acids, propylene glycol fatty acid esters, sterol and sterol derivatives, polyethylene glycol sorbitan fatty acid esters, polyethylene glycol alkyl ethers, sugar and its derivatives, polyethylene glycol alkyl phenols, polyoxyethylene-polyoxypropylene (POE-POP) block copolymers, sorbitan fatty acid esters, ionic surfactants, fat-soluble vitamins and their salts, water-soluble vitamins and their amphiphilic derivatives, amino acids and their salts, and organic acids and their esters and anhydrides.

The present disclosure also provides packaging and kits comprising pharmaceutical compositions for use in the methods of the present disclosure. The kit can comprise one or more containers selected from the group consisting of a bottle, a vial, an ampoule, a blister pack, and a syringe. The kit can further include one or more of instructions for use in treating and/or preventing a disease, condition or disorder of the present disclosure, one or more syringes, one or more applicators, or a sterile solution suitable for reconstituting a pharmaceutical composition of the present disclosure.

All percentages and ratios used herein, unless otherwise indicated, are by weight. Other features and advantages of the present disclosure are apparent from the different examples. The provided examples illustrate different components and methodology useful in practicing the present disclosure. The examples do not limit the claimed disclosure. Based on the present disclosure the skilled artisan can identify and employ other components and methodology useful for practicing the present disclosure.

EXAMPLES

The following non-limiting examples are provided to further illustrate the invention disclosed herein. It will be appreciated by those of skill in the art that the techniques disclosed in the examples that follow represent approaches that have been found to function well in the practice of the invention and thus can be considered to constitute examples of modes for its practice. However, those of skill in the art will, in light of the present disclosure, appreciate that many changes can be made in the specific embodiments that are disclosed and still obtain a like or similar result without departing from the spirit and scope of the invention.

Cadherins mediate diverse processes critical in inflammation including cell adhesion, migration, and differentiation. Here, we report that the previously uncharacterized cadherin 26 (CDH26) is highly expressed by epithelial cells in human allergic gastrointestinal tissue and is induced by the Th2 cytokine IL-13. We further demonstrate that CDH26 promotes calcium-dependent cellular adhesion by a mechanism involving homotypic binding and interaction with catenin family members (alpha, beta, and p120) and that CDH26 overexpression enriches epithelial transcripts involved in cell adhesion, differentiation, and the IL-13 response. CDH26 enhances cellular adhesion to recombinant integrin $\alpha 4\beta 7$; conversely, recombinant CDH26 bound $\alpha E$ and $\alpha 4$ integrins in biochemical and cellular functional assays, respectively. CDH26-overexpressing cells displayed increased eotaxin-mediated eosinophil migration. In addition, CDH26-Fc inhibited activation of CD4+ T cells mediated by either suboptimal T cell receptor activation or by costimulation with suboptimal T cell receptor activation and VCAM-1-Fc, as indicated by surface expression of CD25, CD69, and CD154 as well as secretion of IL-2 and IL-4. Taken together, we have identified a novel functional cadherin regulated during allergic responses with unique immunomodulatory properties, as it impacts epithelial gene expression, binds $\alpha 4$ and $\alpha E$ integrins, and regulates leukocyte migration and activation.

Modeling the 3-Dimensional Structure of the Extracellular Domain of Human CDH26

Heterotypic binding of cadherins and integrins has been reported and there are a number of proteins known to bind integrins, including CDH1 as well as ICAM-1, MAdCAM-1, and fibronectin, for which 3D structures have been resolved and integrin binding sites have been localized. To map these sites to CDH26, we generated a 3D model of CDH26 structure using homology modeling with the CDH1 structure (PDB ID 3Q2V) as a primary template.

FIG. 10 shows the predicted 3-D structure of the extracellular domain of human CDH26. The model includes amino acids Asparagine 55 to Serine 599 (A). The N-terminus is located on the left side of the figure, and the C-terminal portion is located on the right side of the figure. The model was obtained using the Phyre2 server and was visualized using Swiss-PdbViewer. In panels B-F, each of the extracellular cadherin repeat domains (EC1 to EC 5) is individually denoted in black, with the remainder of the putative extracellular domain shown in gray.

The pairwise structure alignment of the model with other resolved structures indicates putative integrin binding sites in CDH26. We found the CDH26 putative integrin binding sites to be located in unstructured loops of EC1. For example, D42 of MAdCAM-1 and E34 of ICAM-1 overlap with the acidic residues D98, E99, and E102 in the EC1 of CDH26. D1495 of fibronectin corresponds to E138 in the EC1 of CDH26. The presence of these negatively charged residues in unstructured loops on the surface suggests that they are involved in CDH26 binding to integrins. Also possibly involved is N85 in the EC1 of CDH26 which maps to E31 of CDH1. However, N85 is less likely an integrin binding site, since a negatively charged residue is required and CDH26 does not contain any Asp or Glu residues on the surface in close proximity to this location. However, this residue may be involved in the mechanism by which CDH26 binds integrins.

It is know that certain subfamilies of cadherins, including type I and type II cadherins, contain a tryptophan residue at position 2 of the most N-terminal EC domain that is critical for dimerization in trans of type I and type II cadherins. Based on comparison of the primary amino acid sequence of CDH26 to other cadherins, we identified that CDH26 contains a tryptophan residue (W56) corresponding to this position. W56 in the EC1 of CDH26 is predicted to function in the dimerization of the cadherin molecule, for example in promoting homotypic interaction of CDH26 molecules, but it is not predicted to be involved in CDH26 binding to integrins.

CDH26 is Overexpressed During Pathologic Allergic Inflammation

Following global transcript analysis of gastric tissue of control patients and patients with an allergic eosinophilic gastroenteropathy, eosinophilic gastritis (EG) (data not shown), we identified that the most upregulated transcript (passing the criteria P<0.01 and 2-fold filter) in patients with active EG was the uncharacterized cadherin family member cadherin 26 (CDH26) (12.3 fold, P<0.005; data not shown). We verified by real time polymerase chain reaction (RT-PCR) analysis that the CDH26 mRNA level was highly increased in the gastric tissue of EG patients within the same cohort subjected to microarray (15.3-fold, n=5 EG vs. n=5 control, P=0.0317; data not shown) as well as in additional EG patient gastric tissue (35.6 fold, n=10 EG vs. n=10 control, P<0.0001; data not shown). Comparison of the genes differentially regulated in EG (data not shown) and in eosinophilic esophagitis (EoE) (Blanchard et al. Eotaxin-3 and a uniquely conserved gene-expression profile in eosinophilic esophagitis. J Clin Invest. 2006; 116(2):536-47) revealed that CDH26 was the only cadherin family member that exhibited a significant change in gene expression in both allergic disorders. Indeed, as previously observed (18), CDH26 mRNA expression was significantly increased (115 fold) in the esophageal tissue of patients with active EoE compared to control patients (data not shown). Only CDH1 (E-cadherin) and CDH26 exhibited raw signal indicative of the transcript being substantially expressed in the gastric tissue of patients with active EG (data not shown). Raw signals for cadherin transcripts in esophageal tissue from EoE patients only showed high values for CDH1, CDH3 (P-cadherin), and CDH26 (data not shown). As a control, no significant change in CDH26 or CCL26 (eotaxin-3) expression was observed in gastric tissue of patients with *H. pylori* gastritis compared to control patients, although as a control C3 transcript was elevated in the *H. pylori* cohort as previously reported. Notably, a microarray study of gastric antrum tissue of patients with *H. pylori* gastritis did not identify CDH26 as being upregulated compared to normal tissue (Ikuse T, et al. Microarray analysis of gastric mucosa among children with *Helicobacter pylori* infection. Pediatr Int. 2012; 54(3):319-24). As such, CDH26 is a unique cadherin in terms of its expression level and regulation in two distinct allergic states.

CDH26 Protein Expression is Increased in Inflamed Allergic Gastrointestinal Tissue and is Localized to Epithelial Cells Immunohistochemical staining for CDH26 showed cytoplasmic localization with focal membrane accentuation in the surface epithelial cells in gastric tissue of patients with EG. The peak number of CDH26-positive cells was 241 cells/400× high-power field (HPF) (mean±SEM, 104.2±40.8) in EG patients compared with no expression above background in controls. Western blot revealed an increased level of gastric CDH26 (4.9 fold) in EG patients compared to control samples. Patients with active EoE had high levels of esophageal CDH26 protein expression compared to control patients. In control esophageal biopsies, the staining was confined to epithelial cells near the surface, but in active EoE the staining was both more intense and prevalent and included cells in the expanded basal layer. Consistent with the immunohistochemistry results, by western blot analysis, esophageal tissue of EoE patients showed 3.4-fold increased CDH26 protein levels compared to control tissue.

IL-13 is Sufficient to Promote Epithelial CDH26 Expression

IL-13 is a key Th2 cytokine that has been shown to be important in allergic and eosinophilic responses. Indeed, IL13 transcript levels were elevated in the gastric tissue of patients with EG (mean 44 fold). Upon IL-13 stimulation, CDH26 mRNA increased in a dose-dependent manner in primary esophageal epithelial cells, the esophageal cell line TE-7, and the gastric cell line NCI-N87. As a control, TNF-α stimulation did not induce CDH26. Expression of dominant-negative STAT6 in TE-7 cells attenuated IL-13-mediated induction of CDH26 (2.6 fold vs. non-targeting siRNA).

CDH26 is a Functional Cadherin

CDH26 exhibits sequence homology to the cadherin family of proteins, with 4 extracellular cadherin repeats (EC) and a cadherin domain in the putative extracellular portion of the protein, a predicted transmembrane domain, and a C-terminal cytoplasmic region (FIG. 1A). To determine if CDH26 localized to the cell membrane of esophageal and gastric epithelial cells, affinity isolation of biotinylated surface proteins was performed. Western blot for CDH26 indicated that it was present at the cell surface in TE-7 and NCI-N87 cells that express high levels of CDH26 (FIGS. 1, B and C). CDH26 contains five asparagine residues in its extracellular domain located within the consensus sequence for N-glycosylation (N81, N85, N171, N177, N462) Immunoprecipitated CDH26 treated with peptide: N-glycosidase F (PNgase F), but not heat-inactivated PNgase F, exhibited increased mobility compared to CDH26 from total cell lysates (FIG. 1D), indicating that the protein is modified by N-glycosylation under baseline conditions.

Figure 2A:
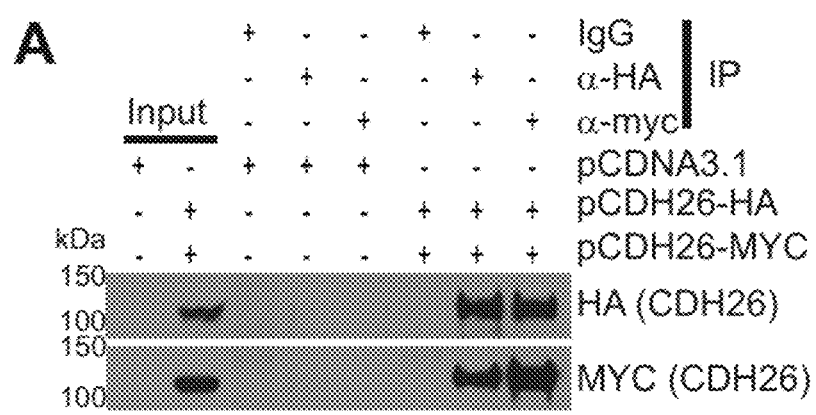
FIGS. 2A-2F: Biochemical and functional properties of CDH26. (A-D) Immunoprecipitates from transiently transfected HEK 293T cells and inputs (1/10 of amount used for IP) were subjected to SDS-PAGE and western blot analysis. Each blot shown is representative of 3 independent experiments. (E) Transduced HEK 293T cells were dispersed, incubated in buffer either containing or lacking 1 mM $CaCl_2$, and assessed for the degree of aggregation. (F) Aggregation assays were carried out as in E, except that transduced L929 cells were used. For E and F, data show 1 experiment representative of 3 and were analyzed by one-way ANOVA followed by Tukey post-test.

CDH26 contains a tryptophan residue at position 2 of the most N-terminal EC domain known to be critical for dimerization in trans of type I and type II cadherins (Shapiro L, and Weis W I. Structure and biochemistry of cadherins and catenins. Cold Spring Harb Perspect Biol. 2009; 1(3): a003053). Therefore, we tested whether CDH26 molecules interact in a homotypic manner HEK 293T cells were co-transfected with two separate expression constructs containing either CDH26-MYC or CDH26-HA. Myc-tagged CDH26 co-immunoprecipitated with HA-tagged CDH26, and the reciprocal immunoprecipitation confirmed that CDH26-HA co-immunoprecipitated with CDH26-MYC (FIG. 2A).

Figure 2B:
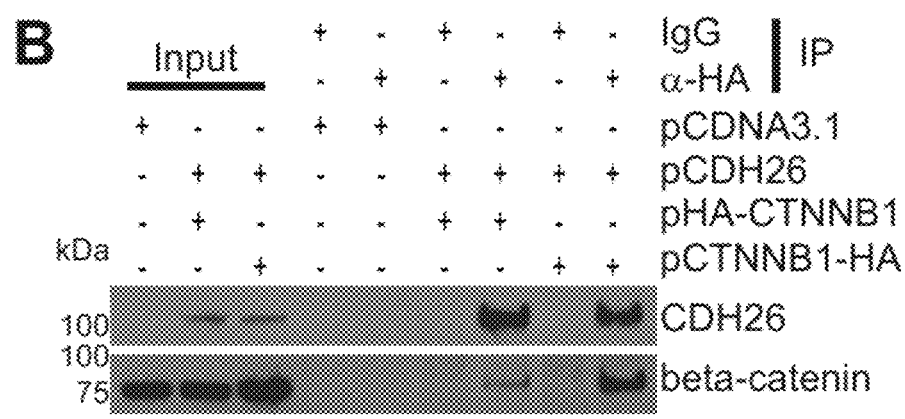

We next tested whether CDH26 interacted with beta-catenin, which binds other cadherin molecules to link them indirectly to the actin cytoskeleton. The region of CDH1 known to interact with beta-catenin exhibited 68% similarity to the same region of CDH26 (Jou T S, et al. Genetic and biochemical dissection of protein linkages in the cadherin-catenin complex. Proc Natl Acad Sci USA. 1995; 92(11): 5067-71; Stappert J, and Kemler R. A short core region of E-cadherin is essential for catenin binding and is highly phosphorylated. Cell Adhes Commun. 1994; 2(4):319-27). When immunoprecipitation for HA-tagged beta-catenin was performed, CDH26 was also detected in the precipitates (FIG. 2B), indicating that ectopically expressed beta-catenin and CDH26 exist in the same complex in HEK 293T cells.

Figure 2C:
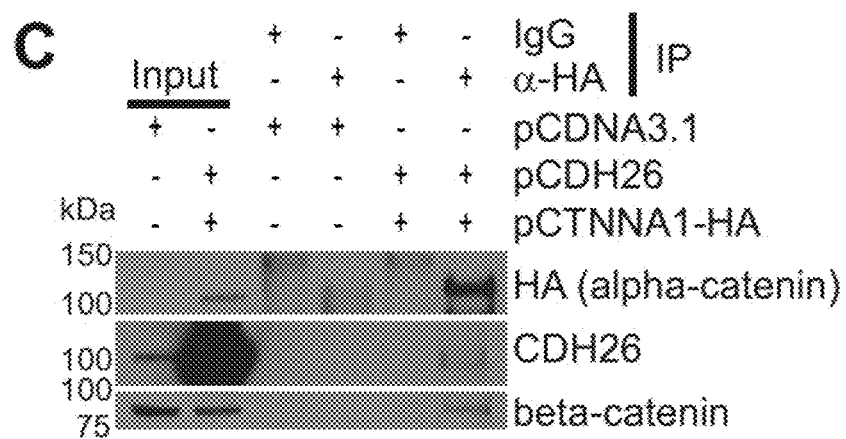
Figure 2D:
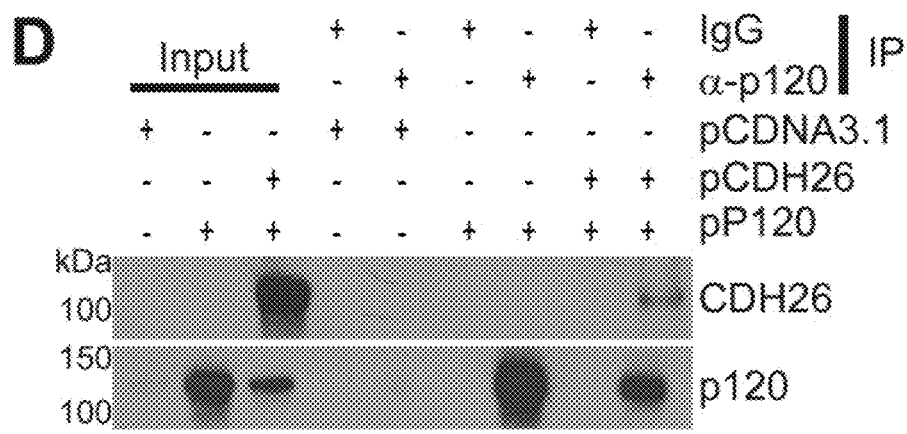

Beta-catenin interacts with alpha-catenin to link cadherin molecules indirectly to the actin cytoskeleton and thus support cell adhesion. We tested whether alpha-catenin exists in the same complex as CDH26 and found that CDH26 co-immunoprecipitated with alpha-catenin. As a positive control, beta-catenin was also observed to co-immunoprecipitate with alpha-catenin (FIG. 2C).

p120-catenin binds the juxtamembrane domain of the cytoplasmic portion of cadherin molecules and has been shown to function in maintenance of cadherin stability and localization to the cell surface. The primary amino acid sequence of the juxtamembrane domain of CDH1 was notably homologous (48%) to that in CDH26. We therefore tested whether CDH26 and p120-catenin could exist in the same protein complex. p120-catenin and CDH26 co-immunoprecipitated from lysates derived from transiently transfected HEK 293T cells (FIG. 2D).

Figure 2E:
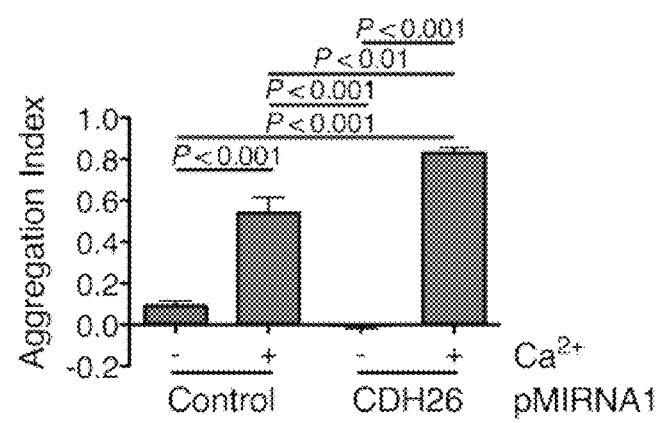
Figure 2F:
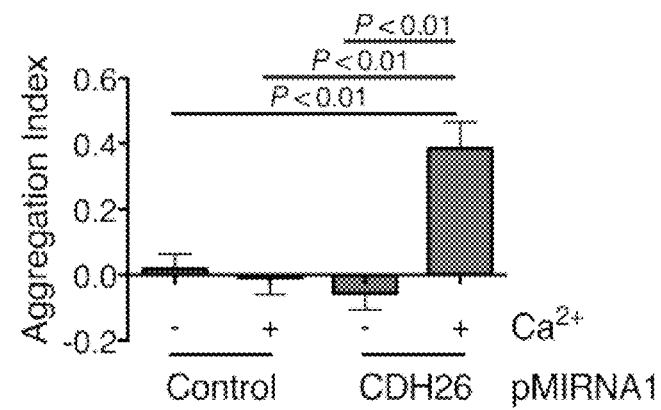

We tested whether CDH26 could promote calcium-dependent cellular adhesion. Transduced HEK 293T cells were dispersed with trypsin in the presence of calcium, and single cells were incubated in buffer either lacking or containing $CaCl_2$. Neither control nor CDH26-overexpressing HEK 293T cells aggregated in the absence of calcium. Both cell types exhibited aggregation in the presence of calcium, with CDH26-overexpressing cells exhibiting a greater degree of aggregation compared to control cells (FIG. 2E). Transduced L929 cells, which lack endogenous cadherins, were used in the same aggregation assay. CDH26-transduced L929 cells, but not control cells, showed a high degree of aggregation in the presence of calcium (FIG. 2F).

CDH26 Engagement Initiates Intracellular Signaling

Figure 3A:
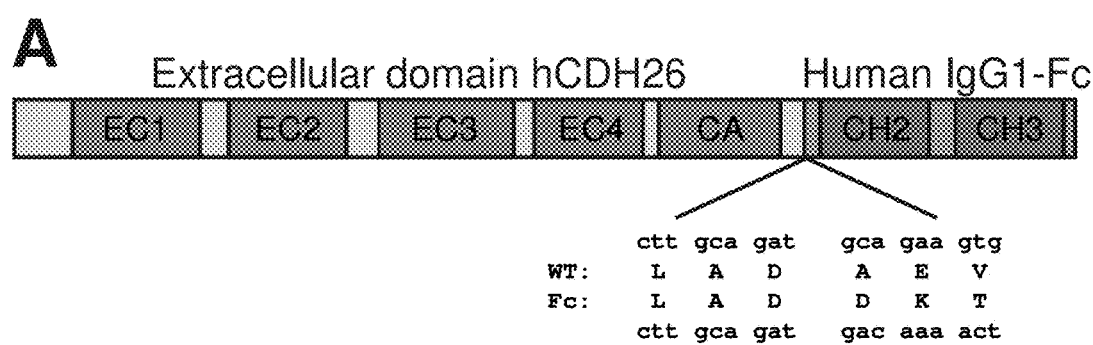
FIGS. 3A-3D: CDH26 engagement activates ERK. (A) Schematic representation of CDH26-hIgG1-Fc fusion protein, including the nucleotide sequence encoding the junction between the CDH26 extracellular domain and the Fc portion of human IgG1 (Fc) compared to the corresponding sequence encoding the wild-type protein (WT). (B) CDH26-hIgG1-Fc fusion protein isolated by protein G affinity chromatography was subjected to western blot analysis. Lower arrow, CDH26-hIgG1-Fc monomer; Upper arrow, CDH26-hIgG1-Fc dimer. (C) CDH26-hIgG1-Fc (CDH26-Fc) fusion protein (20 ug/ml), hIgG1 control antibody (20 ug/ml), or TNF-α (10 ng/ml) was added to the supernatant of transduced L929 cell clones. Protein lysates were collected and subjected to SDS-PAGE and western blot analysis. The ratio of (phospho-ERK1/2/total ERK1/2) to actin signal was graphed as fold change relative to untreated for each cell type. The graph represents the average of 3 experiments that each included 3 separate control and 3 separate CDH26-overexpressing clones. A representative blot of one control and one CDH26-overexpressing clone from one experiment is shown. Data were analyzed by t test. **pMIRNA1-CDH26/CDH26-Fc 0 min vs. 5 min; #pMIRNA1-control/CDH26-Fc 5 min vs. pMIRNA1-CDH26/CDH26-Fc 5 min. (D) Transduced L929 cell clones were incubated in media lacking calcium for 3 h, followed by restoration of calcium concentration to 1.8 mM. Protein lysates were collected and subjected to SDS-PAGE and western blot analysis. The ratio of (phospho-ERK1/2/total ERK1/2) to actin signal was graphed as fold change relative to pre-calcium restoration for each cell type. The graph represents the average of 3 experiments that each included 3 separate control and 3 separate CDH26-overexpressing clones. Data were analyzed by 2-way ANOVA; a significant interaction was observed when comparing pMIRNA1-control to pMIRNA1-CDH26.
Figure 3B:
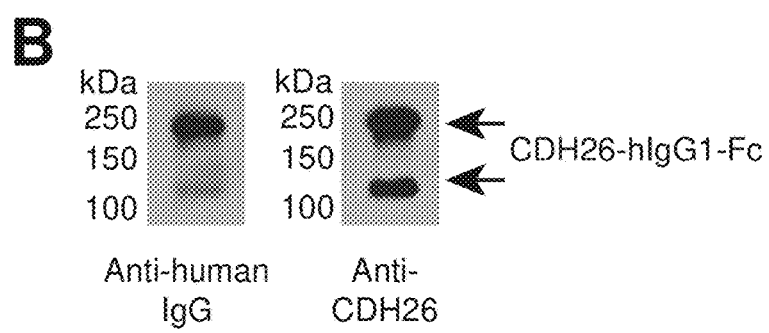
Figure 3C:
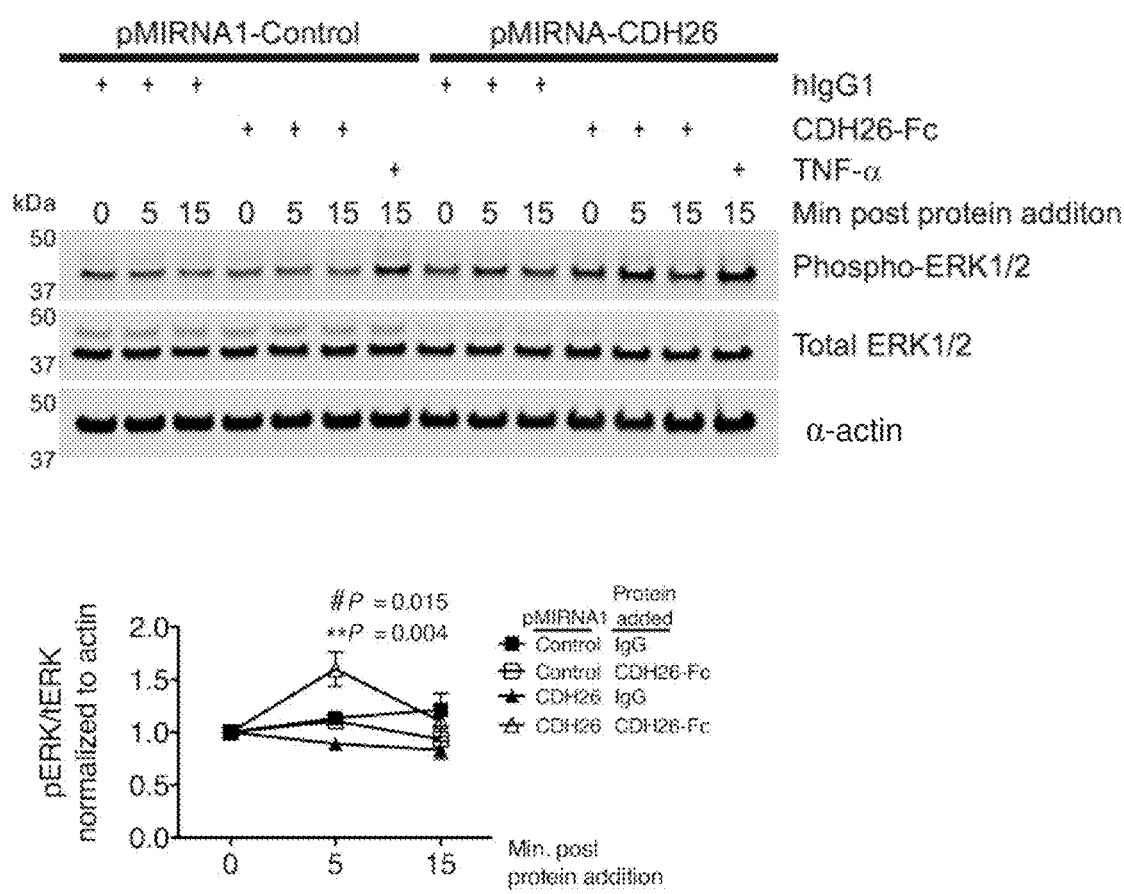

Cadherin engagement has been shown to initiate intracellular signaling including activation of MAPK family members (Pece S, and Gutkind J S. Signaling from E-cadherins to the MAPK pathway by the recruitment and activation of epidermal growth factor receptors upon cell-cell contact formation. J Biol Chem. 2000; 275(52):41227-33; Reddy P, et al. Formation of E-cadherin-mediated cell-cell adhesion activates AKT and mitogen activated protein kinase via phosphatidylinositol 3 kinase and ligand-independent activation of epidermal growth factor receptor in ovarian cancer cells. Mol Endocrinol. 2005; 19(10):2564-78). To test if CDH26 engagement activated the ERK pathway, a CDH26-hIgG1-Fc fusion protein was generated (FIG. 3A) and used to treat L929 cells. The fusion protein was recognized by antibodies directed against human IgG and CDH26 (FIG. 3B) and contained a low level of endotoxin. L929 cells overexpressing CDH26 were treated with the fusion protein or hIgG1 antibody. Protein lysates were collected kinetically following addition of the fusion protein, and western blot analysis was performed to detect phospho- and total p44/42 ERK1/2. Increased phosphorylated ERK signal was observed compared to the equivalent dose of control antibody or that observed when control cells were treated with the fusion protein (FIG. 3C).

Figure 3D:
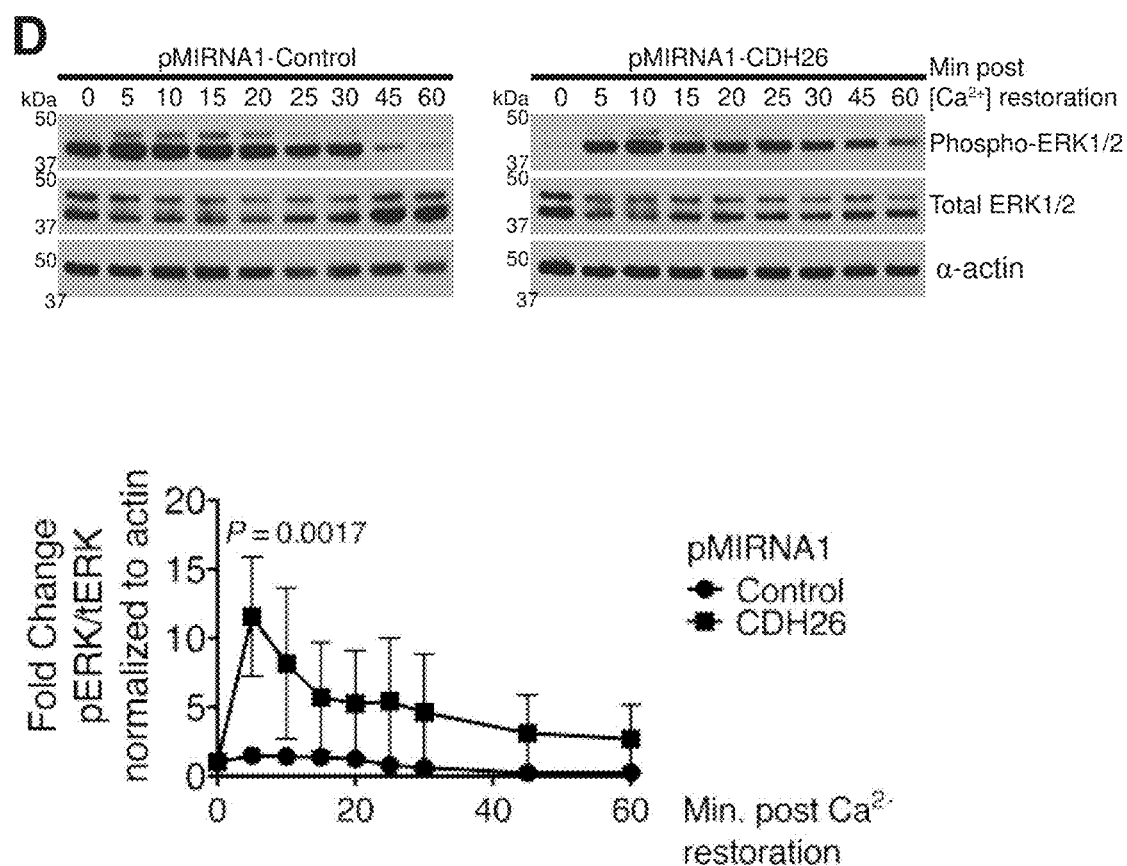

We sought to determine if CDH26 engagement promoted activation of intracellular signaling pathways using an independent method. L929 cells transduced with either a control or CDH26 expression construct were grown to confluency and incubated in media lacking calcium to promote disengagement of cadherins on adjacent cells. The calcium concentration of the media was then increased to 1.8 mM to promote cadherin binding in trans. Phosphorylation of p44/42 ERK1/2 was then monitored kinetically after calcium restoration. We observed that at baseline and following incubation in calcium-free media, CDH26-overexpressing L929 clones had lower phospho-ERK levels compared to control clones. In control L929 cells, little if any ERK phosphorylation (1.5-fold increased at 5 min) was observed upon calcium restoration. In contrast, cells that expressed CDH26 showed 11.6-fold increased phosphorylation of ERK upon calcium restoration; the phospho-ERK level subsequently diminished although with delayed kinetics compared to control cells (FIG. 3D).

CDH26 Impacts Epithelial Cell Gene Expression Profile

Since CDH26 engagement may have the capacity to induce intracellular signaling, including activation of the ERK pathway, we hypothesized that activation of these pathways could impact epithelial cell gene expression relevant to inflammation. We performed microarray analysis to compare global gene expression of TE-7 cells transduced with either a control or CDH26-overexpression construct that were cultured under conditions permissive for CDH26 engagement (i.e. [Ca2+]=1.8 mM). A panel of 86 transcripts was identified to have altered levels: 79 transcripts exhibited increased levels, and 7 showed decreased levels in CDH26-overexpressing cells compared to control cells ($P<0.05$ and $\geq$2-fold change). Notable upregulated genes included CDH26 (positive control), members of protease (MMP7), protease inhibitor (SERPINB3, SERPINB13, SERPINB7), and cadherin (PCDH18, CDH10, PCDH9, PCDH7, FAT4) families. Gene ontology analysis was performed on the set of 2223 genes passing the criteria $P<0.05$ (moderated t test) and ranked according to fold change after removing CDH26 from the list, and the top processes identified were homophilic cell adhesion ($P=1.04\times10-5$), cell adhesion ($P=1.40\times10-4$), and cell differentiation ($P=4.04\times10-4$). Interestingly, overexpression of CDH26 in an esophageal epithelial cell line was sufficient to promote changes in gene expression that partially overlapped with the transcripts altered in primary esophageal epithelial cells stimulated with IL-13 (Blanchard C, et al. IL-13 involvement in eosinophilic esophagitis: transcriptome analysis and reversibility with glucocorticoids. J Allergy Clin Immunol. 2007; 120(6): 1292-300). Of the 86 differentially expressed genes, 16 (which included CDH26 as a positive control) were altered in IL-13-stimulated primary esophageal epithelial cells. Eight of these genes (SERPINB3, SERPINB13, CDH26, CYP1B1, DYPD, LOX, EHF, AASS) were upregulated in both TE-7 cells overexpressing CDH26 and IL-13-stimulated primary esophageal epithelial cells.

CDH26 Enhances Eosinophil Transmigration

Figure 4:
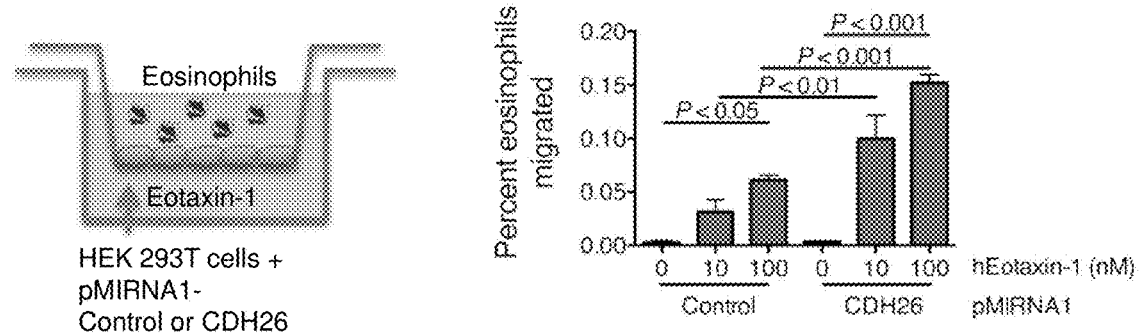
FIG. 4: Effect of CDH26 on eotaxin-1-mediated eosinophil cell transmigration. Transduced HEK 293T cells were seeded on top of transwells. Left: Eosinophils were added to the top chamber, and buffer containing the indicated concentration of eotaxin-1 was added to the bottom chamber (n=3 samples per group). Right: The fraction of eosinophils present in the bottom chamber after 1.5 h is shown. One representative experiment is shown (n=3). Data were analyzed by one-way ANOVA followed by Tukey post-test.

We hypothesized that an increased amount of CDH26 expressed on the surface of cells could impact the transmigration of eosinophils through such cells. Human peripheral blood eosinophils were placed in the upper chamber of transwells coated with HEK 293T cells transduced with either a control or CDH26 expression vector (FIG. 4, left); cells transduced with the CDH26 expression vector showed highly increased CDH26 expression, a portion of which localized to the cell surface. Eosinophils migrated through control cells toward eotaxin-1 in a dose-dependent manner. Migration was increased at each dose of eotaxin-1 through cells that overexpressed CDH26 compared to control cells (FIG. 4, right).

CDH26 Binds α4 and αE Integrins

Figure 5A:
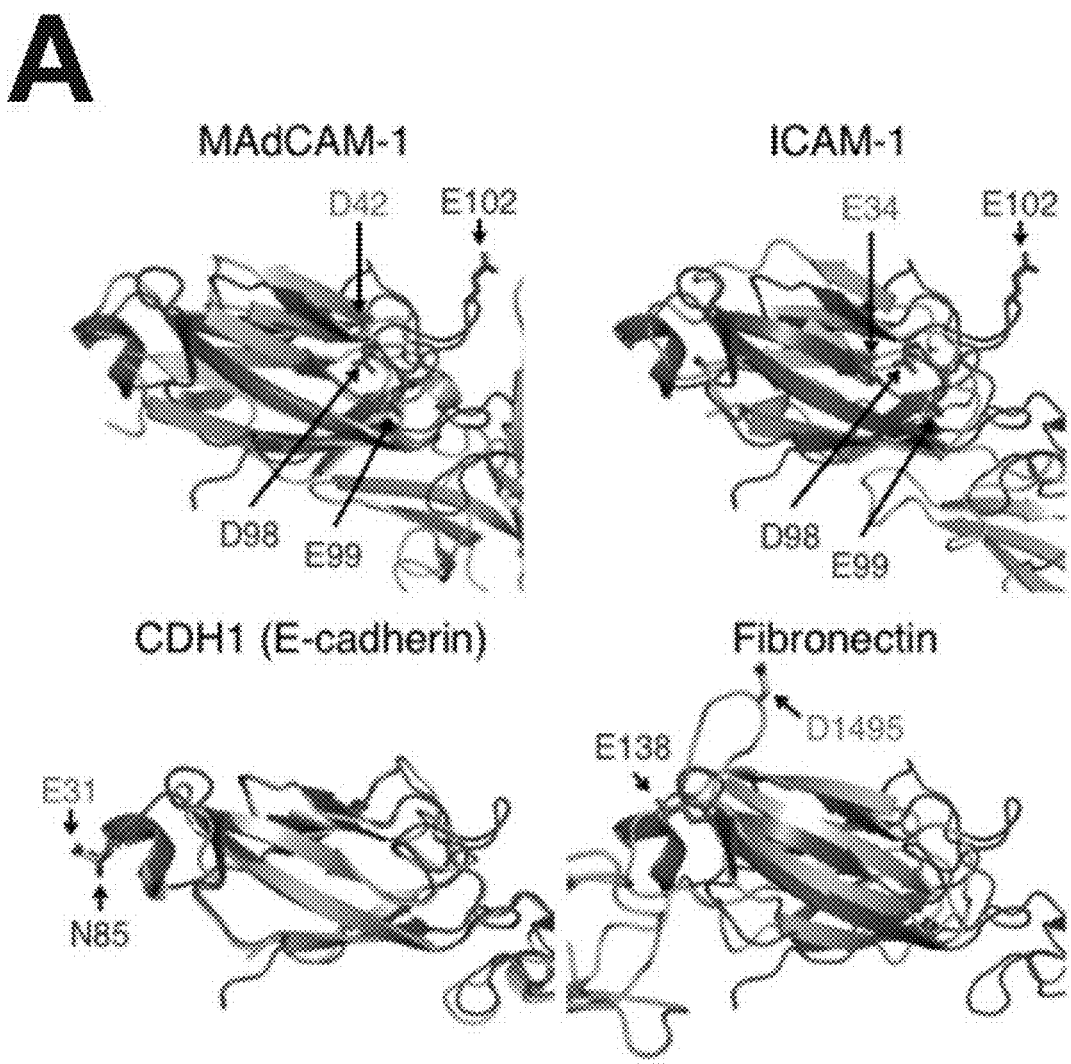
FIGS. 5A-5D: Binding of CDH26 to integrin α4β7. (A) Pairwise structure alignment of CDH26 with known integrin ligands. CDH26 structure was modeled (dark gray) and aligned to the resolved structures of MAdCAM-1 (PDB ID 1BQS), ICAM-1 (PDB ID 1IC1), CDH1 (PDB ID 1EDH), and fibronectin (PDB ID 1FNF) (light gray). For each pair, integrin binding amino acids and the corresponding CDH26 residues are labeled (arrows) and rendered using a stick representation. (B) Transduced L929 cell clones were dispersed and added to wells coated with either BSA or recombinant α4β7. The percentage of adherent cells remaining after wells were washed is shown. The graph represents seven experiments combined that each involved separate control and CDH26-overexpressing clones. (C) Pictures of Giemsa-stained wells from B were taken (magnification=4x), with 1 control and 1 CDH26-overexpressing clone shown. (D) Wells were coated with or without recombinant α4β37 and then blocked with BSA, followed by addition of either IgG1κ or CDH26-hIgG1-Fc (CDH26-Fc). Bound antibody or fusion protein was then detected and expressed as A450 nm-A900 nm. Each condition was performed in triplicate. This graph shows 1 experiment representative of 3. For B and D, data were analyzed by one-way ANOVA followed by Tukey post-test.

Heterotypic binding of cadherins and integrins has been reported (Cepek K L et al. Adhesion between epithelial cells and T lymphocytes mediated by E-cadherin and the alpha E beta 7 integrin. Nature. 1994 372(6502):190-3; Whittard J D et al. E-cadherin is a ligand for integrin alpha2beta1. Matrix Biol. 2002; 21(6):525-32). There are a number of proteins known to bind integrins, including CDH1 as well as ICAM-1, MAdCAM-1, and fibronectin, for which 3D structures have been resolved and integrin binding sites have been localized (Cepek K L et al. Adhesion between epithelial cells and T lymphocytes mediated by E-cadherin and the alpha E beta 7 integrin. Nature. 1994; 372(6502):190-3). To map these sites to CDH26, we generated a 3D model of CDH26 structure using homology modeling with the CDH1 structure (PDB ID 3Q2V) as a primary template. FIG. 5A shows the pairwise structure alignment of the model (dark gray) with other resolved structures (light gray) indicating putative integrin binding sites in CDH26. As can be seen, known integrin binding sites are located in unstructured loops of the extracellular domain and are negatively charged. D42 of MAdCAM-1 and E34 of ICAM-1 overlap with D98, E99, and E102 in CDH26. D1495 of fibronectin corresponds to E138 of CDH26. The presence of these negatively charged residues in unstructured loops on the surface suggests that CDH26 would bind integrins. However, while E31 of CDH1 coincides very well with N85 of CDH26, the latter is unlikely an integrin binding site, as a negatively charged residue is required, whereas CDH26 does not contain any Asp or Glu residues on the surface in close proximity to this location.

Figure 5B:
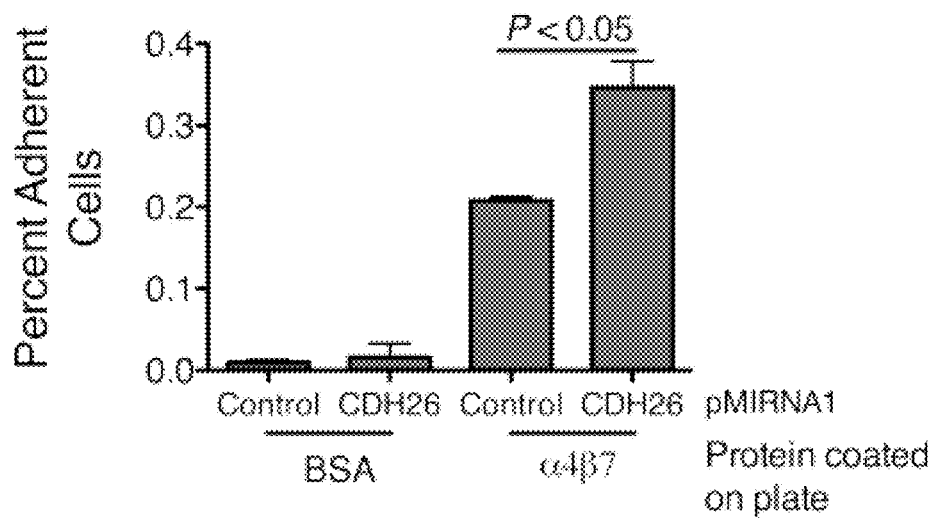
Figure 5C:
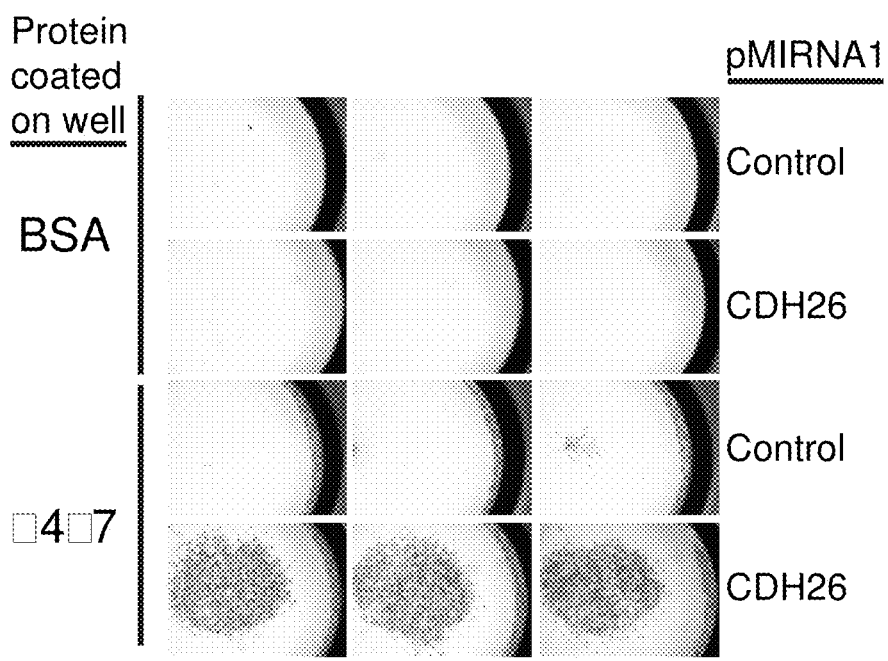
Figure 5D:
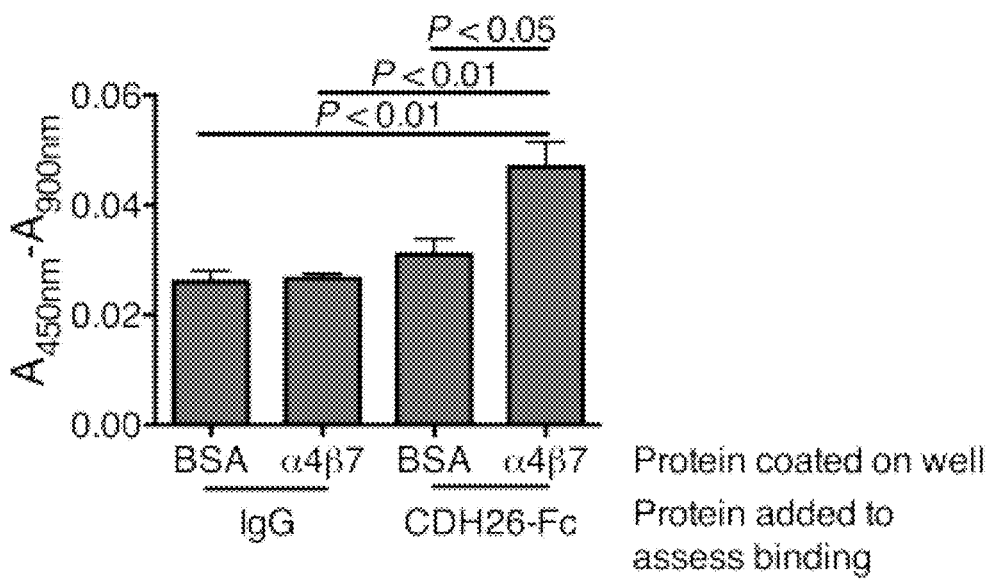

We tested whether L929 cells expressing high levels of CDH26 exhibited adhesion to α4β7 compared to control cells. Indeed, L929 cells transduced with a CDH26 expression vector showed increased adhesion to α4β7-coated wells compared to control cells, in contrast to BSA-coated wells, which did not support adhesion of either cell type (FIG. 5B). Visualization of cellular binding revealed a marked increase of CDH26-expressing cells binding α4β7 (FIG. 5C). To further prove that CDH26 could directly bind α4β7, a solid phase adhesion assay was performed in which recombinant CDH26-hIgG1-Fc was added to wells that were coated with recombinant α4β7. CDH26-hIgG1-Fc bound specifically to α4β7 and not BSA, while negative control IgG1κ did not bind either α4β7 or BSA (FIG. 5D).

To further substantiate and address the specificity and molecular requirements for CDH26/α4β7 interaction, overexpression and co-immunoprecipitation studies were carried out using HEK 293T cells. When HA-tagged CDH26

(CDH26-HA) and integrin α4 were overexpressed in HEK 293T cells, integrin α4 co-immunoprecipitated with CDH26-HA, and the reciprocal was observed as CDH26-HA was found to co-immunoprecipitate with integrin α4. In addition to integrin α4, V5-tagged integrin αE (ITGAE-V5) was observed to co-immunoprecipitate with CDH26-HA. Integrin α4 did not co-immunoprecipitate with CDH1, although integrin αE co-immunoprecipitated with CDH1.

Figure 6A:
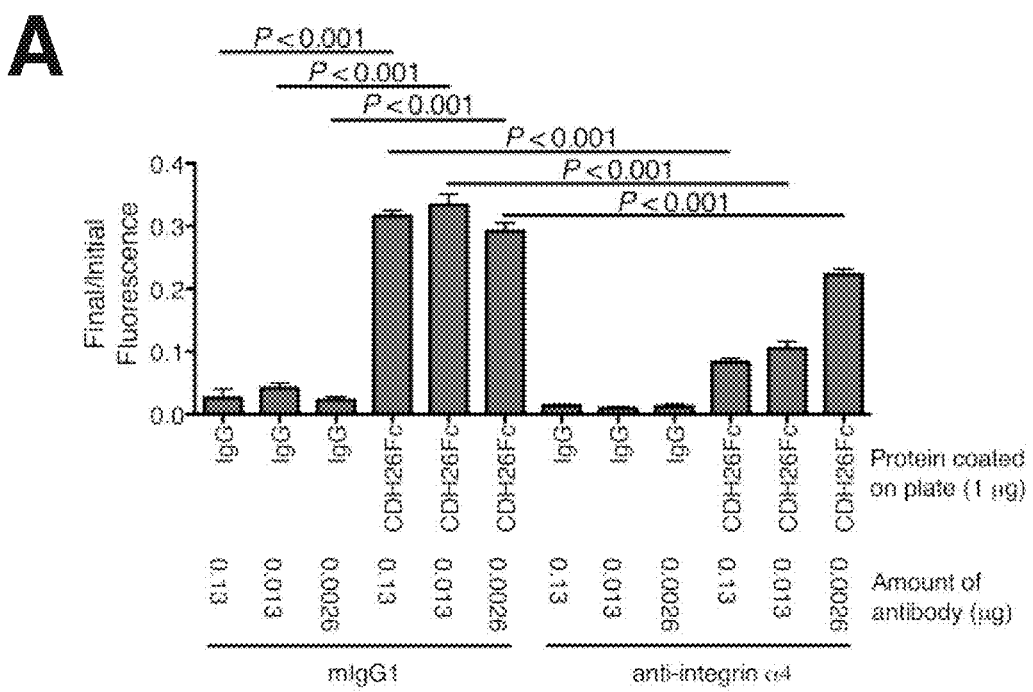
FIGS. 6A-6D: Cell adhesion to CDH26-Fc and requirement for integrin α4. (A-C) Fluorescently labeled Jurkat cells (untreated [A] or incubated with TS2/16 integrin β1-activating antibodies [B and C]) pre-incubated with the indicated amount of either control mIgG1 or anti-integrin α4 (HP2/1) antibodies were added to wells coated with control hIgG1, CDH26-hIgG1-Fc (CDH26-Fc), E-cadherin-hIgG1-Fc (Ecadherin-Fc), and/or VCAM-1-hIgG1-Fc (VCAM-1-Fc), as indicated. The graph indicates the percentage of fluorescence remaining after wells were washed. (D) Fluorescently labeled human peripheral blood CD4+ T cells treated with TS2/16 integrin β1-activating antibodies were added to wells coated with control hIgG1, CDH26-hIgG1-Fc (CDH26-Fc) and/or VCAM-1-hIgG1-Fc (VCAM-1-Fc), as indicated. The graph indicates the percentage of fluorescence remaining after wells were washed. (E) Human peripheral blood eosinophils were added to wells coated with control hIgG1, CDH26-hIgG1-Fc (CDH26-Fc), and/or VCAM-1-hIgG1-Fc (VCAM-1-Fc), as indicated. The graph indicates the percentage of eosinophils remaining after wells were washed as determined by residual eosinophil peroxidase activity. Data were analyzed by one-way ANOVA followed by Tukey post-test.
Figure 6B:
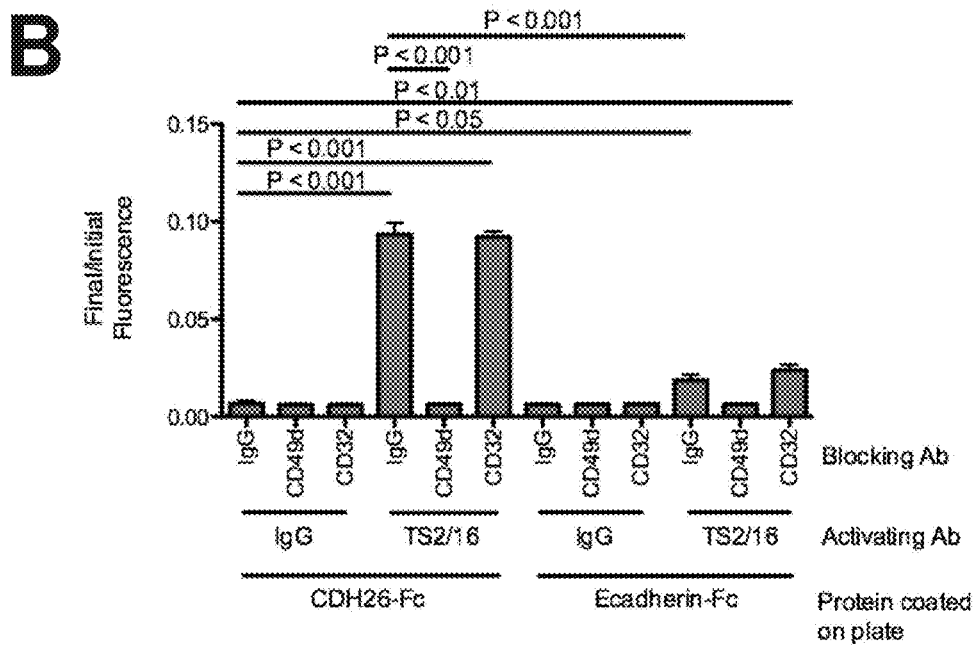
Figure 6C:
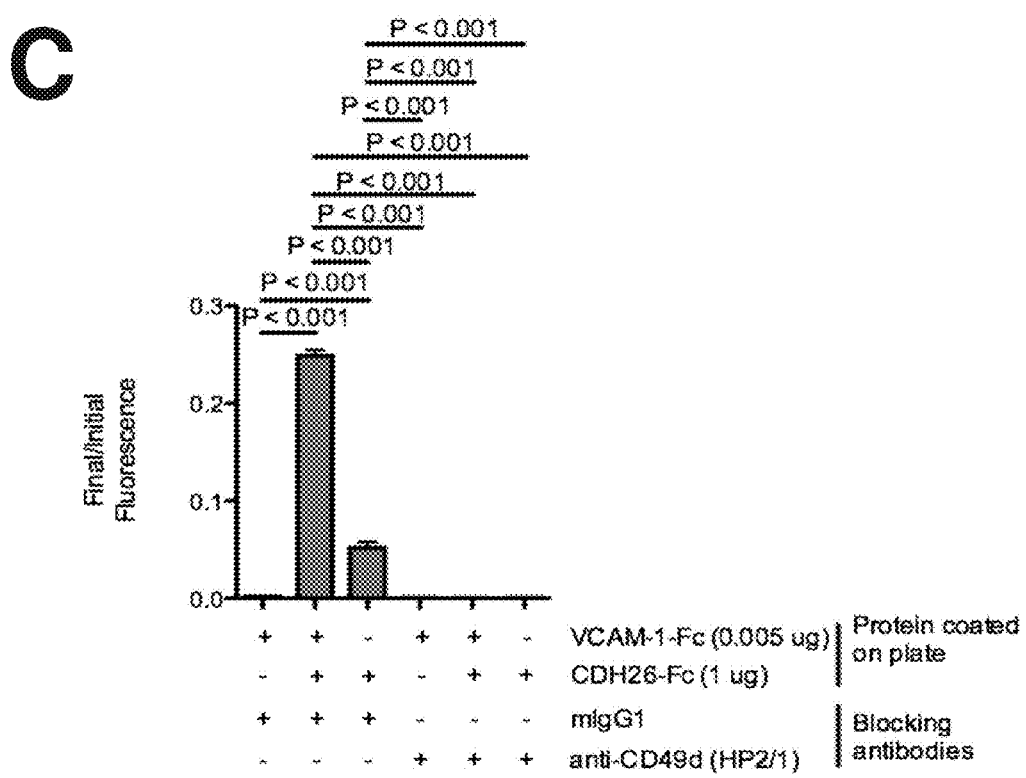
Figure 6D:
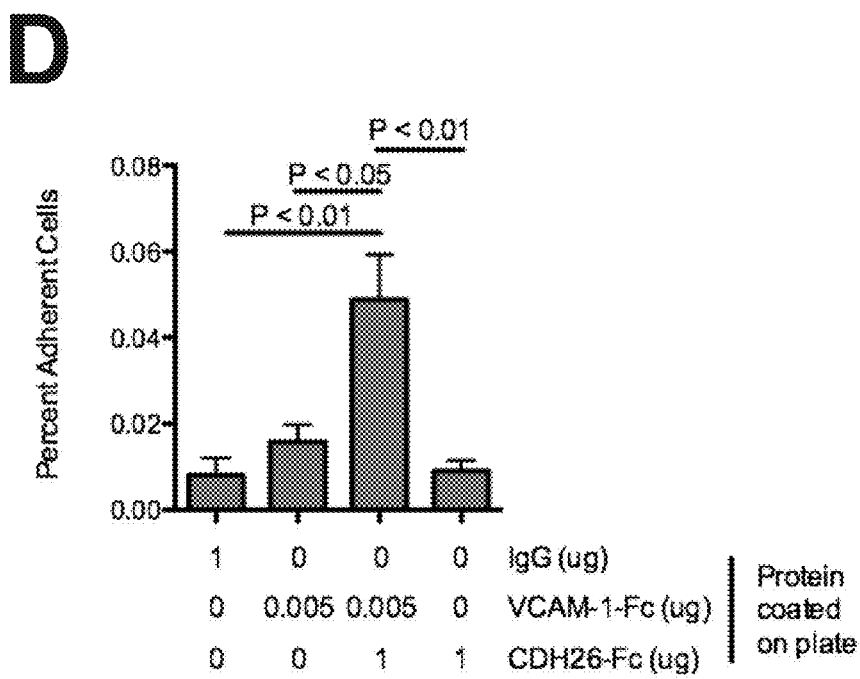
Figure 6E:
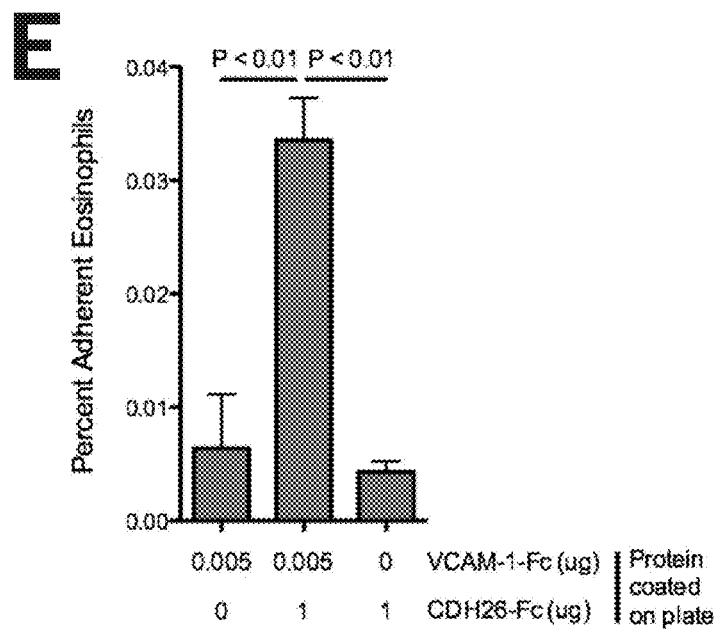
Figure 10A:
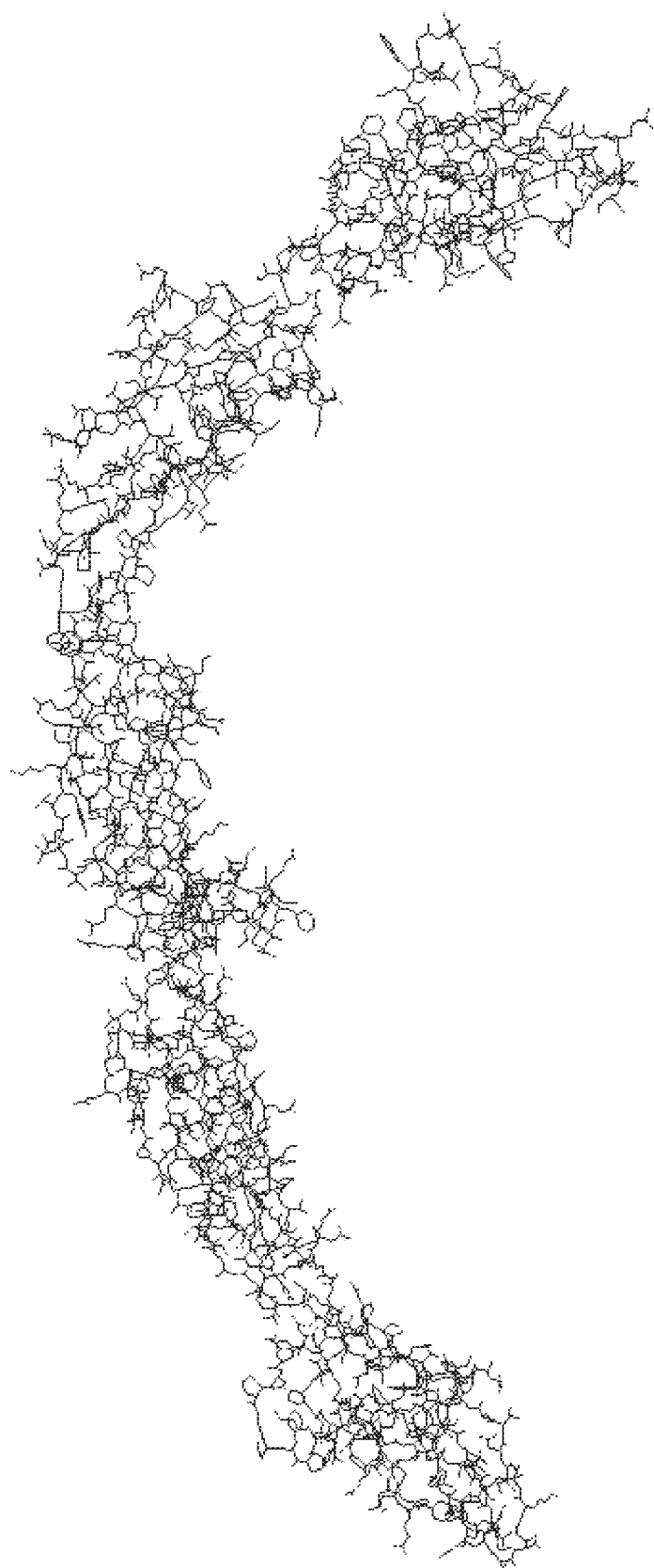
FIGS. 10A-10F: Modeling the 3-dimensional structure of the extracellular domain of human CDH26. The model includes amino acids Asparagine 55 to Serine 599 (A). The N-terminus is located on the left side of the figure, and the C-terminal portion is located on the right side of the figure. The model was obtained using the Phyre2 server and was visualized using Swiss-PdbViewer. In panels B-F, each of the extracellular cadherin repeat domains is individually denoted in black, with the remainder of the putative extracellular domain shown in gray as follows: (B) EC1, (C) EC2, (D) EC3, (E) EC4, (F) EC5.
Figure 10B:
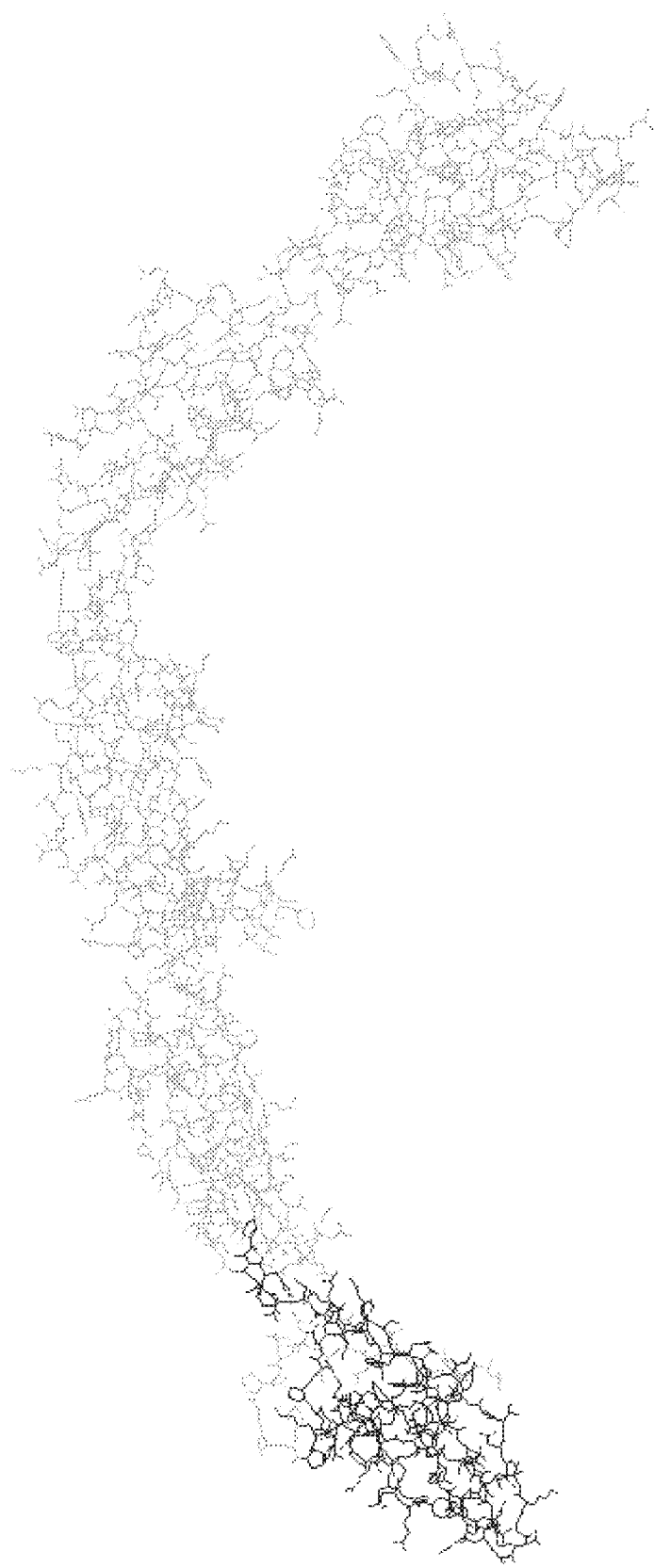
Figure 10C:
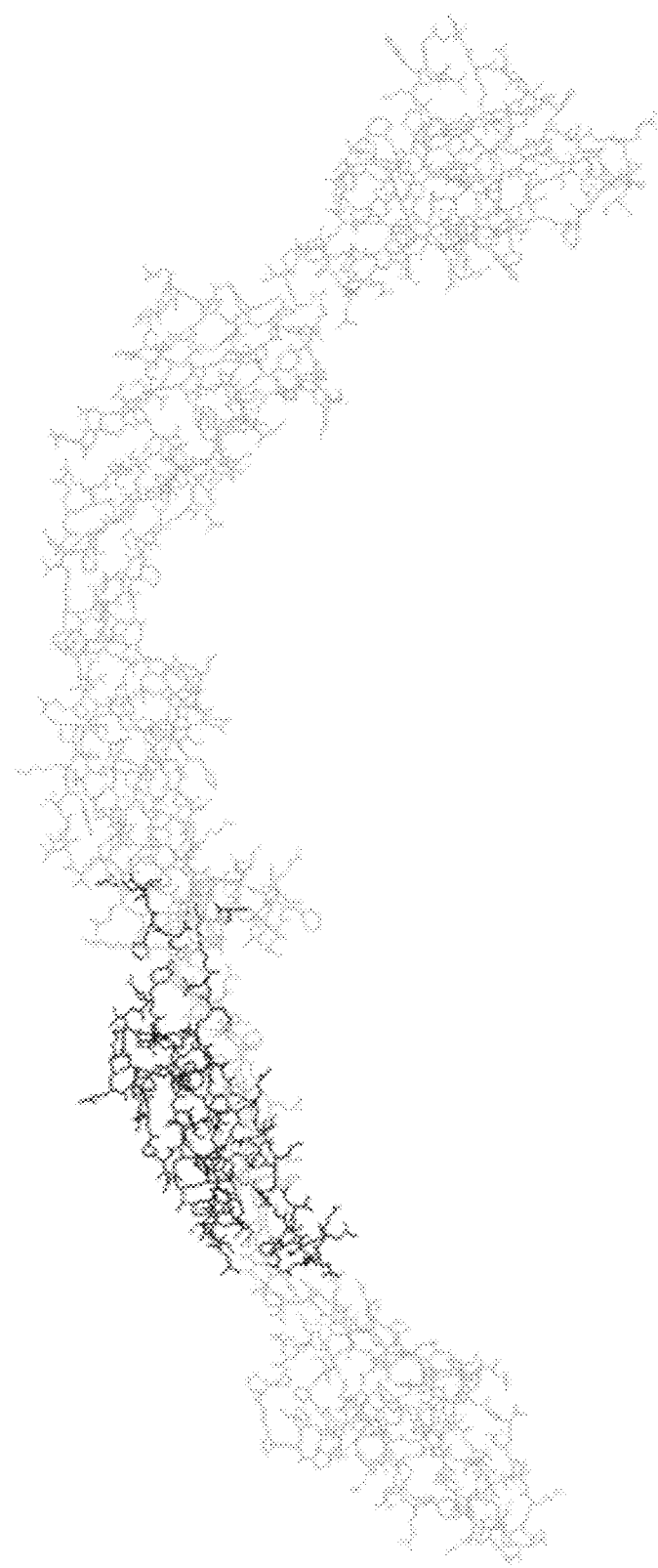
Figure 10D:
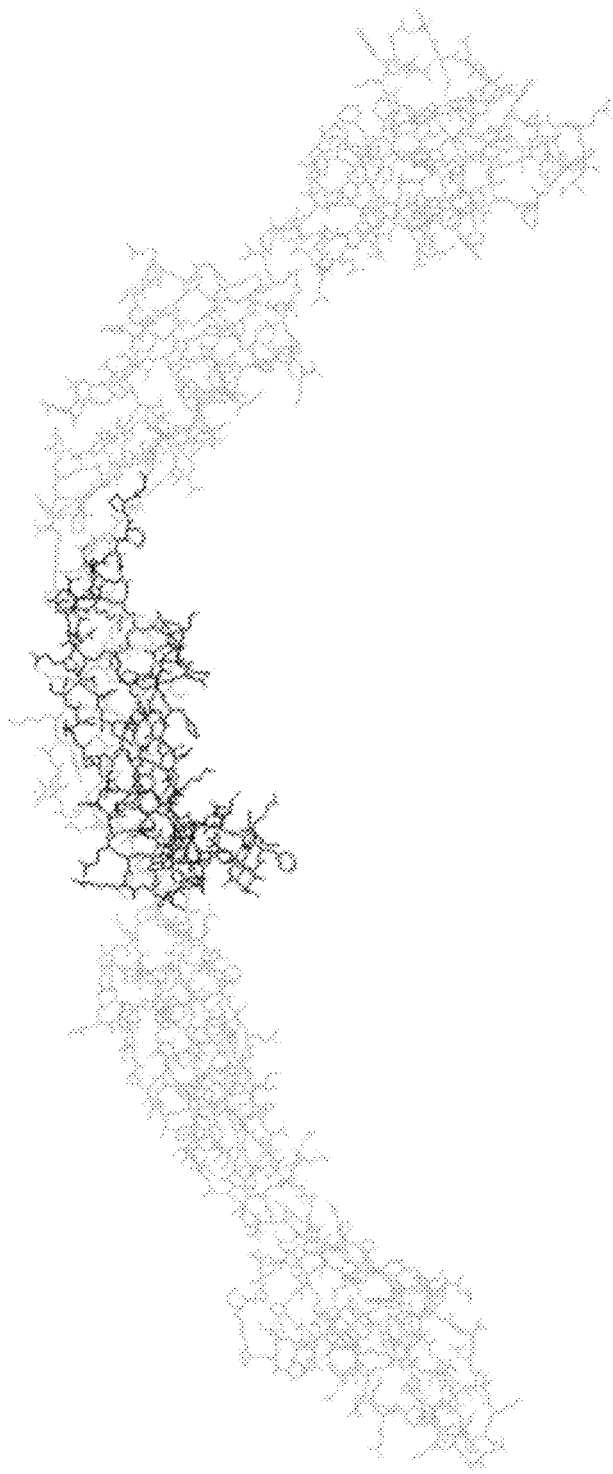
Figure 10E:
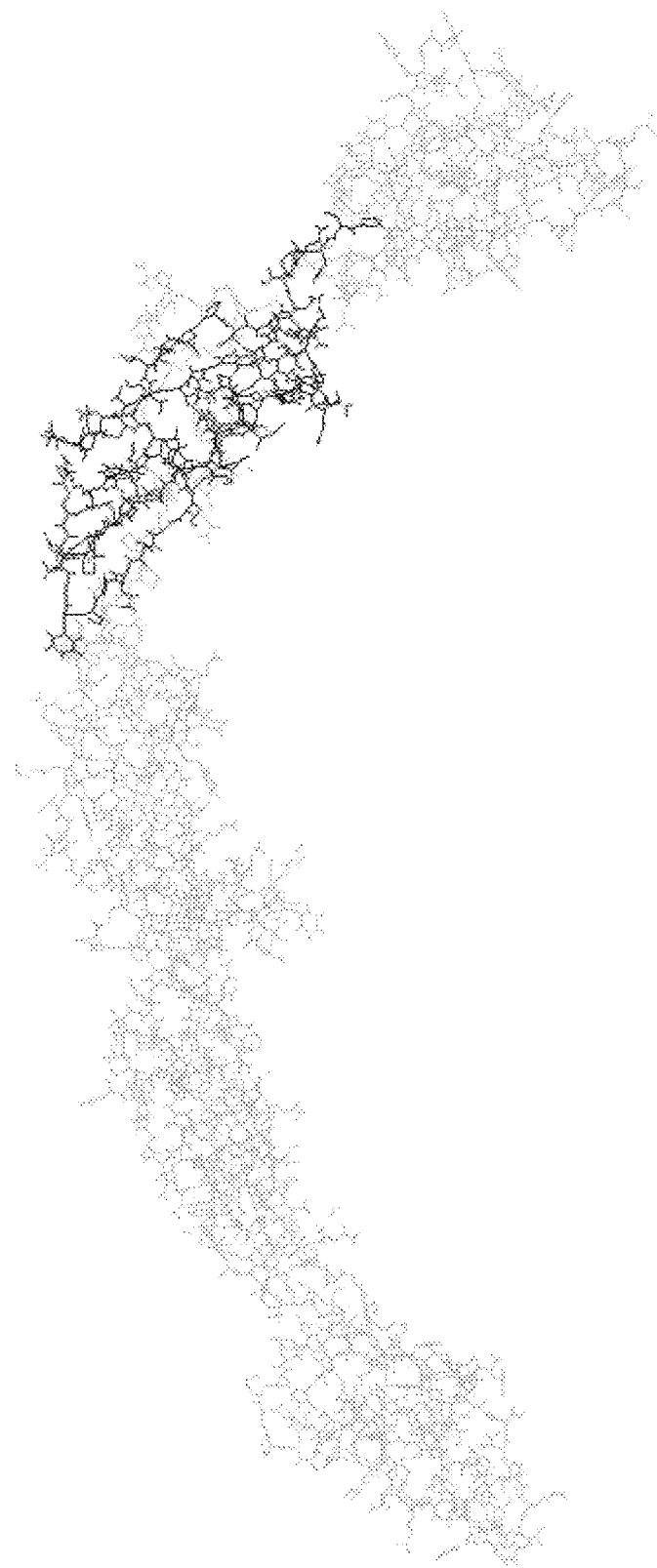
Figure 10F:
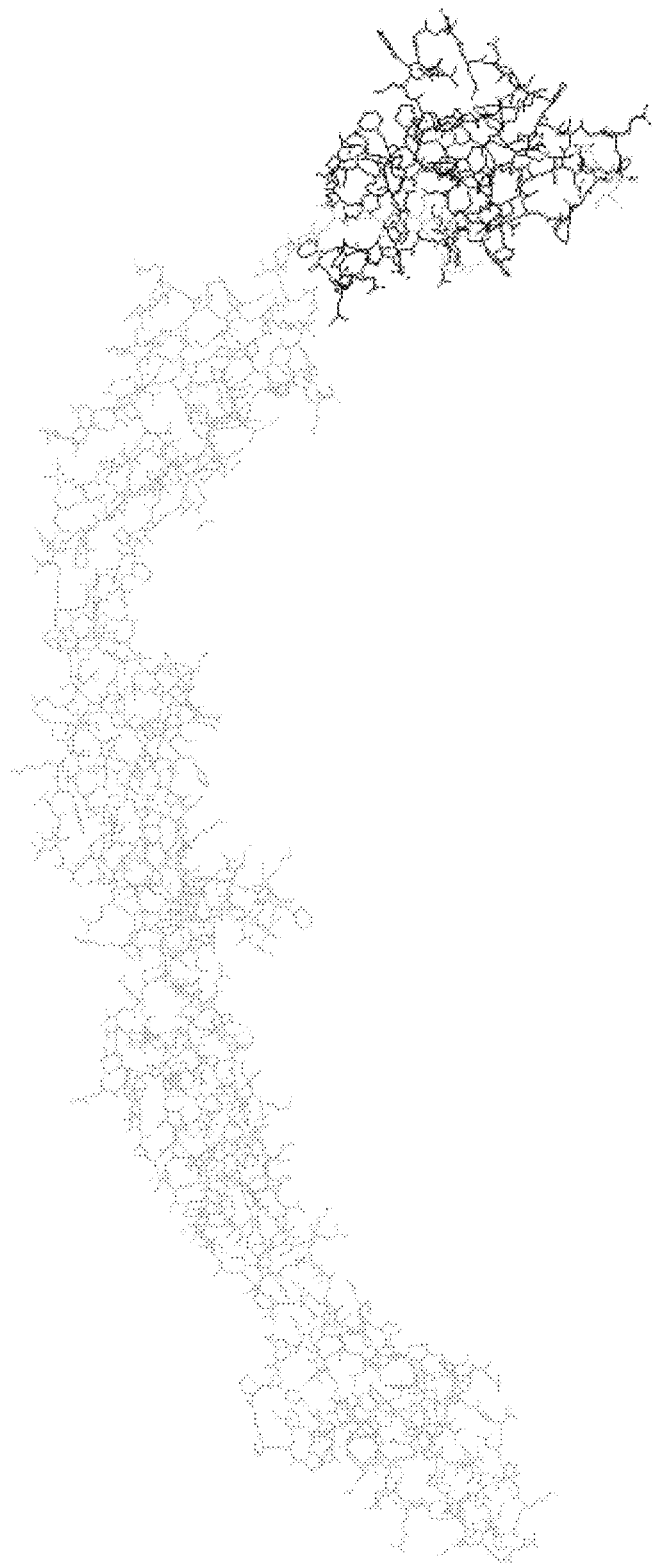

We next tested whether α4 bound to the only other beta subunit to which it is known to bind, integrin β1, could mediate interaction with CDH26 by observing whether cells that express integrin α4β1 adhered to recombinant CDH26-hIgG1-Fc. Jurkat cells, which express integrin α4β1 but not α4β7, adhered to CDH26-hIgG1-Fc to a significantly greater degree than they adhered to IgG control antibody (FIG. 6A). Pre-incubation of Jurkat cells with anti-integrin α4 antibody (HP2/1), but not an equivalent amount of control mIgG1, blocked their binding to CDH26-hIgG1-Fc in a dose-dependent manner. Jurkat cells stimulated with antibodies that activate integrin β1 (clone TS2/16) adhered to CDH26-Fc in an integrin α4-dependent manner to a greater degree than they adhered to E-cadherin-Fc (FIG. 6B). We observed that adhesion of TS2/16-stimulated Jurkat cells to CDH26-Fc was synergistically enhanced by the presence of a minimal amount of the known integrin α4β1 ligand VCAM-1-Fc; this enhanced binding was integrin α4-dependent (FIG. 6C). Although CDH26-Fc did not mediate adhesion of primary human peripheral blood CD4+ T cells at the dose tested, synergistic binding was detected when both CDH26-Fc and a minimal dose of VCAM-1-Fc were present (FIG. 6D). A similar pattern of adhesion was observed for human peripheral blood eosinophils (FIG. 6E), where the combination of CDH26-Fc and a minimal amount of VCAM-1-Fc that alone did not mediate adhesion promoted adhesion of these cells that express both integrin α4β1 and integrin α4β7.

CDH26 Modulates CD4+ T Cell Activation

Since other α4β1 ligands including VCAM-1 have been shown to co-stimulate CD4+ T cell activation, we sought to test the hypothesis that the putative integrin α4 ligand CDH26 had this property. Surprisingly, CDH26-Fc inhibited co-stimulation of isolated human peripheral blood CD4+ T cells activated by suboptimal stimulation of the T cell receptor (TCR) mediated by anti-CD3 antibodies (clone OKT3). After human peripheral blood CD4+ T cells were incubated for 48 h in the presence of plate-bound OKT3, an increased percentage of the cells expressed CD25 and CD69 at the cell surface, and the mean fluorescence intensity (MFI) of both molecules was increased (FIG. 7A-B). However, the presence of plate-bound CDH26-Fc inhibited both the increase in percentage of cells expressing CD25 and CD69 as well as the increased MFI of both molecules in a dose-dependent manner (FIG. 7A-B). We additionally tested whether CDH26-Fc inhibited CD4+ T cells co-stimulated with a suboptimal dose of OKT3 and VCAM-1-Fc. Indeed, as previously reported, VCAM-1-Fc co-stimulated CD4+ T cells treated with a suboptimal dose of OKT3; this co-stimulation was dramatically inhibited by CDH26-Fc as indicated by a decreased percentage of cells expressing CD25, CD69, and CD125 at the cell surface and by a decreased MFI of these molecules (FIG. 7A-C). Production of the cytokines IL-2 and IL-4 was inhibited by CDH26-Fc in a dose-dependent manner both in cells subjected to suboptimal TCR stimulation as well as in cells costimulated with VCAM-1-Fc (FIG. 7D).

Discussion

Herein we have elucidated the properties of CDH26, identifying it as a functional cadherin with unique features in that it is the only cadherin family member significantly upregulated in human allergic gastrointestinal tissue, where it localizes to epithelial cells in the inflamed esophagus and stomach. The Th2 cytokine IL-13, which we demonstrate is increased in allergic eosinophilic gastroenteropathy, is sufficient to drive CDH26 gene expression in epithelial cells in vitro. CDH26 mediates calcium-dependent cell adhesion, dimerizes/multimerizes, and interacts with alpha-, beta-, and p120-catenins. CDH26 engagement alters intracellular signaling including activation of ERK. Furthermore, epithelial cells overexpressing CDH26 display a distinct gene expression profile compared to control cells that includes transcripts related to cell adhesion and differentiation, and about 20% (16/86) of the identified transcripts overlap with those known to be regulated by IL-13 in primary esophageal epithelial cells. CDH26 also has the ability to impact leukocyte migration and adhesion including eosinophil transmigration through CDH26+ cells. Moreover, we present biochemical and functional evidence that CDH26-integrin interactions impact cellular adhesion; specifically, integrins α4 and αE co-immunoprecipitate with CDH26, recombinant CDH26-hIgG1-Fc binds recombinant α4β7, CDH26-expressing cells adhere to integrin α4β7, and Jurkat cells adhere to recombinant CDH26-hIgG1-Fc in a manner dependent on integrin α4. Besides uncovering a novel role for this molecule, we present evidence that it can be exploited to generate a potential therapeutic as CDH26-Fc is an immunosuppressive molecule. Taken together, we have identified a novel functional cadherin regulated during allergic inflammation, determined that it binds α integrins, and has immunomodulatory properties.

The fact that CDH26 was the only cadherin transcript differentially regulated in both EoE and EG suggests that it may modulate specific biological functions in Th2-associated conditions. Coordinated or aberrant changes in cadherin expression by particular cell types have been observed to impact parameters including motility, proliferation, and differentiation state such as during epithelial-mesenchymal and mesenchymal-epithelial transition (EMT/MET), which does occur in Th2 immune responses. It is notable that CDH26 overexpression in esophageal epithelial cells drove increased expression of several genes known to be involved in promoting or to reflect epithelial cell differentiation (e.g. KRT14, KRT5, KRT6A). In contrast to the upregulation of CDH26, another cadherin superfamily member, desmoglein-1, has recently been shown to be downregulated in EoE and to be responsible in part for induction of impaired barrier function, Th2 immune responses, and altered epithelial differentiation. These observations suggest appropriate coordinated expression of cadherin superfamily members is important in multiple facets of Th2 immune responses.

We additionally observed that IL-13 is sufficient to drive an increase in CDH26 transcripts in gastric and esophageal epithelial cells. The sequence several kilobases upstream of the transcription start site of CDH26 does contain two weak STAT consensus binding sequences, while the first intron contains a STAT6 consensus binding sequence. Furthermore, CDH26 is induced by IL-13 with similar kinetics compared to CCL26 (eotaxin-3), a direct target of IL-13 signaling. IL-13-mediated induction of CDH26 in TE-7 esophageal epithelial cells is inhibited by expression of dominant-negative STAT6. These factors suggest that increased CDH26 transcription by epithelial cells is directly mediated by IL-13 signaling and that in vivo CDH26 expression may be controlled at least in part by the observed increase in IL13 levels. This is consistent with previous in vitro evidence that Th2 cytokines including IL-4 and IL-13 induce CDH26 transcript expression by normal human bronchial epithelial cells. This common regulation of epithelial expression of CDH26 by Th2 cytokines may point to a conserved function of CDH26 in allergic inflammation extending beyond the gastrointestinal tract.

We observed that engagement of CDH26 resulted in ERK activation in CDH26-expressing cells. Several possibilities exist for the mechanism by which cadherin engagement impacts intracellular signaling. Cadherins can form ligand-independent complexes with receptor tyrosine kinases (RTKs) including the epidermal growth factor receptor (EGFR), fibroblast growth factor receptor (FGFR), and vascular-endothelial growth factor receptor 2 (VEGFR2). Alternatively, CDH26 interaction with alpha-catenin and p120-catenin may regulate MAPK pathways; alteration of the activation state or localization of these molecules upon cadherin engagement could converge on MAPK signaling. ERK activation following CDH26 engagement could have diverse consequences including, but not limited to, alteration of gene expression important for proliferation and differentiation, as well as transcription-independent activation of pathways involved in cell motility.

We found that human eosinophils showed enhanced transmigration to eotaxin-1 through cells expressing high levels of CDH26. Although several explanations for the enhanced transmigration exist, we hypothesize that CDH26 expressed by the HEK 293T cells interacts with a cell surface protein expressed by eosinophils, such as an integrin, to enhance cell migration. More specifically, interaction between CDH26 expressed by epithelial cells and α4 integrin expressed by eosinophils may influence eosinophil localization, retention, or activation status within the allergic esophageal and gastric mucosa. Given our observation that CDH26 interacts with not only integrin α4 but also integrin αE, we further speculate that CDH26, which is expressed highly under inflammatory conditions, might have a function similar to E-cadherin to regulate localization or activation of leukocytes during allergic responses via interacting with leukocyte integrins. In addition to eosinophils, epithelial CDH26 may impact the localization or activation status of diverse α4+ and/or αE+ cells (e.g. CD4+ T cells, mast cells) within the epithelium in the context of allergic inflammation.

We identified several lines of evidence that CDH26 interacts with alpha integrins and facilitates cellular binding to α4-containing integrins, including both integrin α4β7 and α4β1. Biochemical assays suggested that the extracellular portion of CDH26 could directly bind the α4-containing integrin α4β7. Furthermore, we observed that cells expressing high levels of CDH26 adhered to recombinant integrin, and in the reciprocal situation, recombinant CDH26 was sufficient to mediate adhesion of Jurkat T cells in a manner dependent on integrin α4. Such interactions are consistent with the structural properties of CDH26, which include the presence of solvent-exposed acidic residues that could be critical to facilitate the CDH26/integrin interaction. We speculate that in addition to mediating adhesion, interaction of epithelial-expressed CDH26 with leukocyte integrins could initiate intracellular signaling in both the epithelial cell and the leukocyte. This could impact diverse processes such as alteration of gene expression, regulation of barrier function, or production of mediators by either cell type, serving to inhibit or augment allergic responses.

In summary, we have characterized the previously unstudied CDH26 and found that it is a functional cadherin with a potential role in promoting allergic responses in part through influencing epithelial gene expression and leukocyte adhesive and transmigration responses. This function could be carried out through interaction of epithelial-expressed CDH26 with counterligands expressed by inflammatory cells such as integrins. As such, CDH26 could drive Th2 inflammation by promoting α4+ and αE+ immunocyte localization within the affected tissue. CDH26 is now the second cadherin (besides CDH1) that has been shown to bind α-integrins, extending the paradigm of cadherin/integrin interactions.

Methods

Protein Extracts and Immunoprecipitation (IP)

Cell lysates were prepared from HEK 293T cells generally as described previously. Cells (approximately $2 \times 10^6$) were washed one time with PBS and incubated in IP buffer (50 mM Tris-HCl [pH 7.4], 150 mM NaCl, 2 mM EDTA, 1 mM dithiothreitol, 1% Nonidet P-40 [NP-40]; or 10 mM imidazole, 100 mM NaCl, 1 mM $MgCl_2$, 5 mM EDTA, 1% Triton X-100, pH 7.4) containing 1× cOmplete protease inhibitor cocktail (Roche) for 10 min on ice. Cells were scraped from the plate and rotated at 4° C. for 10 min Lysates were cleared by centrifugation at 20,000×g at 4° C. for 10 min. An equal amount of protein was added to total 500 microliters of IP buffer plus protease inhibitors (Roche). Antibodies (2 micrograms α-HA (Covance), α-myc (Covance), α-p120 (BD Transduction Laboratories), α-ITGA4 (Cell Signaling Technology, Inc.), mouse IgG1 control (AbD Serotec), or normal rabbit IgG control (R & D Systems)) were added and rotated overnight at 4° C. Subsequently, 20 microliters of protein A/G agarose beads (Santa Cruz Biotechnology, Inc.) were added per sample. After 2 h of rotation (4° C.), beads were washed 5 times in IP buffer containing protease inhibitors. 2X Laemmli buffer was added to the immunoprecipitates or total cell lysates saved prior to IP (input).

Biopsy Protein Extracts

Distal esophagus or gastric antrum biopsy specimens were transferred into 100 microliters of IP buffer (50 mM Tris-HCl [pH 7.4], 150 mM NaCl, 2 mM EDTA, 1 mM dithiothreitol, 1% Nonidet P-40 [NP-40], 1× protease inhibitors (Roche)) and sonicated. Lysates were cleared by centrifugation (20,000×g, 4° C., 10 min). Alternatively, protein was isolated from the organic fraction remaining after RNA isolation from biopsy specimens using the miRNeasy kit (Qiagen). DNA was precipitated by the addition of 0.3 volumes of ethanol followed by a 2,000×g spin. Protein was precipitated from the supernatant by addition of 3 volumes of acetone, pelleted by centrifugation (20,000×g, 10 min, 4° C.), dried, and solubilized in Laemmli buffer (2×).

Design and Production of CDH26-hIgG1-Fc Fusion Protein

To produce a chimeric CDH26-Fc protein composed of the extracellular domain of human CDH26 in frame with an Fc portion of a human IgG1, we first identified amino acids 1-613 as the putative extracellular domain of CDH26 using omain prediction based on analysis of the primary amino acid sequence. Next, we aligned the CDH26 primary amino acid sequence with that of human CDH1 using Clustal Omega to identify the CDH26 residues corresponding to those of CDH1 that had been included in the CDH1-Fc reported by Higgins et al. 1998 in the Journal of Cell Biology. The corresponding CDH26 residues were identified as amino acids 603-605. Three additional amino acids located immediately C-terminal of amino acids 603-605 were also included, so that the final portion of human CDH26 included in CDH26-Fc was amino acids 1-608.

For the Fc portion of the fusion protein, we used the human IgG1-Fc sequence from the expression plasmid pFUSE-hIgG1-Fc1 (Invitrogen).

The cloning strategy included a two-step PCR and traditional molecular cloning techniques to insert the nucleotides encoding human CDH26 amino acids 1-608 in frame with the nucleotides encoding the human IgG1-Fc region of pFUSE-hIgG1-Fc. The cloning strategy also involved placement of a Kozak sequence located immediately 5 prime of the sequence encoding the start codon of the fusion protein. The resulting plasmid is denoted pFUSE-CDH26-hIgG1-Fc. Because a stable cell line producing high levels of CDH26-Fc was desired, the sequence from the pFUSE-CDH26-hIgG1-Fc plasmid including the Kozak sequence and open reading frame of CDH26-Fc was transferred into the pMIRNA1-puro lentiviral vector to make a construct denoted pMIRNA1-puro-hCDH26-hIgG1-Fc. HEK 293T cells were transduced with lentivirus produced from pMIRNA1-puro-hCDH26-hIgG1-Fc and were placed under puromycin selection. Puromycin-resistant cells were dispersed, and limiting dilutions of the cells were plated. Single clones were isolated and assessed for their level of protein production. Clones that produced high levels of CDH26-Fc were expanded, and supernatant from the cells was subjected to protein G affinity chromatography to isolate CDH26-Fc.

HEK 293T cells (20×150 mm dishes) stably transduced with pMIRNA1-CDH26-hIgG1-Fc (described in Constructs) were grown in DMEM containing 10% ultra-low IgG FBS (Invitrogen). After 8 days, the supernatants from all dishes were combined. The supernatants were filtered (0.2 micron) and the resulting volume was diluted 1:1 in binding buffer (20 mM HEPES, 50 mM NaCl, 1 mM $CaCl_2$, pH 7.4) and then passed over a protein G column (GE Healthcare) that had been pre-washed with binding buffer. The column was then washed with binding buffer, and fusion protein was eluted in fractions using 100 mM glycine, pH 3.0. The eluates were immediately neutralized by the addition of an equal amount of 1 M Tris HCl, pH 8.0. Fractions were assayed by SDS-PAGE and Coomassie stain as well as western blot analysis to identify the fractions that contained the fusion protein. The pooled five fractions containing the most fusion protein were desalted using G20 columns (GE Healthcare) and binding buffer. Control hIgG1κ antibody (low endotoxin, azide-free preparation) (Southern Biotech) was also desalted in a similar manner Quantitation of LPS in the isolated proteins using the Limulus amebocyte lysate (LAL) chromogenic endotoxin quantitation kit (Thermo Scientific) showed that the CDH26-Fc preparations had endotoxin concentrations of less than 0.2 endotoxin units (EU)/ml, which was lower than that detected in the control hIgG1κ antibody.

Eosinophil Transmigration Assay

HEK 293T cells transduced with either pMIRNA1-control or -CDH26 were plated on Costar transwell inserts (polycarbonate, 6.5 mm diameter, 0.3 micron pore size) (Corning Inc.). Eosinophils ($1.3 \times 10^5$ at a density of $1 \times 10^6$ cells/ml suspended in 1×HBSS plus 1 mM $CaCl_2$ plus 2% FBS) were applied to the top of the transwell, while the bottom chamber of the transwell contained 1×HBSS with 1 mM $CaCl_2$ and 2% FBS and the indicated concentration of chemoattractant (human eotaxin-1, Peprotech). Reactions were incubated at 37° C. for 1.5 h. Transwells were then subjected to Wright-Giemsa staining per the manufacturer's protocol (Harleco, EMD Millipore) to confirm the confluency of the cells. The number of eosinophils present in the lower chambers was then assessed by hemocytometry.

Cell Adhesion to Recombinant Integrin Assay

Recombinant human α4β7 (R&D Systems) was diluted to the indicated concentration in buffer (150 mM NaCl, 20 mM HEPES), and 100 microliters per well was added to half-well Costar ELISA plates (Corning) and incubated overnight at 4° C. The following day, wells were washed and coated with 5% BSA in buffer (150 mM NaCl, 20 mM HEPES) (3 h, 37° C.). L929 cell clones transduced with the indicated construct and grown to confluency were then dispersed and resuspended in assay buffer (150 mM NaCl, 20 mM HEPES, 1 mM $CaCl_2$, 1 mM $MgCl_2$, 1 mM $MnCl_2$). For each cell type, 50,000 cells were added per well. The plate was spun at 10×g for 1 min and subsequently incubated at 37° C. for 1 h. Wells were washed by gravity one time by inverting the plate in a large beaker of assay buffer for 10 min. Two additional washes were performed by pipetting 100 microliters of assay buffer into the wells 4 times per wash. Fluorescence was measured prior to the washes and after each wash using a plate reader (ex/em 485/20 nm/528/20 nm) (BioTek). The results are expressed as the percent fluorescence remaining (fluorescence after the last wash/initial fluorescence) for each well.

Statistical Analysis

Data are expressed as mean±SEM or median±interquartile range. Statistical significance was determined using the unpaired t test (2 groups, normal distribution, equal variance), Mann-Whitney test (2 groups, nonparametric), 1-way ANOVA followed by the Tukey post-test (>2 groups), the Kruskal-Wallis test followed by Dunn's multiple comparison test (>2 groups, nonparametric), or 2-way ANOVA (calcium switch kinetic experiment) with Prism 5.0 software (GraphPad Software, Inc.). For microarray analysis, gene transcript levels were determined and statistical analysis was performed using algorithms in GeneSpring GX 7.3 software or GeneSpring 12.5 software (Agilent). More specifically, moderated t test, a modification of the unpaired t test that pools variation data for many genes instead of using single-gene estimated variances, was performed using GeneSpring 12.5. Gene ontology analysis was performed by submitting ranked gene lists to GOrilla, which uses an exact mHG p-value computation. A P-value threshold of 10-3 was set to identify significantly enriched terms, and multiple test correction was then applied (Benjamini and Hochberg method).

Expression Constructs pCDNA3.1(−) was obtained from Promega. pLX304-hITGAE-V5 (ID HsCD00436970) was obtained from DNASU Plasmid Repository (The Biodesign Institute, Arizona State University). Expression plasmids were constructed by PCR amplification of the relevant open reading frame. PCR products were then ligated into the following restriction sites of pCDNA3.1(−): pCDH26-HA: EcoRI/KpnI, pCDH26-MYC: EcoRI/KpnI, pCDH26: EcoRI/NotI, pHA-CTNNB1: XbaI/KpnI, pCTNNB1-HA: XbaI/KpnI, pCTNNA1-HA: EcoRI/KpnI, pCTNND1: EcoRI/KpnI, pITGA4: XhoI/NotI, pITGB7, NotI/EcoRI, pCDH1: NotI/HindIII. pMIRNA1-puro-control has been described previously and is referred to as "pMIRNA1-control" henceforth.

pMIRNA1-CDH26 was constructed by introducing the CDH26 open reading frame into the EcoRI and NotI sites of pMIRNA1-control. pFUSE-CDH26-hIgG1-Fc was constructed by first amplifying nucleotides encoding the extracellular domain of CDH26 using primers 5067 and 5108 with pCDH26 as template. These primers introduced a region of nucleotide sequence complementary to the 5' portion of hIgG1-Fc at the 3' end of the PCR product. This PCR product was isolated and used as a primer along with primer 5109 in a second PCR reaction using pFUSE-hIgG1-

Fc1 plasmid (Invitrogen) as template. The resulting PCR product was then digested with EcoRI and BsrGI restriction enzymes and ligated into the corresponding sites of pFUSE-hIgG1-Fc1 plasmid. This construct and pCDH26 were then digested with EcoRI and SalI, and the 1329 base pair restriction fragment from pCDH26 was ligated into the corresponding restriction sites of the pFUSE-based EcoRI/SalI-digested construct. Primers 5254 and JC650 were then used to amplify the CDH26-Fc open reading frame, and it was introduced into the NotI restriction site of pMIRNA1-control to make pMIRNA1-CDH26-hIgG1-Fc.

Lentivirus Production and Transduction of HEK 293T, TE-7, and L929 Cells

For pMIRNA1 constructs, lentivirus production was carried out by the CCHMC Viral Vector Core. HEK 293T cells were transduced by incubating lentivirus with the cells for 24 h in the presence of 5 micrograms per milliliter polybrene. Media were then changed, and after 24 h medium containing 2 micrograms per milliliter puromycin was added. After selection for 48 h in puromycin, cells were dispersed and plated to single cells in 96 well plates to obtain clones derived from single cells. A second round of dispersing, plating to single cells, and picking single colonies was done. CDH26 expression was verified by western blot analysis and FACS analysis. TE-7 and L929 cells were transduced in the same manner, except only one round of selection for clones was performed, and CDH26 expression was verified by western blot analysis.

Aggregation Assay

Calcium-dependent aggregation assays were carried out as described previously, with minor modifications. HEK 293T or L929 cells were treated with DMEM containing 0.1% trypsin at a final concentration of 5 mM $CaCl_2$ (30 mM, 37° C.). Cells were washed once with DMEM containing 10% FBS and then twice with 1×HBSS containing 1% FBS. Cells were counted, and $2×10^6$ cells were aliquoted into 1.5-ml tubes (two tubes per cell type). Cells were spun down and resuspended in HEPES-buffered magnesium-free saline (HMF; 10 mM HEPES in saline) that either contained or lacked 1 mM $CaCl_2$. The initial particle number was counted, and the tubes were rotated at 37° C. for 30 mM The final particle number was then counted. The aggregation index was expressed as [(initial particle number−final particle number)/initial particle number].

Solid Phase Adhesion Assay

Recombinant human integrin $α4β7$ (R&D Systems) was diluted to the indicated concentration in buffer (150 mM NaCl, 20 mM HEPES); 100 microliters per well was added to Costar half-well ELISA plates (Corning Inc.) and incubated overnight at 4° C. The following day, wells were washed and blocked with 5% BSA in buffer (150 mM NaCl, 20 mM HEPES) overnight at 4° C. The following day, the wells were washed, and IgG1κ or CDH26-hIgG1-Fc diluted in assay buffer (150 mM NaCl, 20 mM HEPES, 1 mM $CaCl_2$, 1 mM $MgCl_2$, 1 mM $MnCl_2$) containing 5% BSA was added to wells for 60 mM at 37° C. Wells were washed 3×, and detection antibody (biotinylated anti-human IgG1 (Vector Laboratories, Inc.); 0.5 micrograms per milliliter in assay buffer with 5% BSA) was added for 2 h at room temperature. Wells were washed 3× with assay buffer with 5% BSA and streptavidin-HRP was added (1:200 in assay buffer with 5% BSA; R & D Systems). Wells were washed 3× with assay buffer with 5% BSA, and a 1:1 dilution of TMB substrate (BD Biosciences) was added. The reaction was stopped by the addition of 2N H2SO4. Absorbance at 450 nm and 900 nm was measured using a plate reader (BioTek).

Jurkat, CD4+ T Cell, and Eosinophil Adhesion Assay

CDH26-hIgG1-Fc, CDH1-Fc (R&D Systems), VCAM-1-Fc (R&D Systems), and/or hIgG1 (Southern Biotech) was diluted in buffer (150 mM NaCl, 20 mM HEPES) to appropriate concentrations so that the indicated amount of protein was added to Costar half-well ELISA plates in 50 microliters per well (Corning, Inc.) and incubated overnight at 4° C. The next day, Jurkat cells or isolated CD4+ T cells ($1×10^6$/ml) were incubated in HEPES medium (132 mM NaCl, 6 mM KCl, 1 mM $CaCl_2$, 1 mM $MgSO_4$, 1.2 mM $KH_2PO_4$, 20 mM HEPES, 5.5 mM glucose, 0.5% BSA) plus 4 micrograms per milliliter calcein-AM (Sigma-Aldrich) for 1 h at 37° C. Cells were washed 3× in HEPES medium. In the indicated cases, cells were incubated with 1.4 micrograms of either anti-integrin β1-activating antibodies (clone TS2/16, Santa Cruz Biotechnology) or an equivalent amount of mIgG1 (Southern Biotech). In the indicated cases, labeled cells were then pre-incubated with the indicated concentration (0.13 micrograms per milliliter to 0.026 micrograms per milliliter) of either mIgG1 (AbD Serotec) or anti-integrin alpha 4 (HP2/1; AbD Serotec) antibodies in assay buffer for non-TS2/16-treated cells (150 mM NaCl, 10 mM HEPES, 1 mM $CaCl_2$, 1 mM $MgCl_2$, 1 mM $MnCl_2$) or HEPES medium for TS2/16-treated cells for 15 min at 4° C. prior to their addition to wells (50,000 cells/well). Plates were spun at 10×g for 1 min and then incubated at 37° C. for 45 min. Initial fluorescence per well was then measured using a plate reader ((ex/em 360/40 nm/460/40 nm); BioTek). Wells were washed by gravity one time by inverting the plate in a large beaker of assay buffer for 10 min. Two additional washes were performed by pipetting 100 microliters of assay buffer into the wells 4 times per wash. Final fluorescence was then measured. For eosinophil adhesion assays, isolated human peripheral blood eosinophils were pre-activated with 1.4 micrograms of either TS2/16 or mIgG1 control antibodies. The cells were then incubated with anti-CD32 antibodies (Stem Cell Technologies, Inc.). Eosinophils were then allowed to adhere to plates that had been coated with the indicated amount of protein(s) as described above for Jurkat and CD4+ T cell adhesion assays. Three washes were performed, and residual eosinophil peroxidase activity for each well was measured as a surrogate for the number of eosinophils that remained adhered to the wells after the washes.

T Cell Activation Assay

The indicated amounts of anti-CD3 (clone OKT3, eBioscience) antibodies, CDH26-hIgG1-Fc, CDH1-Fc (R&D Systems), VCAM-1-Fc (R&D Systems), and/or hIgG1κ control antibody (Southern Biotech) were suspended in coating buffer (20 mM HEPES, 150 mM NaCl), added to wells of a 96 well cell culture plate, and incubated overnight at 4° C. The following day, isolated human peripheral blood CD4+ T cells (150,000 per well) were added to the wells in RPMI supplemented with 10% PBS, 1% penicillin/streptomycin, and 200 mM glutamine Cells were incubated for 48 h. Cells and supernatants were then collected for analysis by flow cytometry and ELISA, respectively.

What is claimed is:

1. A fusion protein comprising two polypeptide segments, 1 and 2, segment 1 comprising or consisting of an extracellular region of the human cadherin 26 (CDH26) protein defined by EC1 (SEQ ID NO: 2), or fragment thereof, said fragment consisting of from 20-50 contiguous amino acids of SEQ ID NO: 2, and segment 2 comprising or consisting of a heavy chain constant region (Fc) of a human immunoglobulin (Ig) molecule.

2. The fusion protein of claim 1, wherein segment 1 comprises one or more additional extracellular cadherin repeat domains (EC) of human CDH26 selected from the group consisting of EC2, EC3, EC4, and EC5.

3. The fusion protein of claim 2, wherein segment 1 comprises or consists of SEQ ID NO: 10.

4. The fusion protein of claim 2, wherein segment 1 further comprises EC2 (SEQ ID NO: 3), or a contiguous amino acid fragment thereof, said fragment consisting of from 20 to 50 contiguous amino acids of SEQ ID NO: 3.

5. The fusion protein of claim 2, wherein segment 1 further comprises EC50 (SEQ ID NO: 4), or a contiguous amino acid fragment thereof, said fragment consisting of from 20 to 50 contiguous amino acids of SEQ ID NO: 4.

6. The fusion protein of claim 2, wherein segment 1 comprises or consists of EC4 (SEQ ID NO: 5), or a contiguous amino acid fragment thereof, said fragment consisting of from 20 to 50 contiguous amino acids of SEQ ID NO: 5.

7. The fusion protein of claim 2, wherein segment 1 comprises or consists of EC5 (SEQ ID NO: 6), or a contiguous amino acid fragment thereof, said fragment consisting of from 20 to 50 contiguous amino acids of SEQ ID NO: 6.

8. The fusion protein of claim 1, wherein the Ig molecule is selected from the group consisting of IgG, IgE, IgM, IgD, IgA and IgY.

9. The fusion protein of claim 8, wherein the Ig molecule is an IgG or IgA molecule.

10. The fusion protein of claim 9, wherein the IgG or IgA molecule is selected from the group consisting of IgG1, IgG2, IgG3, IgG4, IgA1 and IgA2.

11. The fusion protein of claim 10, wherein the Ig molecule is selected from the group consisting of IgG1, IgG4, IgA1 and IgA2.

12. The fusion protein of claim 11, wherein the Ig molecule is IgG1.

13. The fusion protein of claim 12, wherein segment 2 comprises or consists of SEQ ID NO: 7.

14. The fusion protein of claim 1, further comprising a signal sequence.

15. The fusion protein of claim 14, wherein the signal sequence is selected from a signal peptide of any one of interleukin-2, CD5, immunoglobulin kappa light chain, trypsinogen, serum albumin, and prolactin, and functional fragments thereof.

16. The fusion protein of claim 1, further comprising a linker sequence between segments 1 and 2.

17. The fusion protein of claim 16, wherein the linker sequence comprises or consists of from 2 to 10 amino acids.

18. The fusion protein of claim 1, wherein the fusion protein comprises or consists of SEQ ID NO: 8.

19. A modified fusion protein according to claim 1, wherein the amino acid sequence of the modified fusion protein is from 90 to 99% identical to the unmodified sequence.

20. A modified fusion protein according to claim 1, wherein the sequence of segment 2 is modified to improve the aqueous solubility, stability, avidity, and/or pharmacokinetics of the fusion protein.

21. The modified fusion protein of claim 20, wherein the sequence of segment 2 is modified to reduce complement binding or antibody dependent cytotoxicity.

22. A composition or pharmaceutical composition comprising the fusion protein of claim 1.

23. The composition or pharmaceutical composition of claim 22, further comprising a pharmaceutically acceptable carrier or excipient.

24. The composition or pharmaceutical composition of claim 23, which is formulated for topical administration.

25. The composition or pharmaceutical composition of claim 23, further comprising at least one additional active agent selected from an IL-13 inhibitor, a non-steroidal anti-inflammatory drug (NSAID), a cytokine inhibitor, a bronchodilator, omalizumab, mepolizumab, or reslizumab, an immunosuppressive agent, 6 mercaptopurine, or a steroid.

26. A method for treating an inflammatory disease, disorder, or condition in a subject in need thereof, the method comprising administering to the subject an amount of the pharmaceutical composition of claim 23.

27. A fusion protein consisting of an extracellular region of human CDH26 and an Fc region of an Ig molecule, the extracellular region of CDH26 comprising an extracellular cadherin repeat domain 1 of SEQ ID NO: 2 (EC1), or a fragment thereof, said fragment consisting of from 20-50 contiguous amino acids of SEQ ID NO: 2.

28. The fusion protein of claim 27, wherein the extracellular region further comprises one or more additional extracellular cadherin repeat domains (EC) of human CDH26 selected from the group consisting of EC2, EC3, EC4, and EC5, or a fragment thereof consisting of from 20 to 50 contiguous amino acids.

29. The fusion protein of claim 28, wherein the extracellular region comprises or consists of SEQ ID NO: 10.

30. The fusion protein of claim 29, wherein the Fc region comprises or consists of SEQ ID NO: 7.

31. The fusion protein of claim 27, wherein the sequence of EC1 is modified to alter integrin binding by substituting one or more amino acid residues corresponding to N85, D98, E99, E102 and E138 of SEQ ID NO:11.

32. The fusion protein of claim 27, wherein the sequence of EC1 is modified to alter homodimer formation by substituting the amino acid residue corresponding to W56 of CDH26 (SEQ ID NO:11).

33. The fusion protein of claim 28, wherein the sequence is modified to alter glycosylation of the fusion protein by substituting one or more amino acids residues corresponding to N81, N85, N171, N177 and N462 of CDH26 (SEQ ID NO:11).

* * * * *

UNITED STATES PATENT AND TRADEMARK OFFICE
CERTIFICATE OF CORRECTION

PATENT NO. : 10,435,452 B2
APPLICATION NO. : 15/577502
DATED : October 8, 2019
INVENTOR(S) : Marc E. Rothenberg et al.

It is certified that error appears in the above-identified patent and that said Letters Patent is hereby corrected as shown below:

In the Claims

At Column 51, Claim number 5, Line number 60 reads:
"further comprises EC50 (SEQ ID NO: 4), or a continguous"

Should read:
-- further comprises EC3 (SEQ ID NO: 4), or a continguous --

Signed and Sealed this
Twenty-sixth Day of November, 2019

Andrei Iancu
*Director of the United States Patent and Trademark Office*